United States Patent
Sahiholnasab et al.

(10) Patent No.: US 11,207,630 B2
(45) Date of Patent: Dec. 28, 2021

(54) AEROSOL PROTECTION SYSTEM

(71) Applicants: Seyed Vahid Sahiholnasab, Richmond (CA); Joel Nicholas Fransen, Richmond (CA); Kiomars Anvari, Walnut Creek, CA (US); Edmond Zahedi, Burnaby (CA)

(72) Inventors: Seyed Vahid Sahiholnasab, Richmond (CA); Joel Nicholas Fransen, Richmond (CA); Kiomars Anvari, Walnut Creek, CA (US); Edmond Zahedi, Burnaby (CA)

(73) Assignee: AEROCONTAIN TECHNOLOGIES INC., British Colombia (CA)

( * ) Notice: Subject to any disclaimer, the term of this patent is extended or adjusted under 35 U.S.C. 154(b) by 0 days.

(21) Appl. No.: 16/930,600

(22) Filed: Jul. 16, 2020

(65) Prior Publication Data
US 2021/0331109 A1   Oct. 28, 2021

Related U.S. Application Data

(60) Provisional application No. 63/015,549, filed on Apr. 25, 2020.

(51) Int. Cl.
   *B01D 46/00* (2006.01)
   *B01D 46/44* (2006.01)
   *A61C 19/00* (2006.01)

(52) U.S. Cl.
   CPC ......... *B01D 46/0041* (2013.01); *A61C 19/00* (2013.01); *B01D 46/444* (2013.01);
   (Continued)

(58) Field of Classification Search
   None
   See application file for complete search history.

(56) References Cited

U.S. PATENT DOCUMENTS 2,955,521 A * 10/1960 Kurek ............... F24F 9/00
                                                      454/192
3,255,686 A *  6/1966 Larson ............. F24F 9/00
                                                      454/188
(Continued)

FOREIGN PATENT DOCUMENTS

DE   2439778 A1 *  3/1976 ........... A61G 13/108
DE   2815771 A1 * 10/1979 ........... F24C 15/2028
(Continued)

OTHER PUBLICATIONS

Energy Star, Variable Speed Fan Drives, 2016, All pages https://web.archive.org/web/20210320143626/https://www.energystar.gov/products/low_carbon_it_campaign/12_ways_save_energy_data_center/variable_speed_fan_drives (Year: 2016).*

*Primary Examiner* — Bobby Ramdhanie
*Assistant Examiner* — Brit E. Anbacht

(57) ABSTRACT

Hygiene regulations and social distancing are very effective in blocking short distance infections. During the lockdown, the distance rules can usually be adhered to, but what happens when the actual lockdown is over and the people meet again in a confined space? Then additional effective and efficient protection is essential to stabilize infection rates. Since the viruses are spread by contact and droplet infection, technical devices are required that effectively intervene in the chain of infection and effectively block infection. An effective protection is the respiratory mask as known since 100 years.

An alternative to mask is an aerosol protection system for various applications in environment. The protection system consists of adjustable air sucking device and air blowing device in different form factors based on application. The aerosol protection system uses either an air curtain or air (Continued)

shield to prevent the aerosol going from one side of the curtain or shield to the other side.

9 Claims, 63 Drawing Sheets

(52) U.S. Cl.
CPC ...... *B01D 2273/30* (2013.01); *B01D 2279/40* (2013.01); *B01D 2279/65* (2013.01)

(56) References Cited

U.S. PATENT DOCUMENTS

| | | | | |
|---|---|---|---|---|
| 3,350,994 | A * | 11/1967 | Guibert | F24F 9/00 454/190 |
| 3,511,162 | A * | 5/1970 | Truhan | F24F 3/163 454/187 |
| 3,776,121 | A * | 12/1973 | Truhan | F24F 9/00 454/187 |
| 3,923,482 | A * | 12/1975 | Knab | F24F 9/00 55/412 |
| 3,998,142 | A * | 12/1976 | Foreman | A61G 13/108 454/187 |
| 4,140,105 | A * | 2/1979 | Duvlis | A61G 13/108 128/847 |
| 5,096,467 | A * | 3/1992 | Matsui | B65G 53/24 454/189 |
| 5,160,517 | A * | 11/1992 | Hicks | A61G 5/10 55/385.1 |
| 5,263,897 | A * | 11/1993 | Kondo | F24F 9/00 454/189 |
| 5,322,473 | A * | 6/1994 | Hofstra | A24F 47/00 454/186 |
| 5,350,337 | A * | 9/1994 | Kondo | F24F 9/00 454/189 |
| 5,759,149 | A * | 6/1998 | Goldberg | A61M 16/16 600/22 |
| 6,152,451 | A * | 11/2000 | Bixby | A47B 25/00 273/309 |
| 6,626,971 | B1 * | 9/2003 | Forbert | F24F 1/027 55/385.2 |
| 10,758,751 | B2 * | 9/2020 | Feasey | A61F 9/029 |
| 2002/0143233 | A1 * | 10/2002 | Donnelly | A61F 7/00 600/22 |
| 2003/0188743 | A1 * | 10/2003 | Manne | A62B 18/003 128/201.22 |
| 2004/0009746 | A1 * | 1/2004 | Korman | A61G 10/04 454/284 |
| 2004/0187681 | A1 * | 9/2004 | Kishioka | B03C 3/12 95/57 |
| 2004/0192186 | A1 * | 9/2004 | Bourgeois | B01D 46/12 454/187 |
| 2004/0221554 | A1 * | 11/2004 | Iijima | F24F 3/163 55/385.2 |
| 2005/0061316 | A1 * | 3/2005 | Manne | A62B 18/003 128/200.27 |
| 2006/0063966 | A1 * | 3/2006 | Chan | F24F 9/00 600/21 |
| 2007/0042702 | A1 * | 2/2007 | Jeng | F24F 3/163 454/187 |
| 2008/0150404 | A1 * | 6/2008 | Ono | B25H 1/20 312/209 |
| 2008/0308106 | A1 * | 12/2008 | Augustine | A47C 7/744 128/205.29 |
| 2009/0264060 | A1 * | 10/2009 | Livchak | F24C 15/2057 454/61 |
| 2010/0051010 | A1 * | 3/2010 | Colburn | F24C 15/2028 126/299 D |
| 2010/0234794 | A1 * | 9/2010 | Weadock | A61G 13/108 604/20 |
| 2010/0280436 | A1 * | 11/2010 | Self | A61G 13/108 604/23 |
| 2012/0199003 | A1 * | 8/2012 | Melikov | F24F 3/163 95/273 |
| 2012/0227586 | A1 * | 9/2012 | Chan | B01D 53/04 95/273 |
| 2014/0102442 | A1 * | 4/2014 | Wilson | F24F 9/00 128/200.28 |
| 2015/0037201 | A1 * | 2/2015 | Armour | A61L 2/08 422/3 |
| 2015/0072609 | A1 * | 3/2015 | Bromley | A61G 13/108 454/187 |
| 2016/0131391 | A1 * | 5/2016 | He | F24F 9/00 454/292 |
| 2016/0236130 | A1 * | 8/2016 | Haslebacher | B01D 46/0028 |
| 2018/0021607 | A1 * | 1/2018 | Perusse | A42B 3/286 128/200.28 |
| 2018/0049911 | A1 * | 2/2018 | Alzeer | A61L 2/10 |
| 2019/0159951 | A1 * | 5/2019 | Hadley | A61G 12/005 |
| 2019/0234645 | A1 * | 8/2019 | Haar | F24F 7/06 |
| 2019/0255367 | A1 * | 8/2019 | Zereshkian | B03C 1/30 |
| 2019/0289946 | A1 * | 9/2019 | Perusse | A61M 16/107 |
| 2019/0365214 | A1 * | 12/2019 | Lloro Boada | A61C 17/08 |
| 2019/0377370 | A1 * | 12/2019 | Schuck | B25H 1/20 |
| 2020/0114734 | A1 * | 4/2020 | Zuberbuehler | B01D 46/2403 |
| 2020/0191408 | A1 * | 6/2020 | Scott | F24C 15/2042 |
| 2020/0229530 | A1 * | 7/2020 | Feher | A42B 3/286 |
| 2020/0345905 | A1 * | 11/2020 | Lin | A61M 1/80 |
| 2021/0003301 | A1 * | 1/2021 | Takayanagi | F24F 11/79 |
| 2021/0025607 | A1 * | 1/2021 | Torres | F24F 11/72 |
| 2021/0033294 | A1 * | 2/2021 | Grabon | F24F 6/04 |

FOREIGN PATENT DOCUMENTS

| | | | | |
|---|---|---|---|---|
| DE | 202018105672 | * | 12/2018 | A61G 10/02 |
| GB | 2180054 A | * | 3/1987 | F24F 9/00 |
| JP | 02290452 A | * | 11/1990 | F24F 8/10 |
| JP | 2001104411 A | * | 4/2001 | |
| JP | 2011257011 A | * | 12/2011 | |
| KR | 1956143 B1 | * | 3/2019 | A61L 2/0005 |
| KR | 2020073111 A | * | 6/2020 | A62B 18/003 |
| WO | WO-9912635 A1 | * | 3/1999 | B01D 46/4227 |
| WO | WO-2015077721 A | * | 5/2015 | A42B 3/286 |
| WO | WO-2017116174 | * | 7/2017 | A62B 7/10 |

* cited by examiner

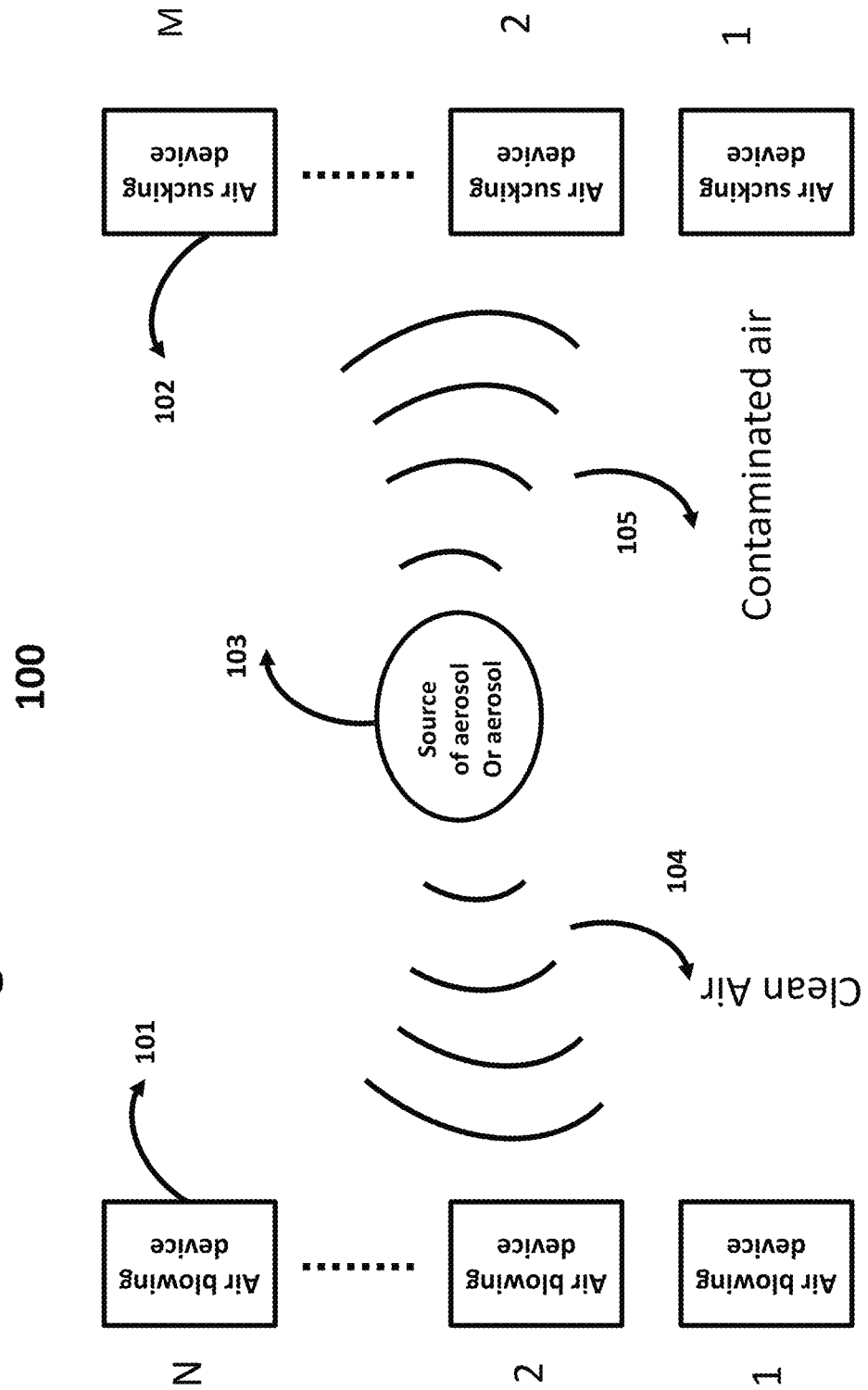

- 127 — Guiding nozzle
- Air sucking device
- 122
- 125 — Contaminated air
- Source of aerosol Or aerosol
- 123
- 124 — Clean Air
- Air blowing device
- 121
- 126

- 137 Guiding nozzle
- Air sucking device
- 132
- 135 Contaminated air
- Source of aerosol Or aerosol — 133
- 134 Contaminated air
- 131
- Air sucking device
- 136

- 152 — Air sucking device
- 150
- 159 — Nozzle
- 155 — Sensor
- 157 — Contaminated air
- 154 — Source of aerosol Or aerosol
- 156 — Clean Air
- 153 — Control processor
- 158
- 151 — Air blowing device

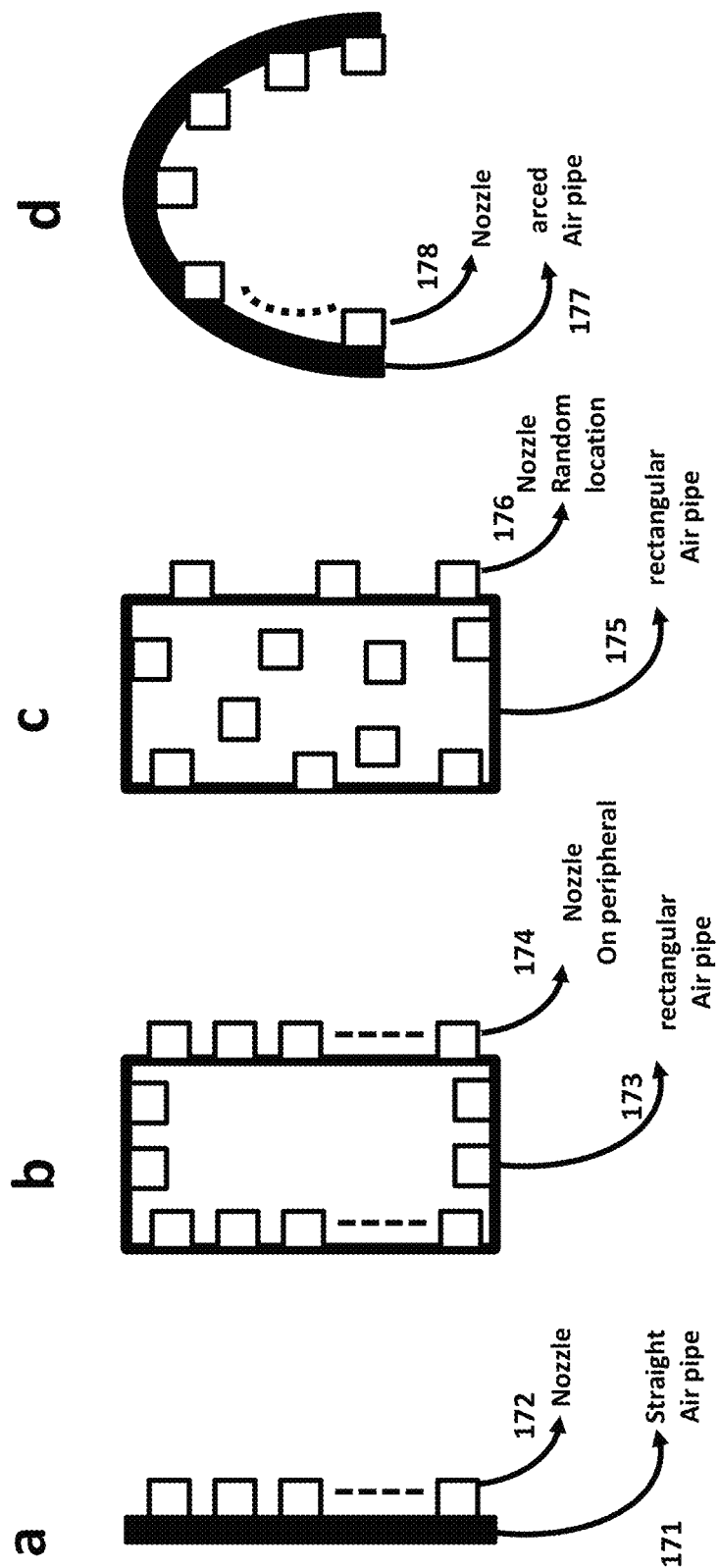

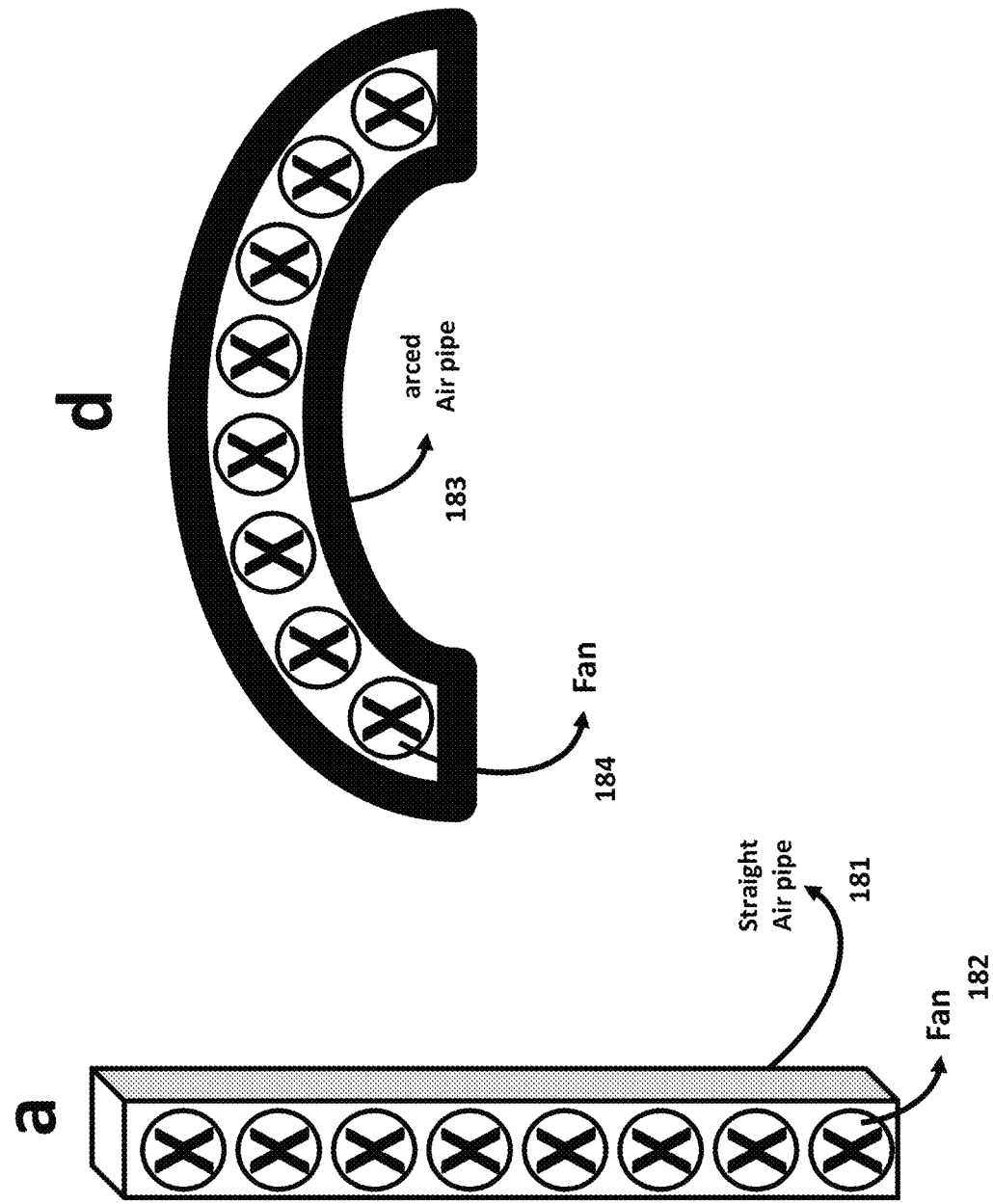

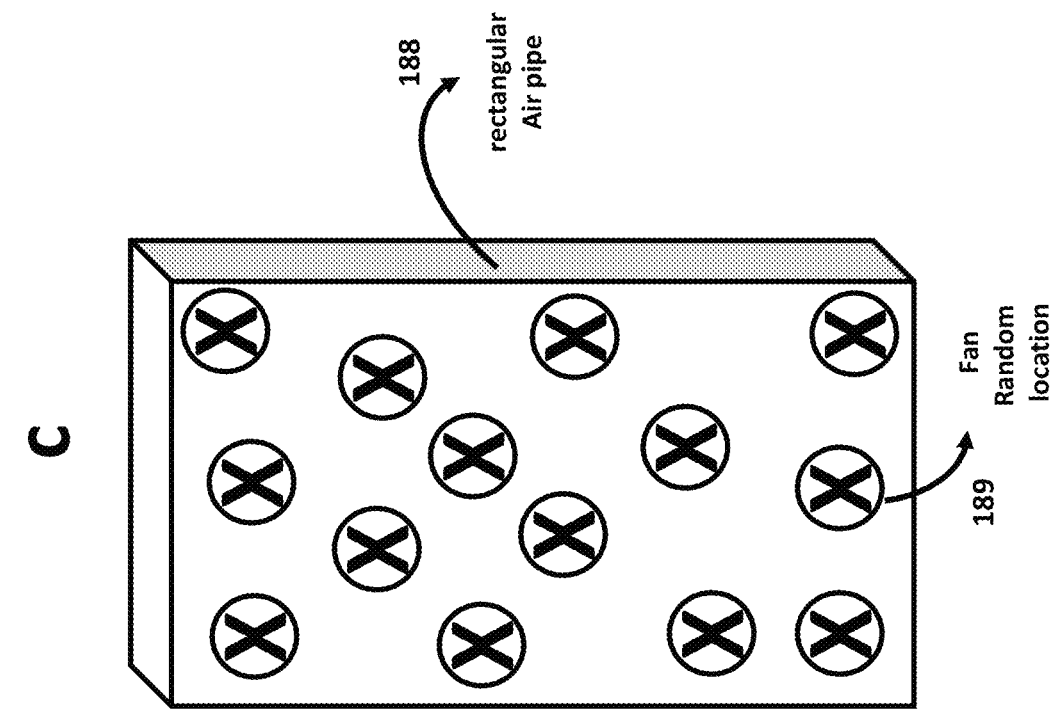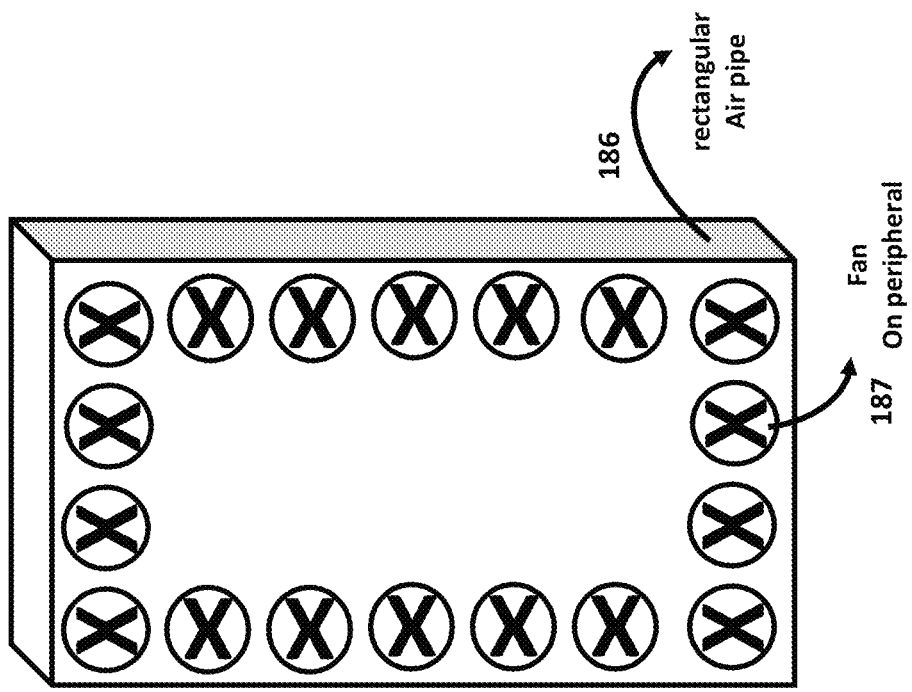
Figure 4C

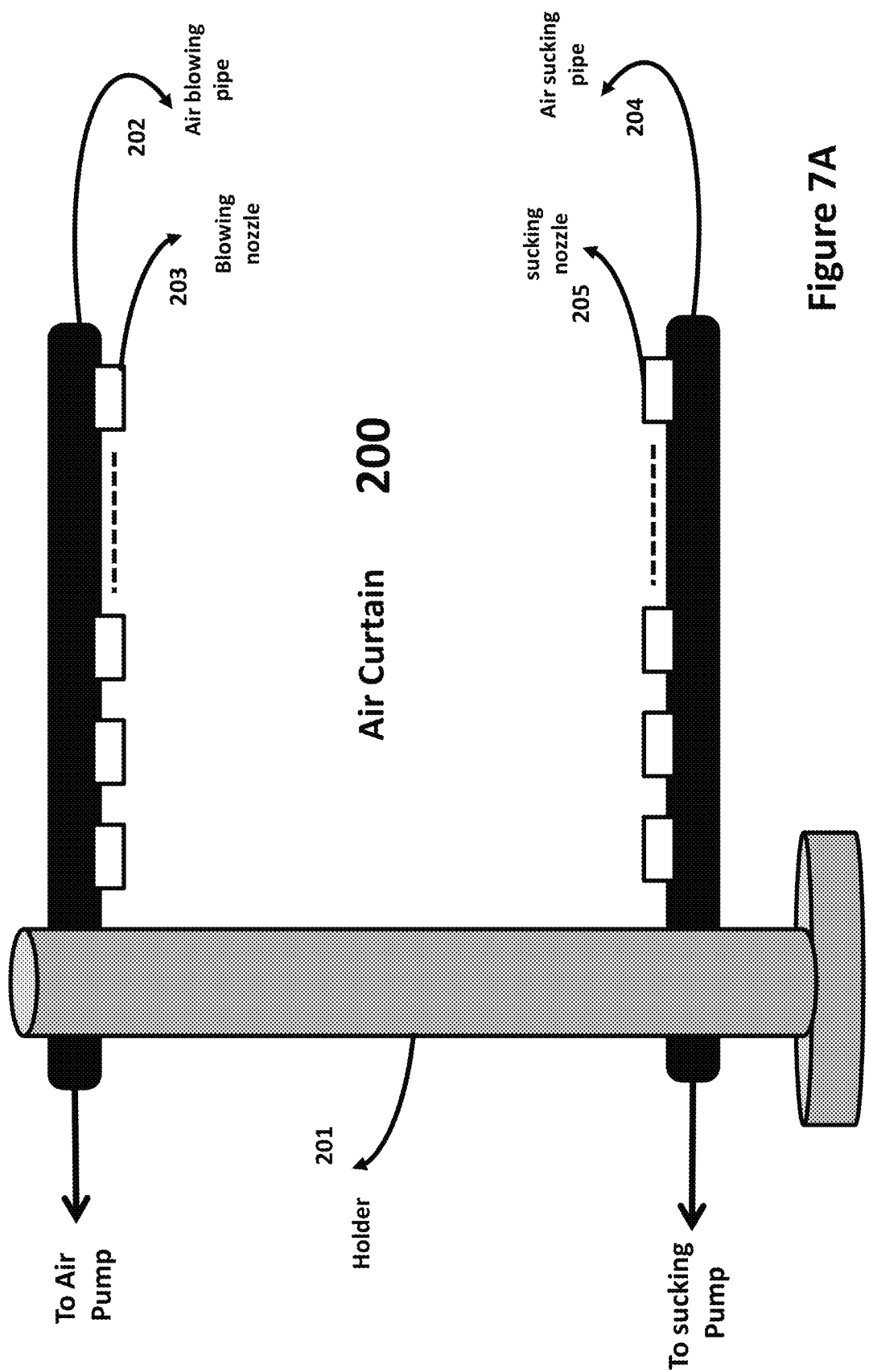

Figure 7H

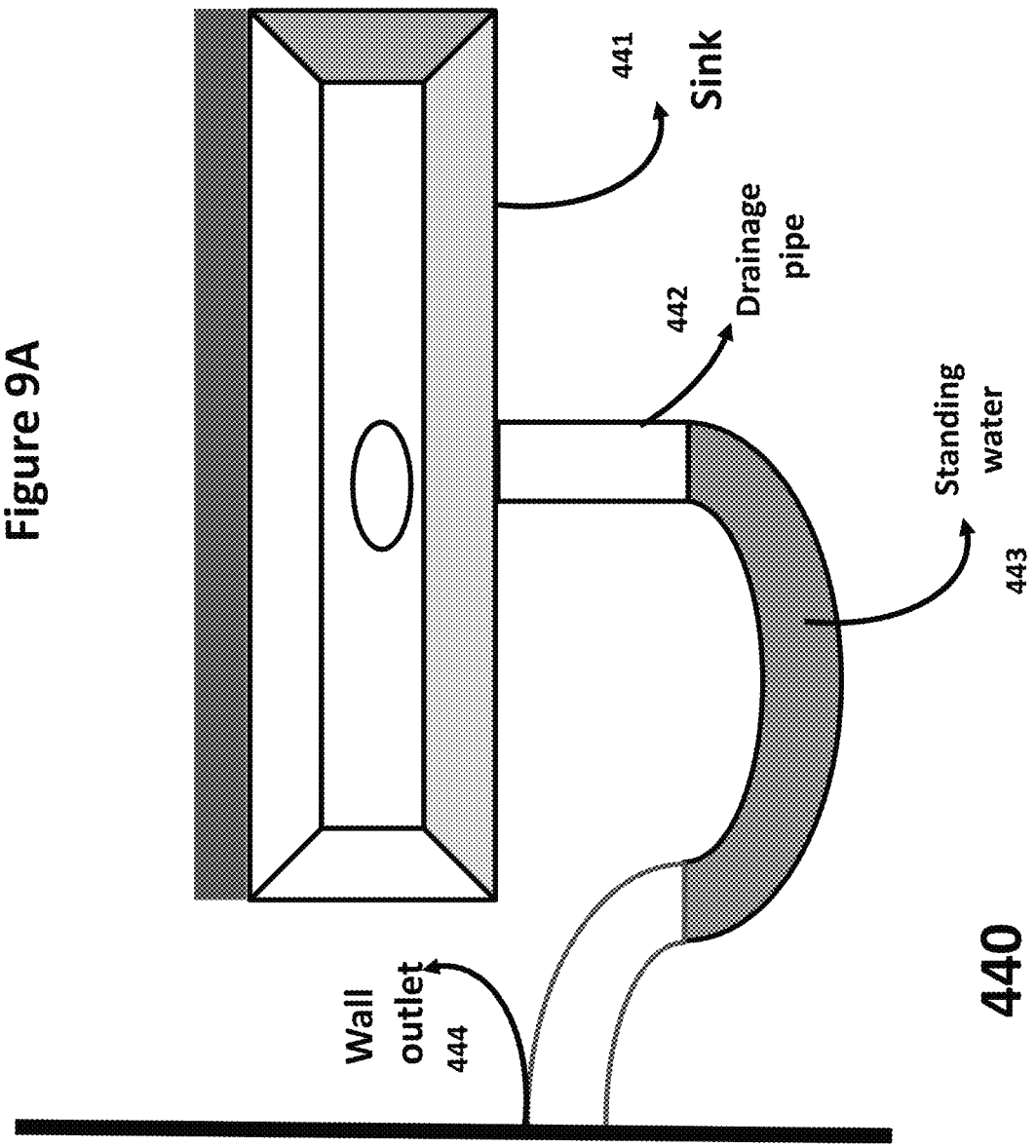

Figure 12B

- Transparent Shield 532
- Through holes 533
- Sucking fan 534
- Aerosol pipe 535
- 530
- 539
- holder 531
- To Power supply 536
- Aerosol filter 537
- 538

Figure 12C

- holder 541
- Sucking fan 544
- Transparent Shield 542
- Aerosol pipe 545
- Through holes 543
- 548
- Power supply 546
- To inlet of Aerosol disposal 547
- Aerosol Transparent Shield 540

Figure 12D

Aerosol Transparent Shield 550 holder 551
Transparent Shield 552
Through holes 553
Sucking fan 554
Aerosol pipe 555
To Power supply 556
To inlet of Aerosol disposal 557

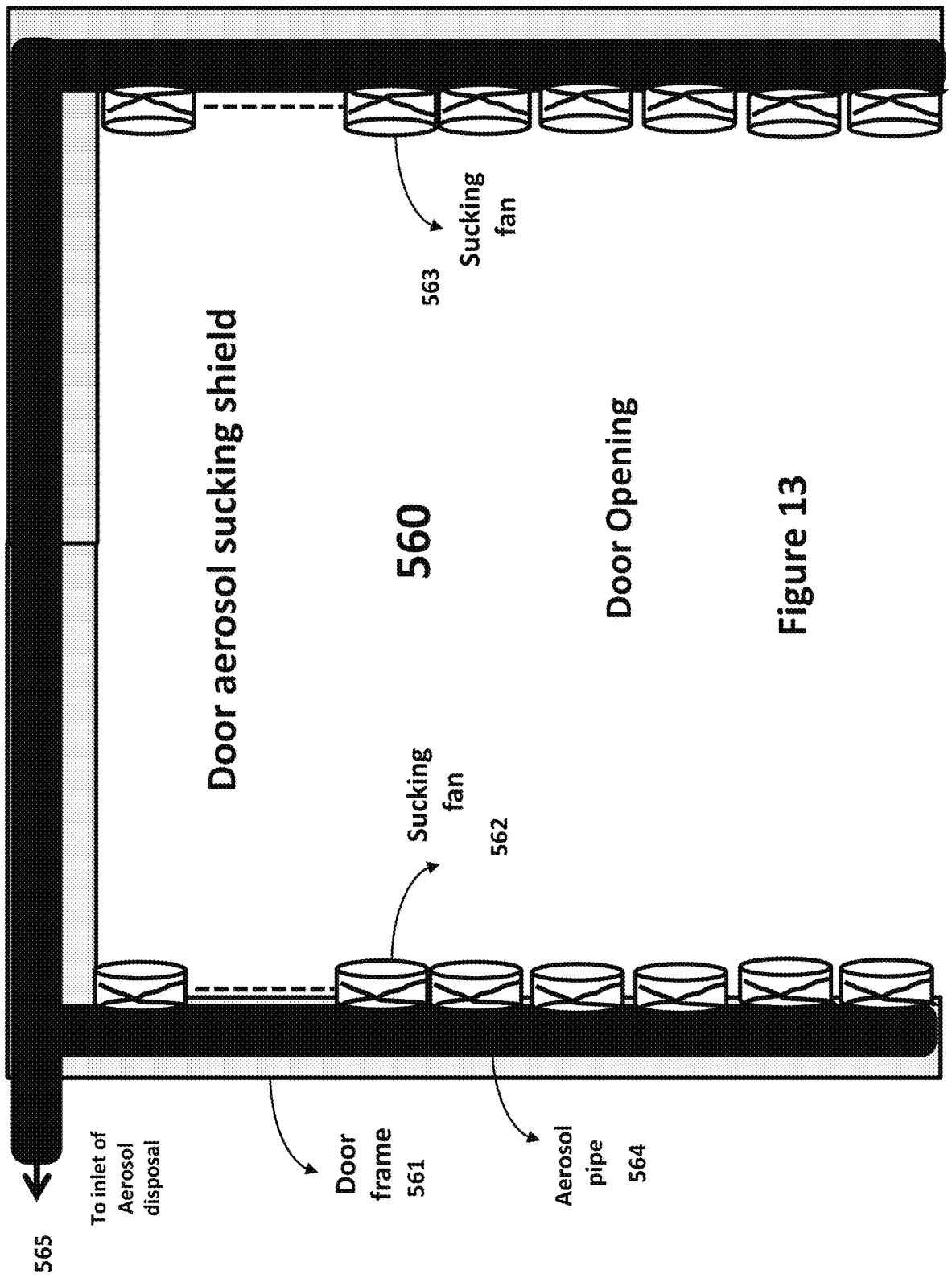

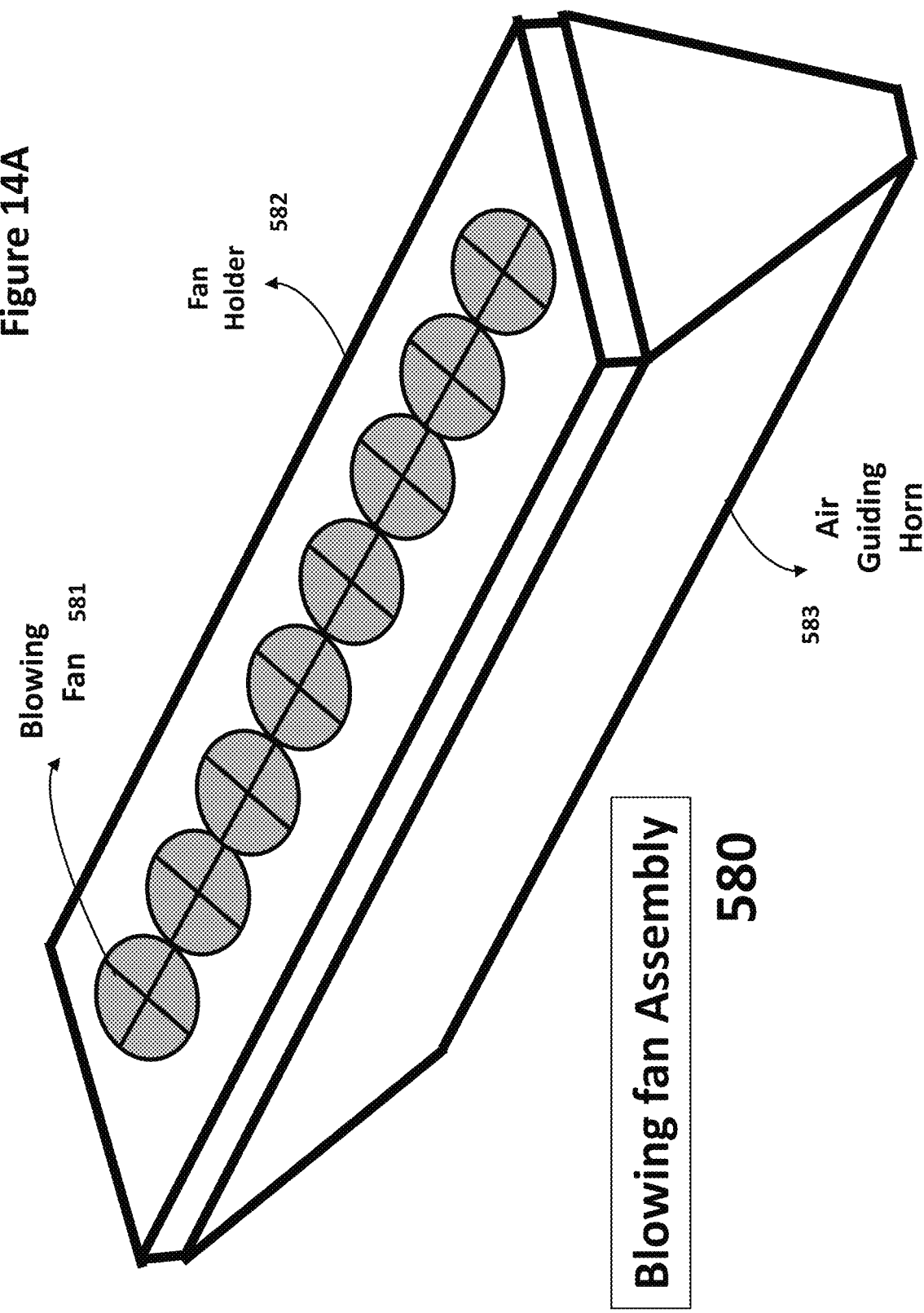

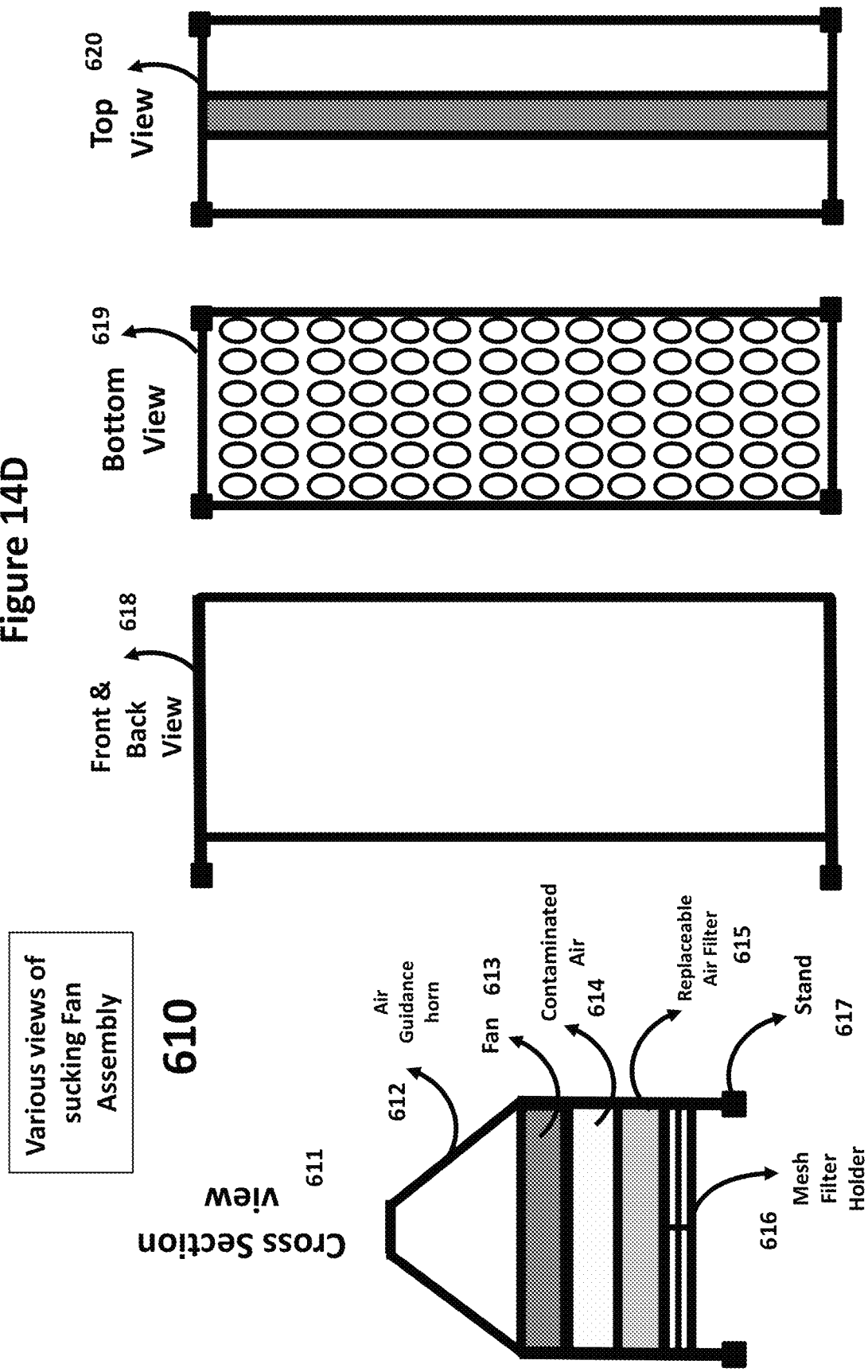

Portable Aerosol Shield 650

Figure 16A

- 654 Sucking fan
- 655 aerosol
- 652 Aerosol pipe And fan holder
- 651 Adjustable holder
- 653 Adjustable Flexible Arm & Aerosol pipe
- 656 Aerosol filter
- 657 To Power supply
- 658

Ceiling Protection Shield 660

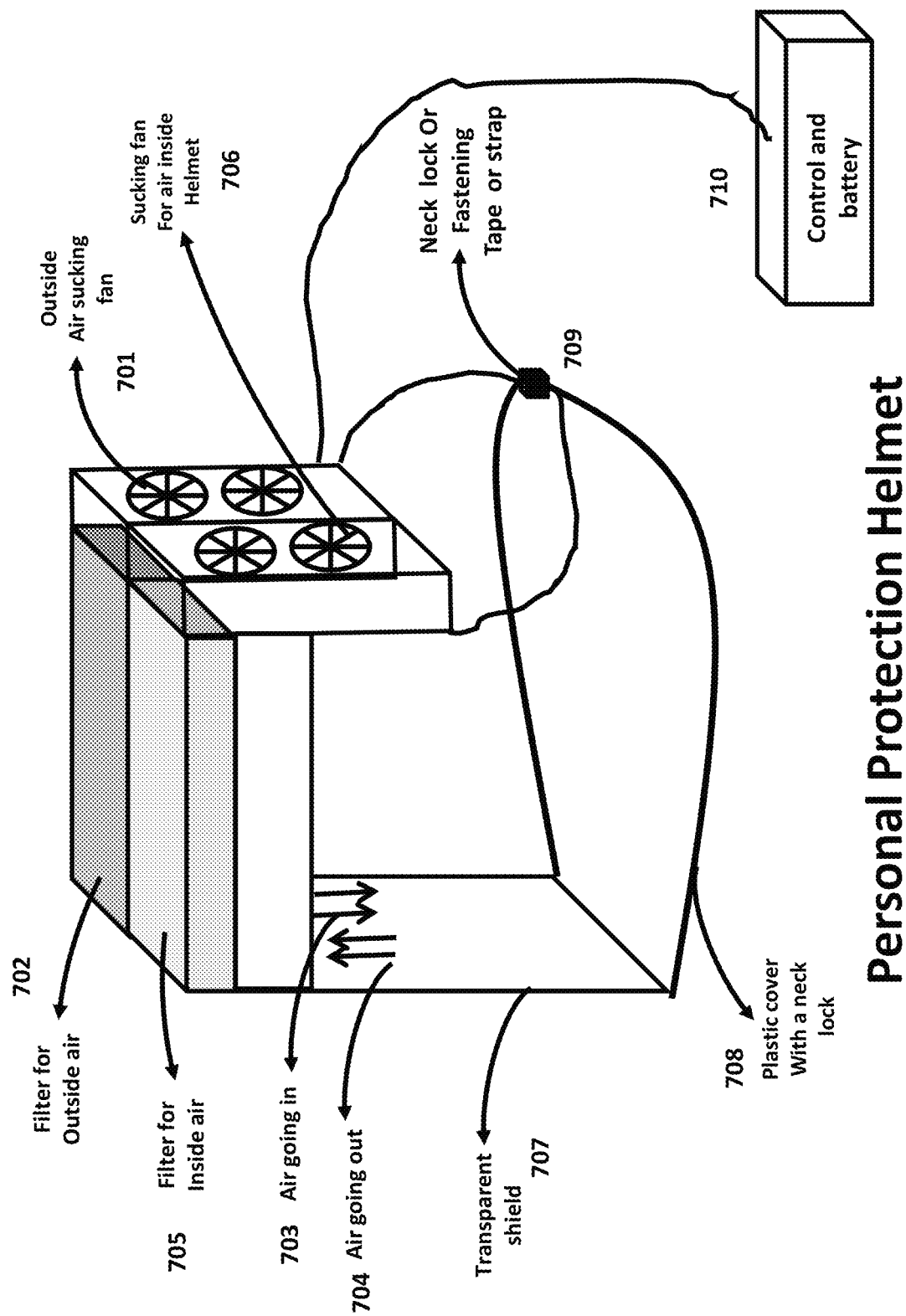

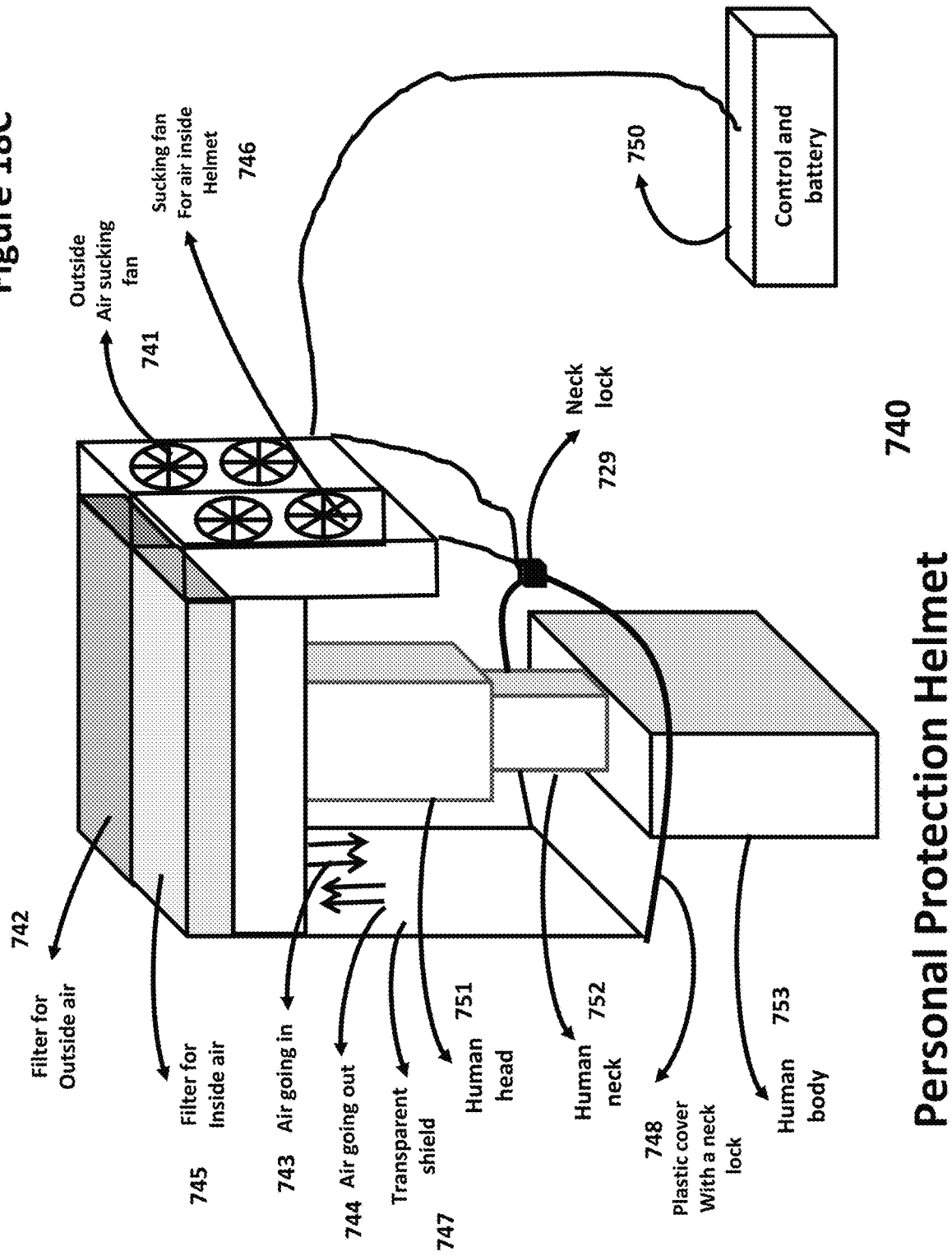

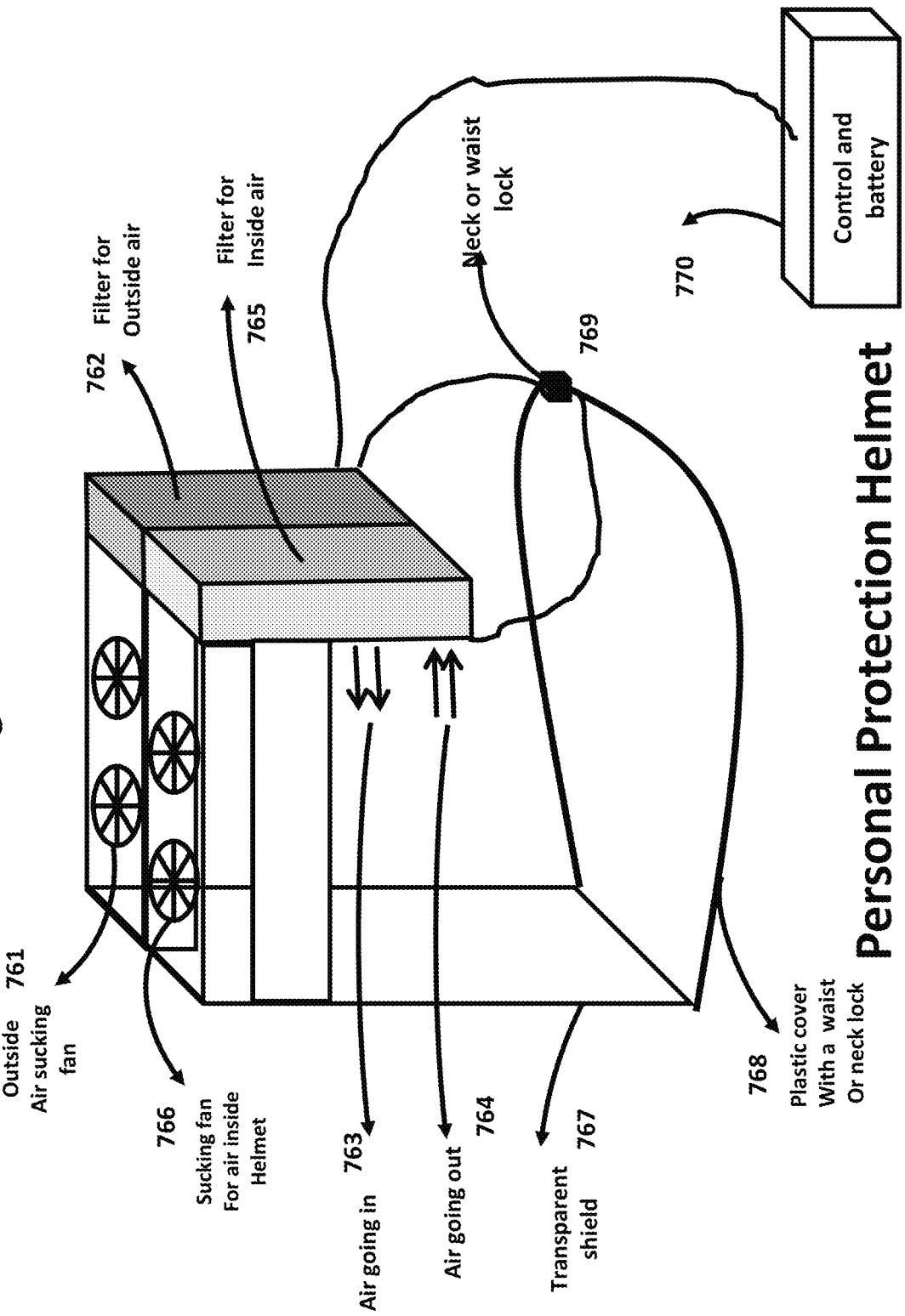

- holder 901
- Transparent Shield 902
- Through holes 903
- Sucking fan 904
- Aerosol pipe 905
- To Power supply 906
- Aerosol filter 907
- 908
- 909
- Aerosol transparent shield 900

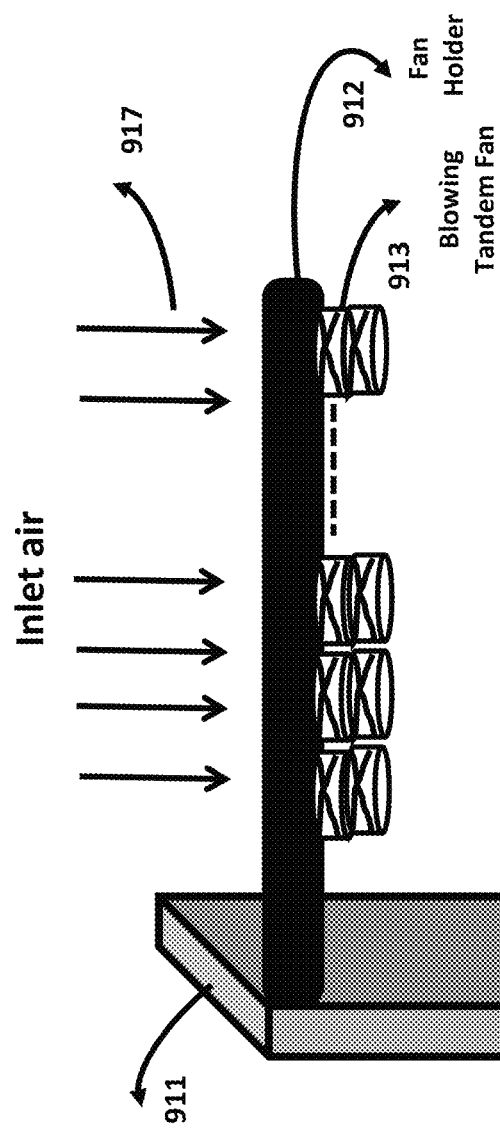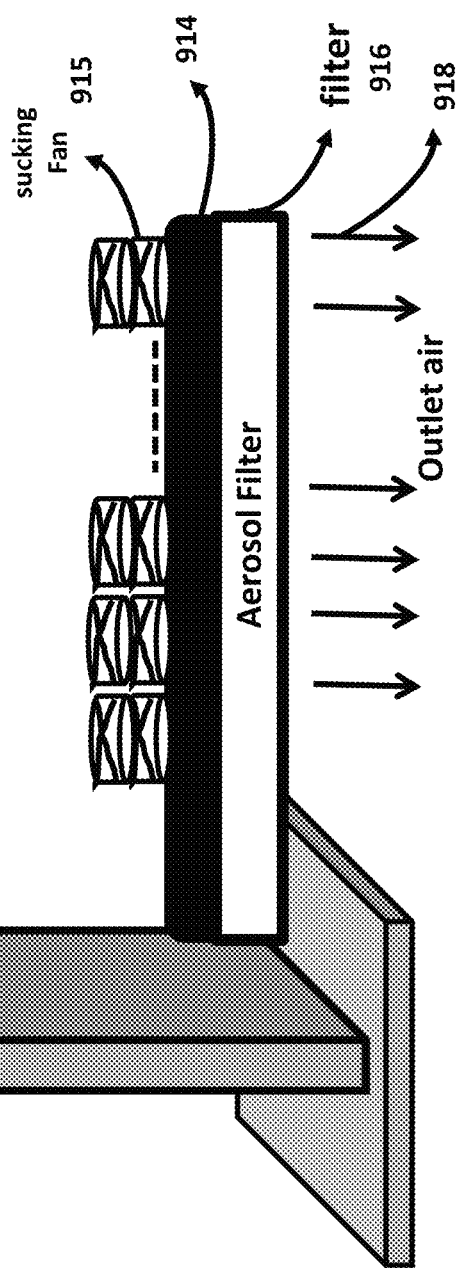
Figure 25

Figure 26

Aerosol Shield 920

- 921
- 922 Fan Holder
- 923 sucking Tandem Fan
- 924 sucking Fan
- 925 filter
- 926 Aerosol Filter
- Outlet air

AEROSOL PROTECTION SYSTEM

The application claims priority to the following related application and included here is as a reference.

Provisional application: U.S. patent application No. 63/015,549 filed Apr. 25, 2020, and entitled "AN AEROSOL PROTECTION SYSTEM."

BACKGROUND

Today, the world community is threatened by the severe acute respiratory syndrome coronavirus 2 (SARS-CoV-2) pandemic. The severity of infection with the virus depends heavily on medical system and health of the infected persons. Recent study shows that the estimated infection fatality ratio (IFR), over all age-groups including those who don't have symptoms, varies between 0.2%-1.6% with an average of 0.66% (Verity et al., 2020). Because these numbers look small and risk of fatality appears acceptable the danger is often marginalized. Considering that the IFR of the seasonal flu is about 0.04-0.1% (Centers for Disease, 2010) or even much lower (Wong et al. 2013) the mortality rate of SARS-CoV-2 appears to be significantly higher than for influenza flu. The numbers for SARS-CoV-2 are quite preliminary and the numbers may drop over time but it is very obvious that the strategy of herd immunization of the population is not an option, due to large number of victims that is not acceptable to any community. Today the best hopes for managing the pandemic is the development of a vaccine. However, it is completely uncertain when an effective and well-tolerated vaccine will be generally available to contain the pandemic. Drugs such as Chloroquine, Remdesivir, Lopinavir and Ritonavir are promising in the fight against the coronavirus disease 2019 (COVID-19). However, even if one of the drugs should prove to be effective, there is no guarantee that the drug can be made available to the world population in sufficient quantities. In addition, it is possible that, despite the use of drugs, going through a severe course of disease can lead to lifelong neuropsychiatric sequelae (Troyer et al., 2020 and Zandifar & Badrfam, 2020) or cause other diseases (Ackermann et al., 2020 and Varga et al., 2020). Containing the pandemic is therefore the only viable way to stop the spread of the virus. But containing the pandemic is a difficult task as about 44% of SARS-CoV-2 infections are caused by people with a pre-symptomatic and asymptomatic course of infection (He et al., 2020). Therefore, due to the absence of symptoms, many people do not know that they are infected and are spreading the virus and these people make it very difficult to trace the transmission chains. Furthermore, about 10% of infected people are responsible for 80% of infections (Kupferschmidt, 2020 and Lloyd-Smith et al., 2005). People who have many social contacts at work or in their private lives and who do not protect themselves and others sufficiently by observing the rules of distance and hygiene, or who consider the risk of the virus to be low, appear to be a serious problem in the actual pandemic.

Between 1990 and 2005 the most common, self-reported, reason for a dentist to miss work was a respiratory infection. Seroprevalence studies demonstrate antibodies to bacteria, fungi, and viruses found in saliva are more common in dentists and increase with experience. Many paid scant attention to dental aerosols, spatter, and splatter until the devastatingly negative impact of the SARS-CoV-2 virus (cause of COVID-19) befell us all. It is thought the SAR-CoV-2 virus is spread primarily through respiratory droplets (i.e. bioaerosols). Airborne transmission from person-to-person over long distances is unlikely. However, the contribution of aerosols, or droplet nuclei, to close proximity transmission is currently uncertain. The virus has been shown to survive in aerosols for hours and on surfaces for days. There are also indications that patients may be able to spread the virus while pre-symptomatic or asymptomatic. These people have been called the 'silent killer' or 'silent spreader' and as such we must assume all individuals are carriers of the SARS-CoV-2 virus. Hence, a new era of universal precaution is upon us, one that addresses the threat or bioaerosols.

The practice of dentistry involves the use of rotary dental and surgical instruments such as handpieces or ultrasonic scalers and air-water syringes. These instruments create a visible spray (spatter) that contains large particle droplets of water, saliva, blood, microorganisms, and other debris. This spatter travels only a short distance and settles quickly, landing on the floor, nearby operatory surfaces, the dentist, the assistant, and the patient. The spray also might contain bioaerosols (i.e. aerosols contaminated with biological material). Surgical masks protect mucous membranes of the mouth and nose from droplet spatter, but they do not provide complete protection against inhalation of airborne infectious agents (bioaerosols).

Most dental procedures have the potential for creating contaminated bioaerosols, spatter, and splatter. An aerosol (aka droplet) is a suspension of extremely fine ($\leq 50$ μm in diameter) airborne particles of liquid, solid, or a combination thereof. Evaporation will decrease the size of the droplet to less than 10 μm. These are called droplet nuclei and they have an enhanced ability to remain afloat in the air, by-pass barriers, and enter respiratory passages. Aerosols and droplet nuclei are considered primary infection vectors for the coronavirus.

Spatter consists of larger airborne particles (>50 μm in diameter). They do not remain airborne for long. They behave in a ballistic manner, arcing quickly downwards as the kinetic energy that projected them dissipates. If enough spatter droplets unite they will form splatter which is, by definition, visible to the naked eye.

Viruses are small (0.02 μm to 0.4 μm) in comparison to bacteria (0.2 μm to 10 μm). Oral bacteria have been detected up to two meters from the procedural field. Because of its smaller size, the contamination potential of a bioaerosol is believed to be many folds higher than that of spatter. Even in the absence of water or a visible spatter 'cloud', dental procedures produce aerosols contaminated with bacteria, viruses, fungi, protozoa, parasites, blood products, soft and hard tissue remnants, tooth debris, and dental material (fragments). The main sources for these contaminants are:

The patient: saliva, blood, soft and hard oral tissue, gingival, orinasal and pharyngeal secretions, plaque, caries, pulp, and tooth structure.

Dental material fragments from a bur, rubber dam, filling material, cement, gutta-percha, post, etch, bond, haeme-control products, topical gel, etc. . . .

Dental water unit line (microflora).

Forced air (ventilation system, fans, handpieces, and syringes), recycling of potentially contaminated air.

Instruments contaminated during treatment and exposed to forced air.

Not only is the composition of a droplet unique for each person, on any particular day, but it also varies depending on the treatment site and procedures performed. During treatment, the highest concentration of airborne contaminants is within 30 cm to 90 cm of the mouth. This is the domain of the dentist and assistant who will therefore need the highest level of protection. Universal precaution dictates our protective measures need to be effective against the most virulent 'cloud' of contaminated droplets. Additional measures should be considered for protecting other patients and staff beyond the confines of the operatory and for extended periods, including postoperatively. Before the coronavirus pandemic, this may have been a blind spot for dental regulators.

Knowledge of the characteristics of the various carriers of protective protocols will inform the development of effective barrier devices and protective protocols. Currently no data is available regarding the risk of SARS-CoV-2 transmission in a dental setting or if current infection control protocols and barrier equipment are adequate against SARS-CoV-2 or similar viruses.

To date in the United States or Canada, clusters of healthcare workers positive for COVID-19 have been identified in hospitals and long-term care facilities, but none in a dental setting, yet. Nevertheless, the Occupational Safety and Health Administration's Guidance on Preparing Workplaces for COVID-19 places dental professionals in the very high exposure risk category, as their jobs are those with high potential for exposure to known or suspected sources of the virus that causes COVID-19 during specific procedures.

Today understanding the transmission pathways is the key to finding effective measures to block the infection and to reliably protect healthcare workers and the population. Droplet infection is currently assumed to be the main transmission route over short distances (Wang et al., 2020). Since this path of infection is via the air, the rules of distance are effective (Soper, 1919 and Wells et al., 1936). But it is also known that SARS-CoV-2 can remain infectious in aerosols for more than 3 h, at least under laboratory conditions at high humidity (van Doremalen et al., 2020 and Pyankov et al., 2018). It is therefore conceivable that infections can also occur under special conditions over long distances, provided that the local virus concentration reaches the minimum infection dose due to poor air exchange in rooms A significant proportion of the aerosol exhaled by humans has a diameter of less than 10 μm (Johnson et al., 2011) when breathing, speaking, singing and coughing. It is also known that the size and number of droplets increases with the volume of the voice (Asadi et al., 2019; Loudon & Roberts, 1968) and it is known that upper respiratory tract diseases increase the production of aerosol particles (Lee et al., 2019). Water droplets of this size evaporate within a few seconds at normal humidity (Liu et al. 2019 and Rensink, 2004). Droplets with a diameter of 10 μm for instance are evaporated after about 1 s at 50% relative humidity and larger droplets sink quickly to the ground and evaporate (Marin et al., 2016, 2019; Rossi et al., 2019). For this reason it is most important to understand the transmission of the virus over short distances.

Hygiene regulations and social distancing are very effective in blocking short distance infections. During the lockdown, the distance rules can usually be adhered to, but what happens when the actual lockdown is over and the people meet again in a confined space? Then additional effective and efficient protection is essential to stabilize infection rates. Since the viruses are spread by contact and droplet infection, technical devices are required that effectively intervene in the chain of infection and effectively block infection. An effective protection is the respiratory mask as known since 100 years (Soper, 1919).

This patent application discloses an alternative to mask that is an aerosol protection system for various applications in environment. The protection system consists of an adjustable air sucking device in different form factors based on application. The aerosol protection system uses either an air curtain or air shield to prevent the aerosol going from one side of the curtain or shield to the other side.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In one aspect, the aerosol protection system uses an air curtain to block aerosol produced by persons or animals.

In another aspect, the aerosol protection system uses an air blower to push aerosol to an air sucking device to be sucked out of environment.

In one aspect, the aerosol protection system uses an air pump to pump the air to an air blower and a sucking pump connected to sucking device outlet to suck the air.

In one aspect, the air blower uses adjustable nozzles to guide the aerosols towards the sucking device which also uses adjustable nozzles to suck the guided aerosol.

In another aspect, the sucked aerosol is filtered before being released to environment and the filter is a HEPA (high efficiency particulate air) or ULPA (ultra low particulate air) filter that is replaceable after a period of use.

In one aspect, the distance between air blower and air sucking device in air curtain is adjustable depending on application.

In another aspect, the CFM (cubic feet per minute) of air blown by air blower and sucking power of sucking device is adjustable through air pump and air sucking pump.

In one aspect, the adjustable nozzles are used by air blower and air sucking device adjust the direction of air curtain.

In another aspect, the adjustable nozzles used by air blower and air sucking devices adjust direction, orientation and CFM of air curtain.

In one aspect, the air blowing device and air sucking device used for an air certain have a straight line shape, a rectangle peripheral shape, an elliptic peripheral shape, a circle peripheral shape or an arbitrary peripheral shape.

In another aspect, the nozzles that control the orientation, air flow CFM and air sucking power are on the peripheral of air blowing and air sucking devices.

In another aspect, the air curtain has a rectangular peripheral shape where one side of the rectangle is used for blowing air and the opposite side is used for sucking air.

In one aspect, 3 adjacent sides of rectangle are used for blowing air and one side is used for sucking air or 3 adjacent sides are used for sucking air and one side is used for blowing air.

In another aspect, the air curtain is an aerosol sucking shield and one side, two sides, three sides or all sides of the rectangle is used for sucking air.

In one aspect, the aerosol sucking shield has 3 to six sides and one or more sides are used for sucking air.

In another aspect, the air curtain has a circular or elliptic shape and the entire peripheral is used to blow air or suck air.

In another aspect, the air curtain has an arbitrary shape and part or all the peripheral is used to blow or suck air.

In one aspect, the air blowing device has a rectangular shape and two parallel sides of rectangle are used for air blowing where one side is the main air blowing side and the second side is a redundant air blowing side to introduce a second air curtain that is used to block any aerosol that passes the main air curtain.

In one aspect, the redundant air blowing side is used when the main air blowing side malfunctions.

In another aspect, the air curtain has "n" air blowing curtains to create "n−1" redundancy.

In one aspect, a controller is used to control the CFM of an air blower or sucking power of a sucking device, where the controller through air flow sensors obtains information data and use the data to control air blower or air sucking device.

In another aspect, the air curtain uses air fans for blowing and sucking air.

In one aspect, the fan's CFM and air sucking power is adjustable by adjusting the speed of the fan which is done by changing the DC (direct current) or AC (alternate current) voltage used by the fan.

In another aspect, two or more fans are stack on top of each other to obtain higher CFM and sucking power.

In one aspect, air curtain uses blowing and sucking fans to produce various air curtain shapes.

In another aspect, air curtain uses single fan for sucking the air and two or more tandem fans for blowing the air.

In one aspect, air curtain uses single fan for blowing the air and two or more tandem fans for sucking the air.

In one aspect, air curtain uses blowing fans at the top and right edge and sucking fan at the bottom and left edge of the curtain.

In another aspect, a manual knob is used to adjust the CFM of air blowing fans and sucking power of air sucking fans by changing an applied voltage to each individual fan to achieve better blocking for an air curtain.

In another aspect, air curtain is an aerosol sucking shield when it only sucks aerosol.

In one aspect, the aerosol sucking shield sucks any aerosol that try to pass through the shield and sucking elements are fans that suck the aerosol and through a pipe send them to a filter or an aerosol disposal.

In another aspect, aerosol sucking shield has a rectangular shape and uses sucking fans at any side of rectangle, and the fan is single or two or more fans in tandem.

In one aspect, aerosol sucking shield uses a mix of single fan and tandem fans.

In another aspect, aerosol sucking shield used two shorter aerosol sucking shield on top of each other and each aerosol sucking shields uses sucking fan at the top or bottom of the shield.

In another aspect, the aerosol shield is a transparent plastic or glass shields with a cluster of through holes for audio voice passage.

In one aspect, above the cluster of through holes for audio voice a sucking fan is used to block any aerosol that passes the shield.

In another aspect, the sucking fan is at either side of cluster of through holes, above, below, left side or right side of the cluster.

In another aspect, the shield has multiple cluster of through holes on a horizontal line at different location where it is used and above or below each cluster a sucking fan is used to block passage of aerosols.

In one aspect, an aerosol transparent shield is self contain and portable and has an aerosol filter attached to a holder that holds the transparent shield and takes the contaminated air from the aerosol pipe attached to the sucking fan next to the cluster of through holes and releases clean air.

In another aspect, an aerosol transparent shield uses a holder at two or three sides and the holder holds left, top and right edge of the aerosol transparent shield.

In one aspect, an aerosol transparent shield uses sucking fans that are attached to an aerosol pipe at all four sides (left, above, right, and bottom) of a cluster of through holes used by the aerosol transparent shield.

In another aspect, an aerosol transparent shield has a gap between the transparent shield and the surface holding the aerosol transparent shield.

In one aspect, the gap between the transparent shield and the surface holding it is used for passing materials from one side of the shield to the other side of shield.

In another aspect, in order to stop any aerosol penetrating from one side of transparent shield to the other side through the gap between the transparent shield and the surface, a plastic (or similar material) tape attached to transparent shield that moves to front and back is used.

In another aspect, the aerosol sucking shield has two attached compartments each acts independently and uses sucking fans on one side of each compartment to block aerosol.

In one aspect, the aerosol curtain uses two or three sides of a rectangle to block any aerosol from exiting or entering a room by using 3 sides of a door frame to install sucking fans or nozzles.

In one aspect, the aerosol disposal is a sewage inlet or drainage pipe of a sink.

In another aspect, when a sink's drainage pipe used for disposing the aerosol the inlet to the drainage pipe is after the standing water.

In one aspect, a rectangular horn is used to guide an air blowing device output and control an air curtain thickness and the speed and force of the air that lives the horn.

In another aspect, the rectangular air guiding horn is used for a sucking device to control the sucking power in direction of an air curtain.

In one aspect, the guiding horn acts similar to a horn antenna and focus the blown air to the exit of the horn which is narrower and similarly focus the power of sucking to the narrow part of the horn.

In one aspect, the rectangular horn holds the fans at one side and blow or suck air from the opposite side of the horn that is narrower and the width of opening depends how narrow the air curtain is.

In another aspect, the air sucking assembly consists of horn, fan, aerosol filter and the filter holder which is also used as outlet for filtered air.

In one aspect, a rectangular shaped aerosol sucking device covers a parson face and sucks the entire aerosol released from mouth of the person.

In one aspect, an elliptical shaped aerosol sucking device covers a parson face and sucks the entire aerosol released from mouth of the person.

In another aspect, both rectangular and elliptical aerosol sucking devices use sucking fans that are attached to an aerosol disposal pipe for carrying the aerosol to an aerosol inlet.

In one aspect, the inner surface of both rectangular and elliptical aerosol sucking devices is a transparent plastic or glass.

In another aspect, both rectangular and elliptical aerosol sucking devices are covered by a flexible transparent material that resembles a tent with a ceiling that has sucking fans.

In one aspect, the sucking device is a circular pipe or a six side pipe holding sucking fans on its peripheral.

In another aspect, the rectangular, circular, or elliptic sucking device uses a flexible arm that holds an aerosol pipe connected to sucking device for carrying the aerosol.

In one embodiment, a portable aerosol shield uses a rectangular, circular, or elliptic sucking device that connects to a holding pole with an attached aerosol filter by a flexible arm that facilitate the aerosol pipe to connect to inlet of aerosol filter.

In one aspect, both rectangular and elliptical aerosol sucking devices with their aerosol disposal pipe through a flexible arm are connected to ceiling of a room.

In one aspect, both rectangular and elliptical aerosol sucking devices with their aerosol disposal pipe through a flexible arm are connected to wall of a room.

In one aspect, both rectangular and elliptical aerosol sucking devices with their aerosol disposal pipe through a flexible arm are connected to a patient's bed.

In another aspect, when the rectangular and elliptical aerosol sucking devices with their aerosol disposal pipe are connected to a room ceiling or wall the disposal pipe is extended to connect to an external aerosol filter, drainage of a sink, or inlet of a sewage.

In another aspect, when the rectangular and elliptical aerosol sucking devices with their aerosol disposal pipe are connected to a patient's bed and bed is not stationary then the disposal pipe is connected to an aerosol filter that resides underneath the bed.

In one embodiment, hospital medical staffs use a personal protection helmet to protect themselves, other medical staff, patients, and visitor.

In another aspect, the personal protection helmet covers the entire head of the person wearing it and is knotted behind the neck of the person with no opening for entering and exiting air.

In one aspect, the front part or personal protection helmet is a transparent shield that can be glass or plastic.

In another aspect, the top and back of the personal protection helmet comprises of two compartments, one for guiding the air towards the mouth of the person wearing the helmet and the other compartment for guiding the air released from mouth to the environment.

In one aspect, the inlet compartment consists of a sucking fan and an aerosol filter, where the sucking fan sucks the air from environment force it through the aerosol filter and release clean air towards the mouth.

In one aspect, the outlet compartment consists of a sucking fan and an aerosol filter, and sucking fan sucks the air released from mouth of the person wearing the helmet through the aerosol filter and releases clean air to the environment.

In one aspect, the aerosol filter uses a HEPA or ULPA filter in both compartments of the helmet.

In one aspect, the outlet compartment consists of a sucking fan only and the fan sucks the air from mouth through an outlet air duct and releases it to environment.

In one aspect, the inlet compartment consists of a sucking fan only and the fan sucks the clean air from environment through an inlet air duct and releases the clean air in the interior of the helmet.

In one aspect, the air inside the helmet is confined by a flexible plastic that is attached to the sucking fans, aerosol filters and front shield assembly and is knotted behind the neck of the person wearing the helmet without any air inside helmet being able to leak to the environment and any air from environment penetrate the interior of the helmet.

In one aspect, the plastic cover is a jacket connected to sucking fans, aerosol filter and transparent shield assembly.

In another aspect, the jacket uses a front zipper, wrist straps, and waist strap to totally isolate the interior of the helmet from environment and prevent any air leaks out to the environment and any air from environment leaks inside the helmet interior.

In one aspect, the plastic cover is a hazmat suit with no head cap connected to sucking fans, aerosol filter and transparent shield assembly.

In one aspect, the hazmat suit uses a front zipper, and wrist straps to totally isolate the interior of the helmet from environment and prevent any air leaks out to the environment and any air from environment leaks inside the helmet interior.

In one aspect, the personal protection helmet is personal protection equipment (PPE) that is used in transportation vehicles such as airplane, train, taxi, truck, and personal vehicles.

In one aspect, a PPE is attached to the ceiling above a seat in a transportation vehicle.

In another aspect, a PPE is attached to the head rest above a seat in a transportation vehicle.

In one aspect, a PPE is attached to the arm rest of a seat in a transportation vehicle.

In another aspect, a PPE is installed underneath a seat or at the back of front seat in a transportation vehicle.

In one aspect, a PPE is powered by a USB cable from a USB outlet near a seat in a transportation vehicle.

In another aspect, the PPE uses the power cable to carry information data collected from various sensors attached to the PPE to a controller.

In one aspect, the controller monitors the operation of PPE and makes action if the performance of the PPE is not according the acceptable thresholds.

In one aspect, the controller configures the operation of sensors used in PPE.

In one aspect, the air curtain is used in dentist operatory room to shield the dentist and dentist assistant from patient aerosol.

In another aspect, an aerosol shield is used in dentist operatory room to shield the dentist and dentist assistant from patient aerosol and the aerosol shield is a sucking device that uses sucking fans on the peripheral of an elliptic aerosol pipe, a circular aerosol pipe, or a rectangular aerosol pipe.

In one aspect, the aerosol shield is used in dentist operatory room is covered with a flexible transparent plastic or other material that dentist and assistant dentist clearly can see the patient's mouth through it.

In another aspect, the flexible transparent cover over the rectangular, circular or elliptical shield has provision for dentist and assistant dentist hand in form of access holes or access sleeves.

In another aspect, the elliptical, circular, or rectangular aerosol shield has a flexible arm that is connected to the light pole, the wall or the ceiling of the operatory room and can be moved around the face of the patient.

In one aspect, the flex arm is connected to a light pole in the dentist operatory room or connected to the ceiling or wall in dentist operatory room.

In one aspect, the aerosol pipe as a part of aerosol shield is also flexible and moves with the flexible arm.

In one aspect, the aerosol pipe for elliptical, circular, and rectangular sucking shields is connected to an aerosol filter which is a HEPA, ULPA, or UVC (ultraviolet light) filter.

In one aspect, the aerosol pipe for elliptical, circular, or rectangular sucking shield is connected to an aerosol inlet of the sink used in the operatory room.

In one aspect, the aerosol pipe for elliptical, circular, or rectangular sucking shield is connected to sewage inlet in the operatory room or outside operatory room.

BRIEF DESCRIPTION OF THE DRAWINGS

FIGS. 1A and 1B depict a generic aerosol protection system for environment.

FIGS. 2A through 2C depict an aerosol protection system with adjustable guiding nozzles.

FIGS. 3A and 3B depict an aerosol protection system with a controller to adjust nozzles.

FIGS. 4A through 4C depict a structure for air blowing and air sucking devices.

FIGS. 7A through 7I depict various air curtain architectures.

FIGS. 9A and 9B show aerosol disposal inlet sink.

FIGS. 12A through 12D illustrate various transparent shields with audio through holes.

FIG. 13 shows a door with aerosol sucking shield.

FIGS. 14A through 14D depict air blowing and air sucking devices assembly.

FIGS. 16A through 16C illustrate aerosol sucking device supported with a flexible arm or a holder.

FIGS. 18A through 18H depict structure of an aerosol protection helmet and personal protection equipment.

FIG. 24 illustrates a transparent shield with audio through holes that has holder at three edges.

FIG. 25 depicts an air curtain using air blowing surface and air sucking surface spaced by a distance.

FIG. 26 depicts an aerosol shield using two air sucking surfaces spaced by a distance.

Figure 3B:
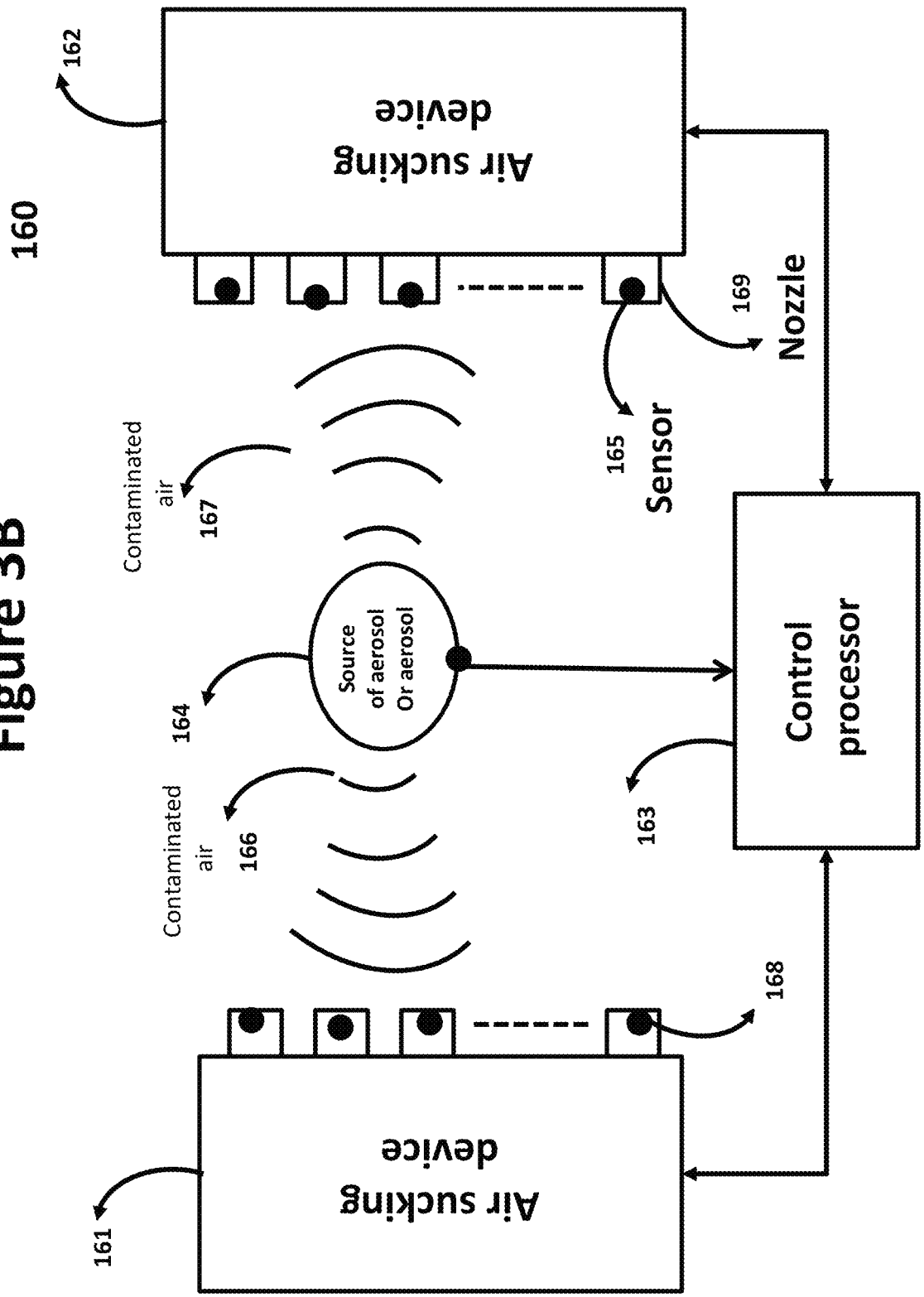

The drawings referred to in this description should be understood as not being drawn to scale except if specifically noted.

DESCRIPTION OF EMBODIMENTS

Reference will now be made in detail to embodiments of the present technology, examples of which are illustrated in the accompanying drawings. While the technology will be described in conjunction with various embodiment(s), it will be understood that they are not intended to limit the present technology to these embodiments. On the contrary, the present technology is intended to cover alternatives, modifications and equivalents, which may be included within the spirit and scope of the various embodiments as defined by the appended claims.

Furthermore, in the following description of embodiments, numerous specific details are set forth in order to provide a thorough understanding of the present technology. However, the present technology may be practiced without these specific details. In other instances, well known methods, procedures, devices, and circuits have not been described in detail as not to unnecessarily obscure aspects of the present embodiments.

Figure 1B:
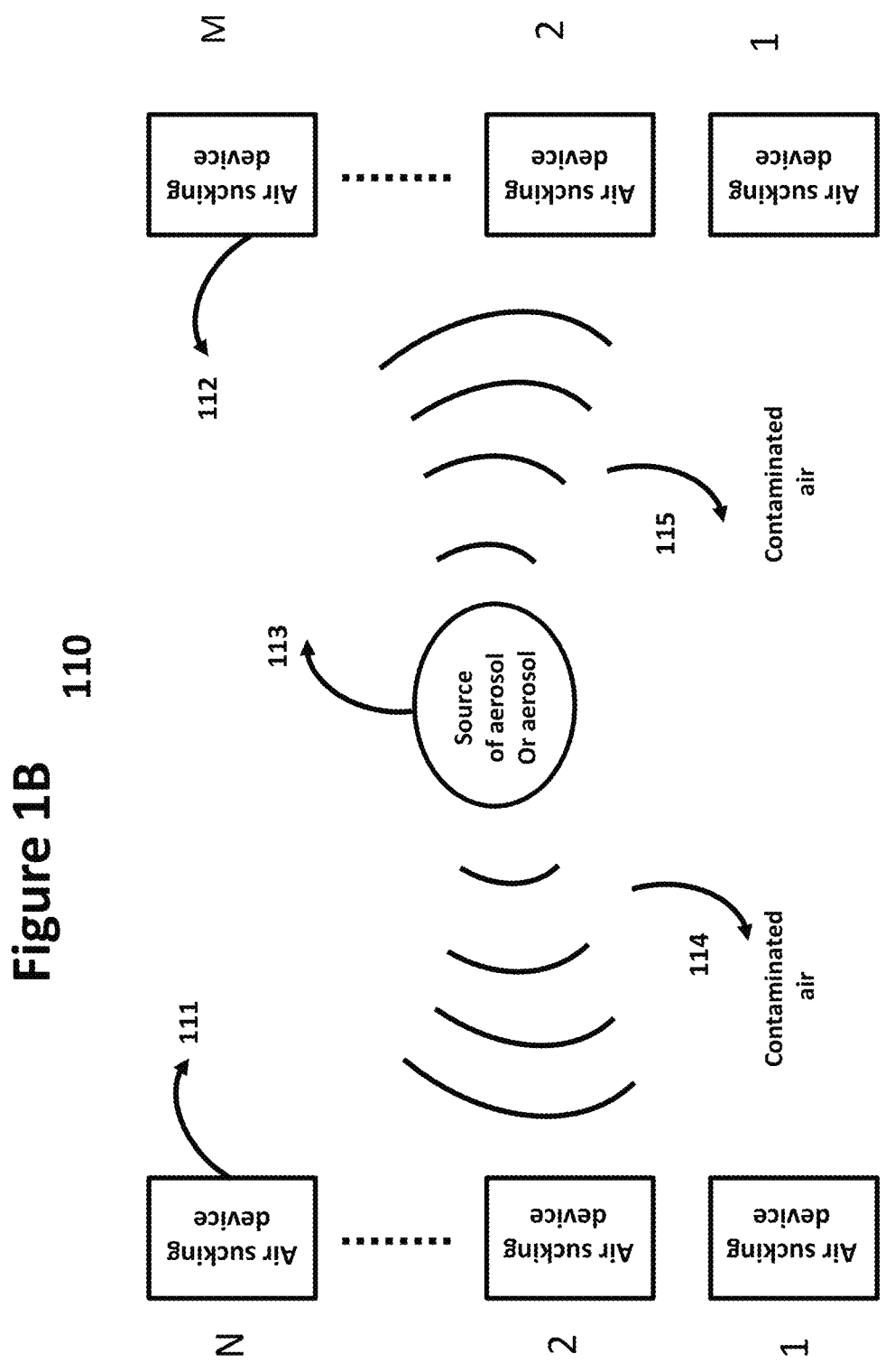

FIG. 1A shows a generic aerosol protection system 100 for environment that can be used for various applications. The function of the aerosol protection system 100 is to clean the environment from aerosols. The aerosol protection system 100 comprises of a number of air blowing devices 101 (1 to N) and a number of air sucking devices 102 (1 to M). The air flow orientation 104 of air blowing devices 101 is towards the source of aerosol 103. The air blowing devices 101 are adjusted to have an air flow pattern 104 with a focal point at the source of aerosol 103.

The function of the air sucking devices 102 is to suck the aerosol-contaminated air. The orientation 105 of the air sucking devices is adjusted to have a focal point at the source of the aerosol 103 in order to maximize the amount of contaminated air sucked from surrounding of source of aerosol, ideally all.

The adjustment of the air blowing devices 101 and air sucking devices 102 can be done manually, semi-manually or automatically. One or more air blowing devices 101 and one or more air sucking devices 102 are used depending on the application.

In one embodiment, aerosol protection system 100 uses air blowing devices and air sucking devices to clean the environment from aerosol produced by an aerosol source.

FIG. 1B shows a generic aerosol protection system 110 for environment that can be used for various applications. The function of the aerosol protection system 110 is to clean the environment from aerosols. The aerosol protection system 110 comprises of a number of air sucking devices 111 (1 to N) on one side of aerosol source 113 and a number of air sucking devices 112 (1 to M) on an opposite side of aerosol 113.

The function of the air sucking devices 111 and 112 is to suck the aerosol-contaminated air. The orientation 104 and 105 of the air sucking devices is adjusted to have a focal point at the source of the aerosol 113 in order to maximize the amount of contaminated air sucked from surrounding of the source of aerosol, ideally all.

The adjustment of the air sucking devices 111 and air sucking devices 112 can be done manually, semi-manually or automatically. One or more air sucking devices 111 and one or more air sucking devices 112 are used depending on the application.

In one embodiment, aerosol protection system 110 uses air sucking devices to clean the environment from aerosol produced by an aerosol source.

FIG. 2A depicts method 120 to adjust the air flow (pattern) 124 of the air blowing device 121 towards aerosol source 123 and sucking pattern 125 of the air sucking device 122 from source of aerosol 123. Both devices have air nozzles for blowing 126 and sucking 127 the air. Air nozzles 126 and 127 are similar to the one used in an airplane, a car, a bus, a train, and other similar applications. The air sucking device 122 works similar to a vacuum cleaner. It sucks the air and the particles in the air from a distance depending on its sucking power.

The operation of the air blowing and air sucking devices has similarity to a dish antenna. Dish antenna has a focal point that is used for receiver Low noise block (LNB) and transmitter feed. The focal point in FIG. 2A is the source of aerosol which can be the mouth of a patient. The air blower device is adjusted through its one or multiple nozzles to focus the air flow towards the mouth of a patient. Therefore, the patient's mouth towards air blowing device acts like an LNB that receives all the air blown from air blowing device. The aerosol coming out of the mouth of the patient is pushed away by the airflow generated by the air blowing device. The function of the air sucking device is to absorb the aerosol-contaminated air from the patient's mouth. In order to do that the location of air sucking device needs to be adjusted. In addition to location of air sucking device its one or multiple nozzles need to be adjusted to absorb the contaminated air with patient's aerosol. The adjustment of location and nozzles of two devices can be done manually, semi-manually or automatically.

Nozzles for both air blowing and air sucking devices 121 and 122 are adjustable. There are two types of adjustments for air blowing device 121. One is adjusting the amount of air flow and the other is the direction of the air flow 124. These two adjustments are performed by the nozzles 126. Nozzles can be bended inward and outward at any point of 360 degree to adjust the direction of air flow 124. The amount of bending depends on the position that is needed to be focused on. The amount of air coming out of each individual nozzle is separately controlled.

Nozzles used by air sucking devices 122 also can be adjusted similar to air blowing device 121 to suck maximum amount of contaminated air from aerosol source 123.

In one embodiment air blowing devices use nozzles to control the amount of air flow as well as direction of air flow and air sucking devices use nozzles to control the sucking power and the direction the air is sucked.

FIG. 2B depicts method 130 to adjust the air sucking pattern 134 of the air sucking device 131 from aerosol source 133 and air sucking pattern 135 of the air sucking device 132 from source of aerosol 133. The sucking devices are located at two sides of aerosol source 133. Both devices have air nozzles 136 and 137 for sucking the air. Air nozzles 136 and 137 are similar to the one used in an airplane, a car, a bus, a train, and other similar applications. The air sucking devices 131 and 132 works similar to a vacuum cleaner. They suck the air and the particles in the air from a distance depending on their sucking power.

Nozzles for both air sucking devices 131 and 132 are adjustable. There are two types of adjustments for air sucking device 131. One is adjusting the air sucking power and the other is the direction of the air sucking pattern 134. These two adjustments are performed by the nozzles 136. Nozzles can be bended inward and outward at any point of 360 degree to adjust the direction of air sucking 134. The amount of bending depends on the position that is needed to be focused on. The amount of air sucked by each individual nozzle is separately controlled.

Nozzles used by air sucking device 132 also can be adjusted similar to air sucking device 131 to suck maximum amount of contaminated air from aerosol source 133.

In one embodiment air sucking devices use nozzles to control the sucking power and the direction the air is sucked.

Figure 2C:
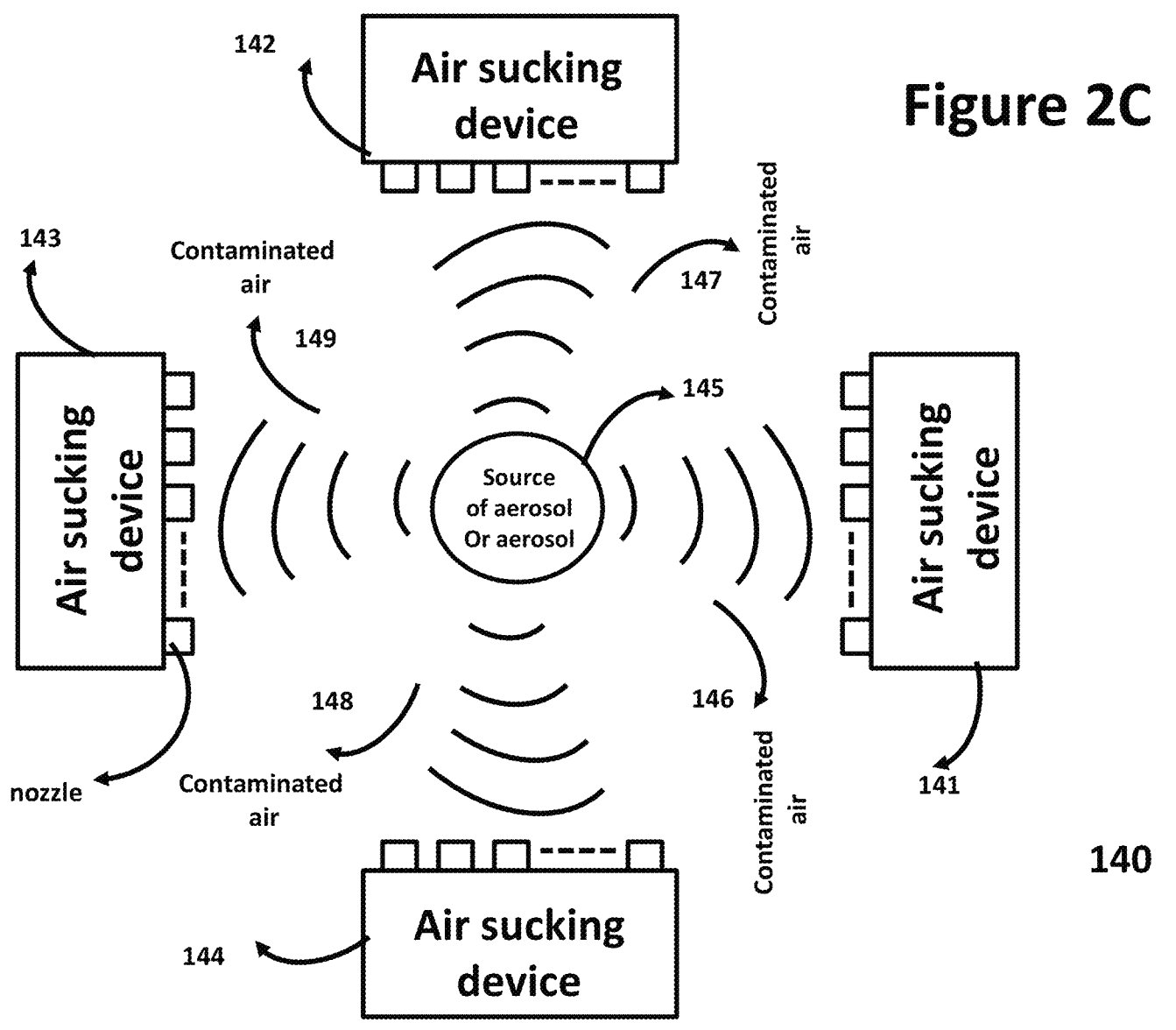

FIG. 2C shows an aerosol protection system 140 for environment. Aerosol protection system 140 uses air sucking devices at 4 sides of an aerosol source. The function of the aerosol protection system 140 is to clean the environment from aerosols. The aerosol protection system 140 comprises of 4 air sucking devices 141, 142, 143, and 144 on each side of aerosol source 145.

The function of the air sucking devices 141, 142, 143, and 144 is to suck the aerosol-contaminated air. The orientation 146, 147, 148, and 149 of the air sucking devices is adjusted to have a focal point at the source of the aerosol 145 in order to maximize the amount of contaminated air sucked from surrounding of the source of aerosol, ideally all.

The adjustment of the air sucking devices 141, 142, 143 and 144 can be done manually, semi-manually or automatically. One or more air sucking devices are used depending on the application.

In one embodiment, aerosol protection system 140 uses 4 air sucking devices at 4 sides of aerosol source to clean the environment from aerosol.

FIG. 3A illustrates an automatic control mechanism 150 for adjusting both air blowing device 151 and air sucking device 152. In order to achieve clean air flow 156 and contaminated air flow 157, both devices 151 and 152 require using sensors. In addition to air blowing device 151 and air sucking device 152 there may be a need for a sensor at the source of the aerosol 154. The sensors 155 and 158 collect specific data and send the data to a control processor 153. Sensors 155 and 158 use wire or wireless techniques to communicate with the control processor 153. The control processor 153 uses the data received from various sensors installed on air blowing device 151, air sucking device 152 and if needed source of aerosol 154 and through an artificial intelligence algorithm decides how to adjust the air blowing device 151 and air sucking device 152 and achieve the air flow patterns 156 and 157. The adjustment through this technique applies to the location and orientation of air blowing device 151 and air socking device 152, amount of air leaving nozzle, orientation and sucking power of nozzle 159.

FIG. 3B shows an automatic control mechanism 160 for adjusting air sucking devices 161 and 162. In order to achieve contaminated air sucking patterns 166 and 167, both devices 161 and 162 require using sensors. In addition to air sucking devices 161 and 162 there may be a need for a sensor at the source of the aerosol 164. The sensors 165 and 168 collect specific data and send the data to a control processor 163. Sensors 165 and 168 use wire or wireless techniques to communicate with the control processor 163. The control processor 163 uses the data received from various sensors installed on air sucking devices 161 and 162 and through an artificial intelligence algorithm decide how to adjust the air sucking devices 161 and 162 to achieve the air sucking patterns 166 and 167. The adjustment through this technique applies to the location and orientation of air socking devices 161 and 162, and sucking power of nozzle 169.

FIG. 4A shows various configurations 170 for air blowing device or air sucking device used by an aerosol protection system. Air blowing device or air sucking device "a" uses a straight air pipe 171 and nozzles 172 along the air pipe 171. The rectangular configuration "b" shows a rectangular air pipe 173 with air blowing nozzles or air sucking nozzles 174 on the peripheral of rectangular air pipe 173.

The rectangular air pipe 173 is similar to rectangular ring surrounding free space. The inside of the rectangular pipe can be free space, a transparent glass, a transparent plastic, or any other material. In other words a rectangular glass or plastic has an air pipe attached to its peripheral which supports air blowing or air sucking nozzles.

The configuration "c" shows a rectangular air container 175 with air sucking and air blowing nozzles 176 randomly mounted on surface of rectangular container 175. The configuration "d" uses an arced air pipe 177 with air sucking or air blowing nozzles 178 attached to the peripheral of the arced air pipe 177.

Configurations "a", "b", "c" and "d" instead of air blowing and air sucking nozzles can use air blowing fans and air sucking fans. In case of air sucking fans configurations "a", "b", and "d" use an air pipes that have air sucking fans attached to them. In case of air blowing fan there is no need for air pipe.

FIG. 4B illustrates fan based configurations 180. Configuration "a" consists of a rectangular straight air pipe 181 with air sucking or air blowing fans 182 attached to the pipe 181. Fan 182 can be configured to blow air received from rectangular air pipe 181 or suck air from environment and release it to rectangular air pipe 181. In case of air blowing fan the pipe is just a holder of the fan and fan gets its air from environment and blows it in certain direction.

Configuration "b" consists of an arc circular air pipe 183 with air sucking or air blowing fans 184 attached to the pipe 183. Fan 184 can be configured to blow air received from arced circular air pipe 183 or suck air from environment and release it to arced circular air pipe 183. Again in case of air blowing fan the pipe is just a holder of the fan and fan gets its air from environment and blows it in certain direction.

In both configurations "a" and "b" the blowing fans or sucking fans are adjusted for blowing CFM, sucking power, direction and orientation of blowing and sucking.

FIG. 4C illustrates fan based configurations 185. Configuration "a" consists of a rectangular pipe 186 with air sucking or air blowing fans 187 attached to the peripheral of rectangular pipe 186. Fan 187 can be configured to blow air received from rectangular pipe 186 or suck air from environment and release it to rectangular pipe 186. In case of air blowing fan the pipe is just a holder of the fan and fan gets its air from environment and blows it in certain direction.

Configuration "b" consists of a rectangular container 188 with air sucking or air blowing fans 189 attached randomly to one surface of rectangular container 188. Fan 189 can be configured to blow air received from rectangular container 188 or suck air from environment and release it to rectangular container 188.

In both configurations "a" and "b" the blowing fans or sucking fans are adjusted for blowing CFM, sucking power, direction and orientation of blowing and sucking.

Figure 5A:
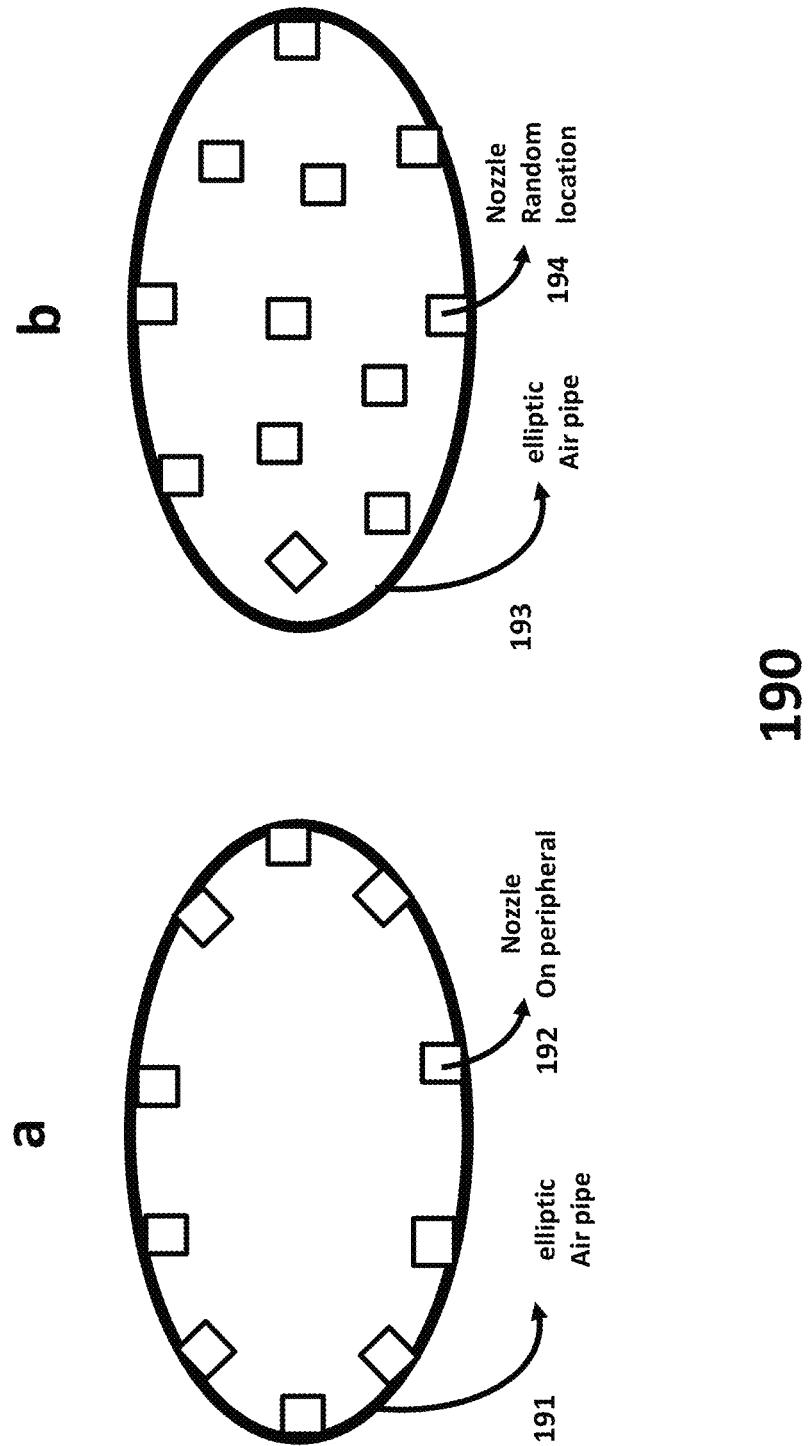
FIGS. 5A and 5B depict an elliptic structure for air sucking devices

FIG. 5A depicts an elliptical configuration 190. Configuration "a" shows an elliptical air pipe 191 that nozzles 192 are located on the peripheral of the air pipe 191. Configuration "b" is an elliptic air container 193 with nozzles 194 located on the surface of elliptic air container 193. The pipe 191 and container 193 can also have a circular shape with the same nozzle arrangement as elliptical pipe and container.

Figure 5B:
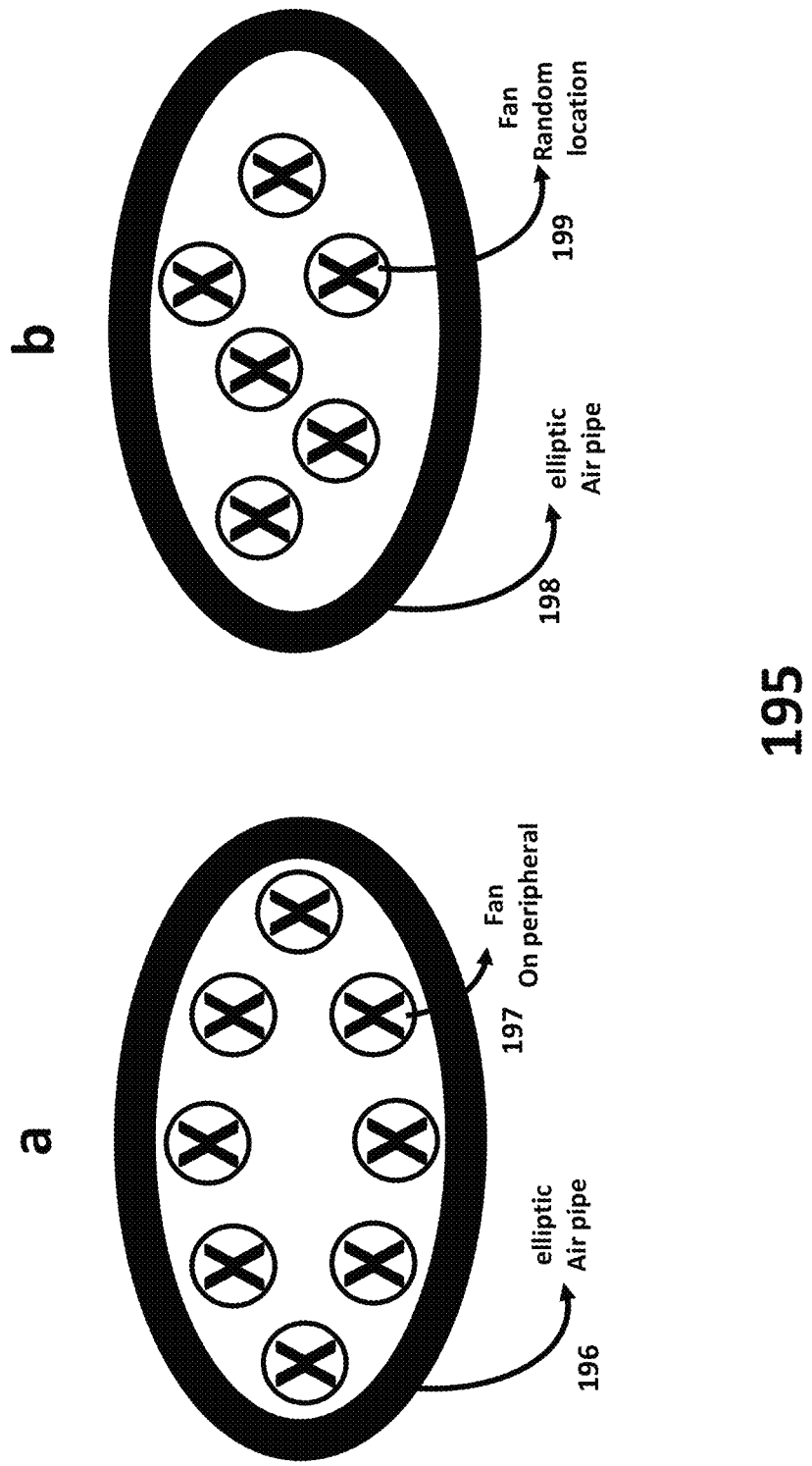

FIG. 5B illustrates fan based configurations 195. Configuration "a" consists of an elliptical pipe 196 with air sucking or air blowing fans 197 attached to the peripheral of elliptical pipe 196. Fan 197 can be configured to blow air received from elliptical pipe 196 or suck air from environment and release it to elliptical pipe 196.

The elliptical air pipe 173 is similar to an elliptical ring surrounding free space. The inside of the elliptical pipe can be free space, a transparent glass, a transparent plastic, or any other material. In other words a elliptical glass or plastic has an air pipe attached to its peripheral which supports air blowing or air sucking nozzles. In case of air blowing fan the air pipe acts as a holder of the air blowing fan. The air pipe 173 can also have a circular configuration.

Configuration "b" consists of an elliptical container 198 with air sucking or air blowing fans 199 attached randomly to the surface of elliptical container 198. Fan 199 can be configured to blow air received from elliptical container 198 or suck air from environment and release it to elliptical container 198. In case of air blowing fan the elliptical container acts as holder of fan and fan gets its air from environment.

In both configurations "a" and "b" the blowing fans or sucking fans are adjusted for blowing CFM, sucking power, direction and orientation of blowing and sucking.

Figure 6:
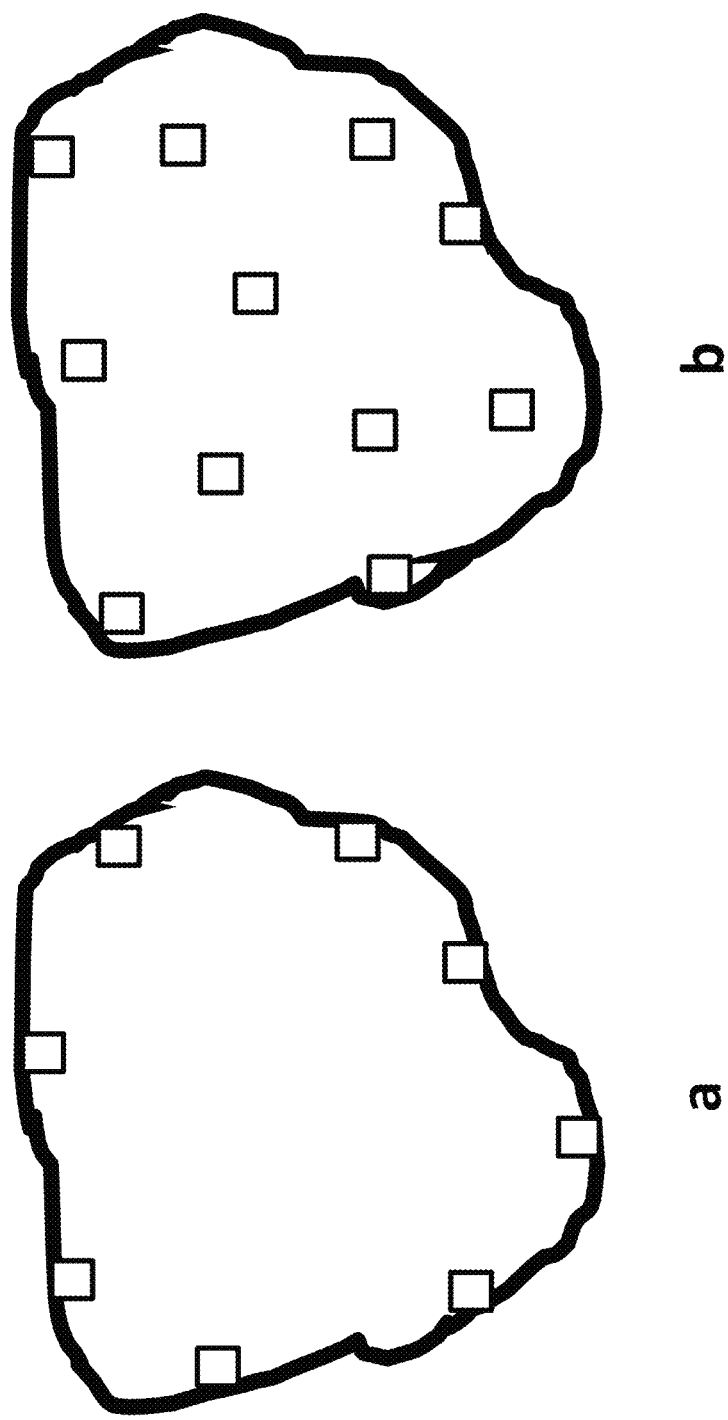
FIG. 6 shows air blowing and air sucking devices with arbitrary shape.

FIG. 6 shows configuration for nozzles or fans holders with arbitrary shape. Nozzles and fans can be located on peripheral of the arbitrary holder "a" or on surface of the holder "b". The arbitrary shape holder can be flexible and adjustable in order to create any desirable shape.

FIG. 7A illustrates an air curtain 200. The air curtain 200 blocks passage of any aerosol from each side of the air curtain to the other side of the air curtain. Air is blown from top of the air curtain 200 by an air blowing pipe 202 and sucked at the bottom of air curtain 200 by an air sucking pipe 204. The air blowing pipe 202 gets its air from an air pump and air sucking pipe 204 gets it's sucking power from an air sucking pump.

Air curtain 200 includes, among other things, air curtain holder 201, air blowing pipe 202, air blowing nozzles 203, air sucking pipe 204 and air sucking nozzles 205.

Air blowing nozzles 203 are used to control the orientation of blown air as well as amount of blown air. Air sucking nozzles 205 also control the power of sucking air and the orientation of sucked air.

In one embodiment, air curtain 200 blocks aerosol from each side of air curtain 200 to penetrate to other side of air curtain 200.

In another embodiment, air curtain 200 uses air pipes with nozzles 203 to blow air and air sucking pipe with nozzles 205 to suck the air.

In one embodiment, an air pump provides the air for air blowing pipe 202 and an air sucking pump provides the air sucking power for air sucking pipe 204.

Figure 7B:
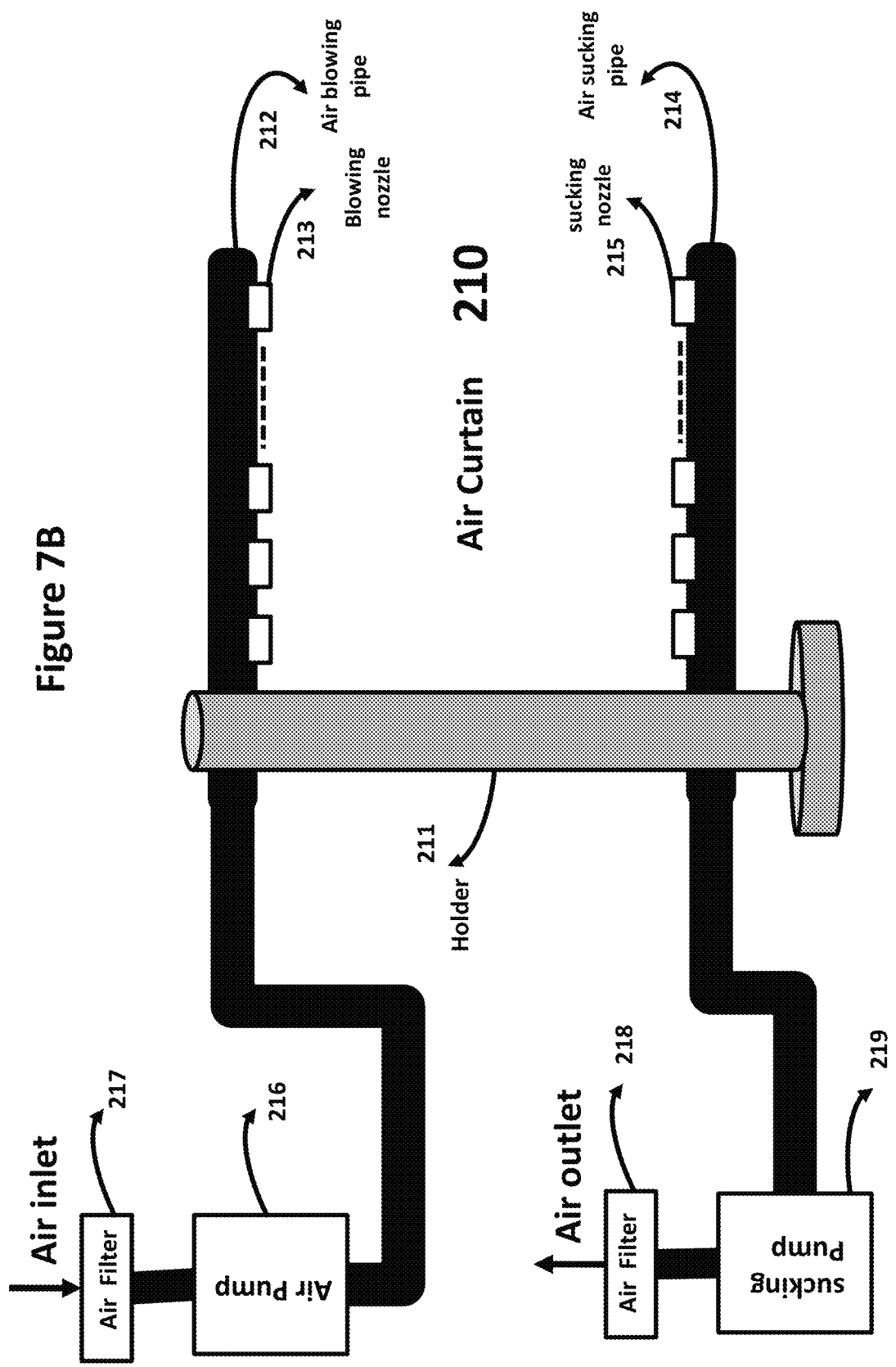

FIG. 7B illustrates an air curtain 210. The air curtain 210 blocks passage of any aerosol from each side of the air curtain to the other side of the air curtain. Air is blown from top of the air curtain 210 by an air blowing pipe 212 and sucked at the bottom of air curtain 210 by an air sucking pipe 214. The air blowing pipe 212 gets its air from air pump 216 and air sucking pipe 204 gets it's sucking power from air sucking pump 219.

Air curtain 210 includes, among other things, air curtain holder 211, air blowing pipe 212, air blowing nozzles 213, air sucking pipe 214, air sucking nozzles 215, air filter 217, air pump 216, air filter 218 and air sucking pump 219.

Air blowing nozzles 213 are used to control the orientation of blown air as well as the amount of blown air. Air sucking nozzles 215 also control the power of sucking air and the orientation of sucked air.

The air filter 217 is used to filter environment air before being pumped to air curtain 210 and air filter 218 is used to filter the contaminated air sucked by air curtain 200 and release clean air to environment.

In one embodiment, air curtain 210 blocks aerosol from each side of air curtain 210 to penetrate to other side of air curtain 210.

In another embodiment, air curtain 210 uses air pipes with nozzles 213 to blow air and air sucking pipe with nozzles 115 to suck air.

In one embodiment, an air pump provides the air for air blowing pipe 212 and an air sucking pump provides the air sucking power for air sucking pipe 214.

Figure 7C:
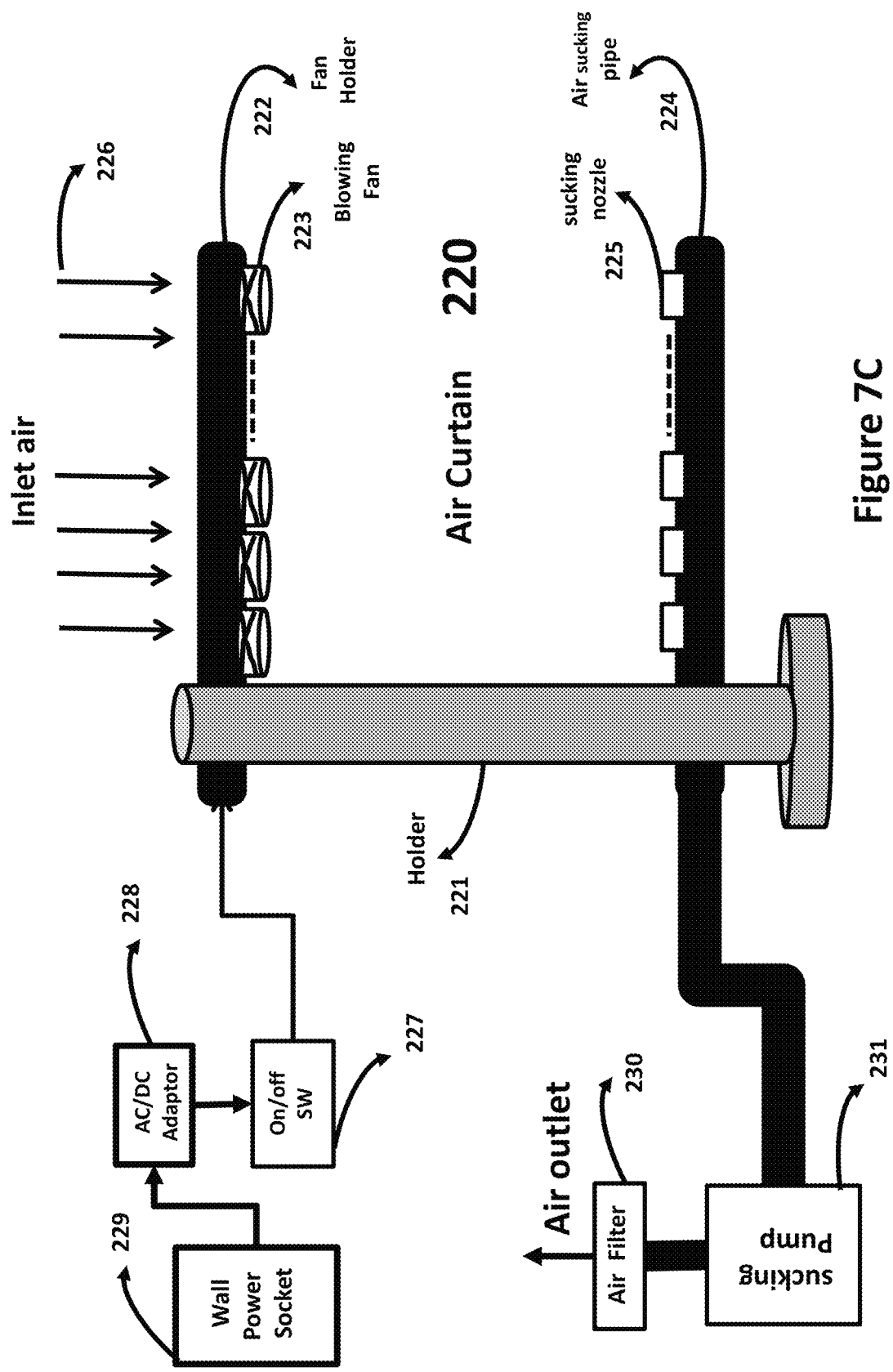

FIG. 7C illustrates an air curtain 220. The air curtain 220 blocks passage of any aerosol from each side of curtain to the other side of air curtain. Air is blown from top of the air curtain 220 by an air blowing fan 223 which is hold be a fan holder 222 and sucked at the bottom of air curtain 220 by an air sucking pipe 224. The air blowing fan 212 gets its air 226 from environment and air sucking pipe 224 gets it's sucking power from air sucking pump 231.

Air curtain 220 includes, among other things, air curtain holder 221, fan holder 222 air blowing fan 223, air sucking pipe 224 and air sucking nozzles 225, on/off switch 227, AC/DC convertor 228, wall power socket 229, air filter 230 and air sucking pump 231.

Air sucking nozzles 225 controls the power of sucking air and the orientation of sucked air.

The fan 223 gets its air 226 directly from environment. The fan 223 uses DC (direct current) voltage supplied from AC (alternate current) voltage of a wall socket 229, AC/DC converter 228 and on/off switch 227. Air filter 230 is used to filter the contaminated air sucked by air sucking pump 231 through air curtain 220 and releases clean air to environment.

In one embodiment, air curtain 220 blocks aerosol from each side of air curtain 220 to penetrate to other side of air curtain 220.

In another embodiment, air curtain 220 uses air fan 223 to blow air and air sucking pipe with nozzles 125 to suck the air which includes any aerosol.

In one embodiment, an air sucking pump provides the air sucking power for air sucking nozzle 215 though air sucking pipe 214.

Figure 7D:
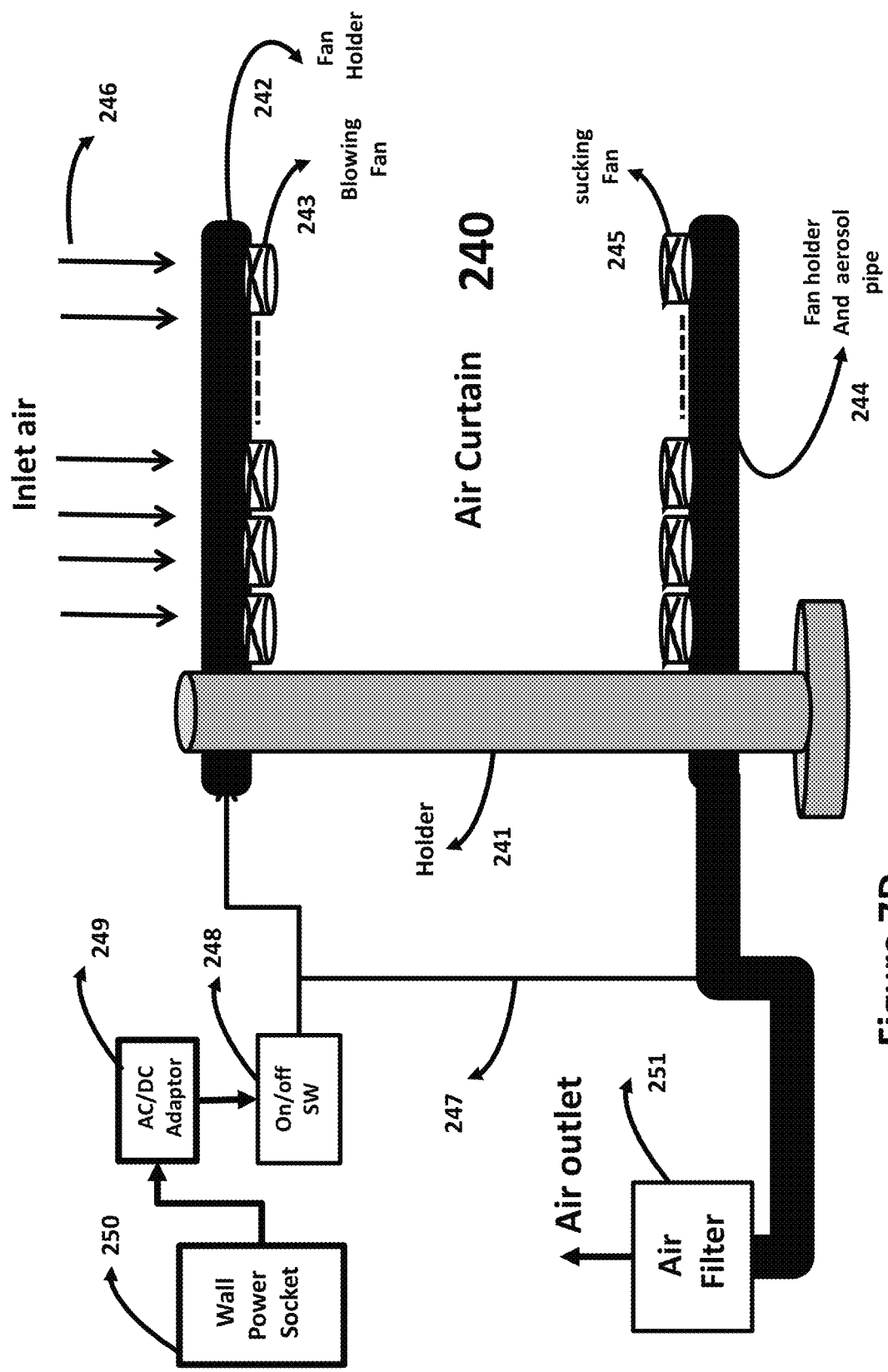

FIG. 7D illustrates an air curtain 240. The air curtain 240 blocks passage of any aerosol from each side of curtain to the other side of air curtain. Air is blown from top of the air curtain 240 by an air blowing fan 243 which is hold be a fan holder 242 and sucked at the bottom of air curtain 240 by an air sucking fan 245. The air blowing fan 243 gets its air 246 from environment and air sucking fan 245 sucks the blown air and through fan holder and aerosol pipe 244 sends to filter 251 to be filtered and released to environment.

Air curtain 240 includes, among other things, air curtain holder 241, fan holder 242, air blowing fan 243, air sucking fan 245, fan holder and aerosol pipe 224, power cord 247, on/off switch 228, AC/DC convertor 249, wall power socket 250, and air filter 251.

The fans 243 and 245 use DC (direct current) voltage supplied from AC (alternate current) voltage supplied by a wall socket 250, AC/DC converter 249 and on/off switch 248. Air filter 251 is used to filter the contaminated air sucked by air curtain 240 and release clean air to environment.

In one embodiment, air curtain 240 blocks aerosol from each side of air curtain 240 to penetrate to other side of air curtain 240.

In another embodiment, air curtain 240 uses air fan 243 to blow air and air sucking fan 245 to suck the air which includes any aerosol.

In one embodiment, air filter 251 filters the contaminated air sucked by air sucking fan 245 and release clean air to environment.

Figure 7E:
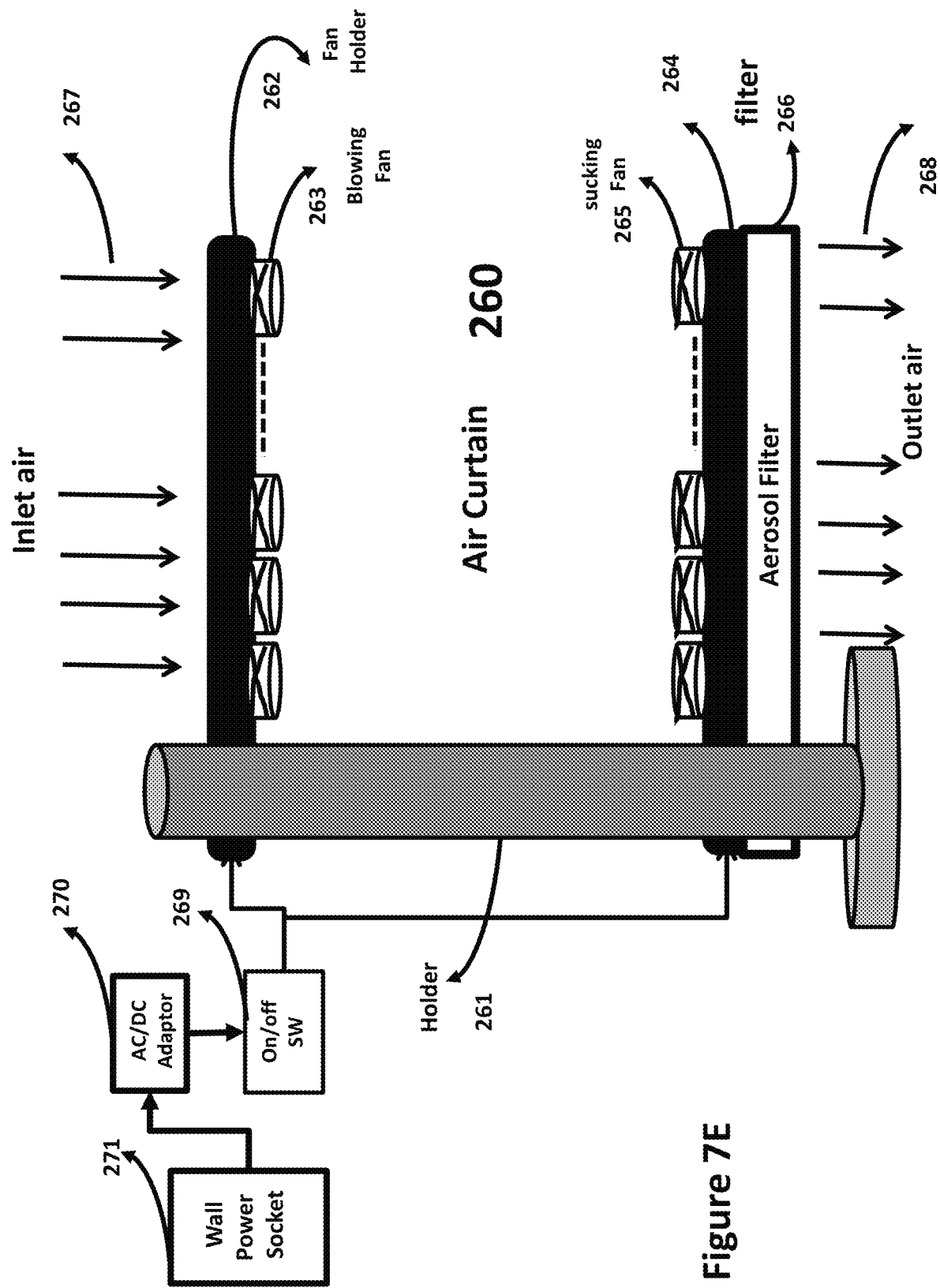

FIG. 7E illustrates an air curtain 260. The air curtain 260 blocks passage of any aerosol from each side of the air curtain to the other side of the air curtain. Air is blown from top of the air curtain 260 by an air blowing fan 263 which is hold be a fan holder 262 and sucked at the bottom of air curtain 260 by an air sucking fan 265. The air blowing fan 263 gets its air 267 from environment and air sucking fan 265 sucks the blown air and through fan holder and aerosol pipe 244 sends to aerosol filter 266 to be filtered and release clean air 268 to environment.

Air curtain 260 includes, among other things, air curtain holder 261, fan holder 262, air blowing fan 263, air sucking fan 265, fan holder 264, aerosol filter 266, on/off switch 269, AC/DC convertor 270, and wall power socket 271.

The fan 263 gets its air 267 directly from environment. The air blowing fan 263 and air sucking fan 265 use DC (direct current) voltage supplied from AC (alternate current) voltage supplied by a wall socket 271, AC/DC converter 270 and on/off switch 269. Air filter 266 is used to filter the contaminated air sucked by air sucking fan 265 and release clean air 268 to environment.

In one embodiment, air curtain 260 blocks aerosol from each side of air curtain 260 to penetrate to other side of air curtain 260.

In another embodiment, air curtain 260 uses air fan 263 to blow air, air sucking fan 265 to suck the air which includes any aerosol and aerosol filter 266 to filter the contaminated air.

In one embodiment, aerosol filter 266 filters the contaminated air sucked by air sucking fan 265 and releases clean air to environment.

In another embodiment, air curtain 260 is portable and can be moved to different locations.

In another embodiment, the holder 261 is adjustable and the distance between air blowing fan 263 and air sucking fan 265 can be adjusted.

In one embodiment, the blowing fans and sucking fans are adjusted for blowing CFM, sucking power, direction and orientation of blowing and sucking.

Figure 7F:
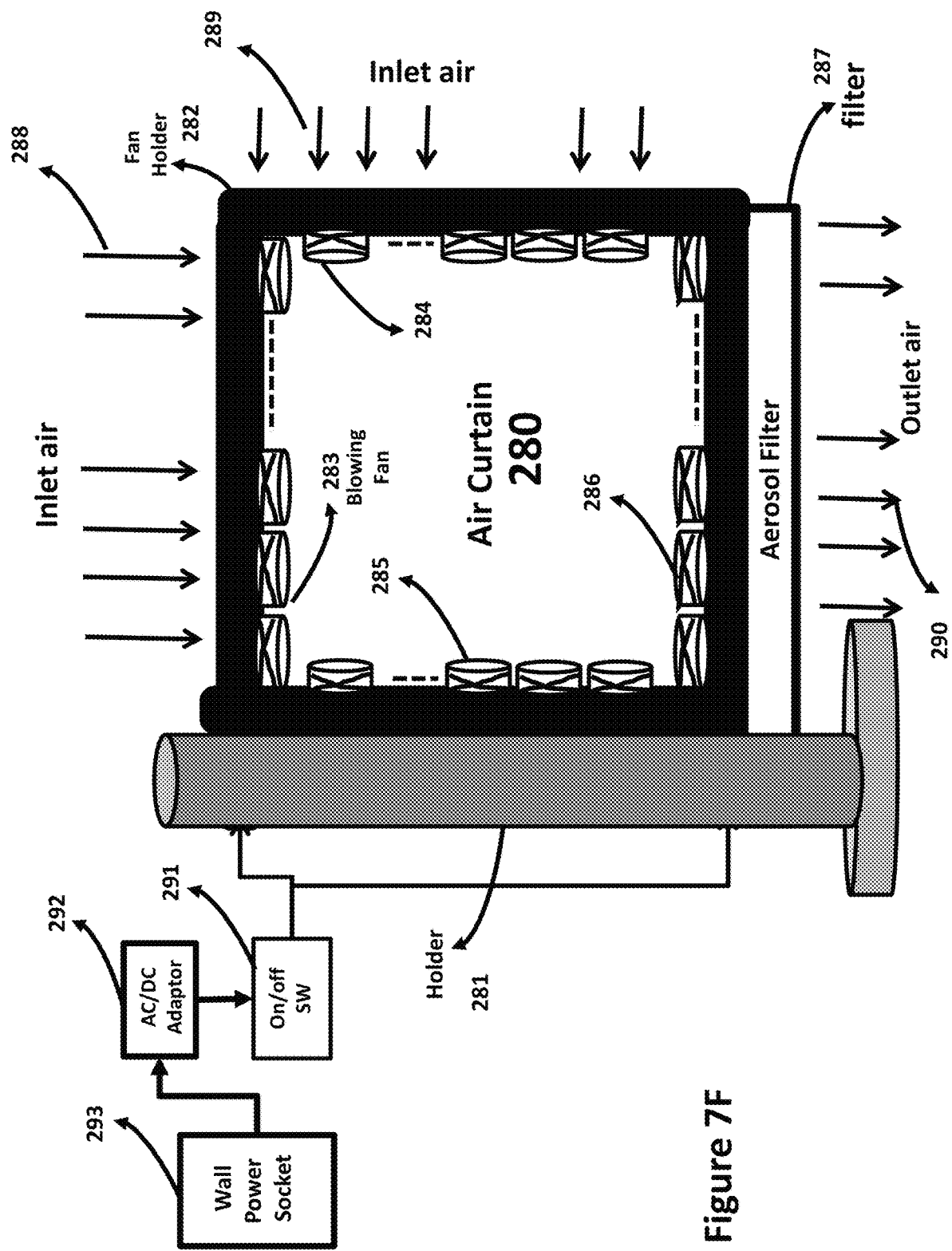

FIG. 7F illustrates an air curtain 280. The air curtain 280 blocks passage of any aerosol from each side of the air curtain to the other side of the air curtain. Air is blown from top, right and left side of the air curtain 280 by air blowing fans 263, 184, and 185 which are hold be a rectangular fan holder 282 and air is sucked at the bottom of air curtain 280 by an air sucking fan 286 which is also attached to fan holder 282. The air blowing fans 283, 184, and 285 get their air 288, and 289 from environment and air sucking fan 286 sucks the blown air and through fan holder 282 sends it to aerosol filter 287 to be filtered and release clean air 290 to environment. The air curtain holder 281 can hold 3 sides or the air curtain as one piece or have two pieces one holding left edge and one holding the right edge.

Air curtain 280 includes, among other things, air curtain holder 281, fan holder 282, air blowing fans 283, 284 and 285, air sucking fan 286, aerosol filter 287, on/off switch 291, AC/DC convertor 292, and wall power socket 293.

The fans 283, 284, and 285 get their air 288 and 289 directly from environment. The fans 283, 284, 285, and 286 use DC (direct current) voltages supplied from AC (alternate current) voltage from wall socket 293, AC/DC converter 292 and on/off switch 291. Air filter 287 is used to filter the contaminated air sucked by air sucking fan 286 and release clean air 290 to the environment.

In one embodiment, air curtain 280 blocks aerosol from each side of air curtain 280 to penetrate to other side of air curtain 280.

In another embodiment, air curtain 280 uses air fans 283, 284, and 285 to blow air, air sucking fan 286 to suck the air which includes aerosol and aerosol filter 287 to filter contaminated air.

In one embodiment, aerosol filter 287 filters the contaminated air sucked by air sucking fan 286 and releases clean air to environment.

In another embodiment, air curtain 280 is portable and can be moved to different locations.

In one embodiment, air curtain 280 uses fans 283 and 284 for air blow and fans 285 and 286 for air sucking and fan holder 282 guides the sucked air by air sucking fans 285 and 286 to aerosol filter 287 to be cleaned and released to environment.

In another embodiment, air curtain 280 uses fans 283, 284, 285, and 286 for sucking air and fan holder 282 guides the sucked air to aerosol filter 287 to be cleaned and released to environment.

Figure 7G:
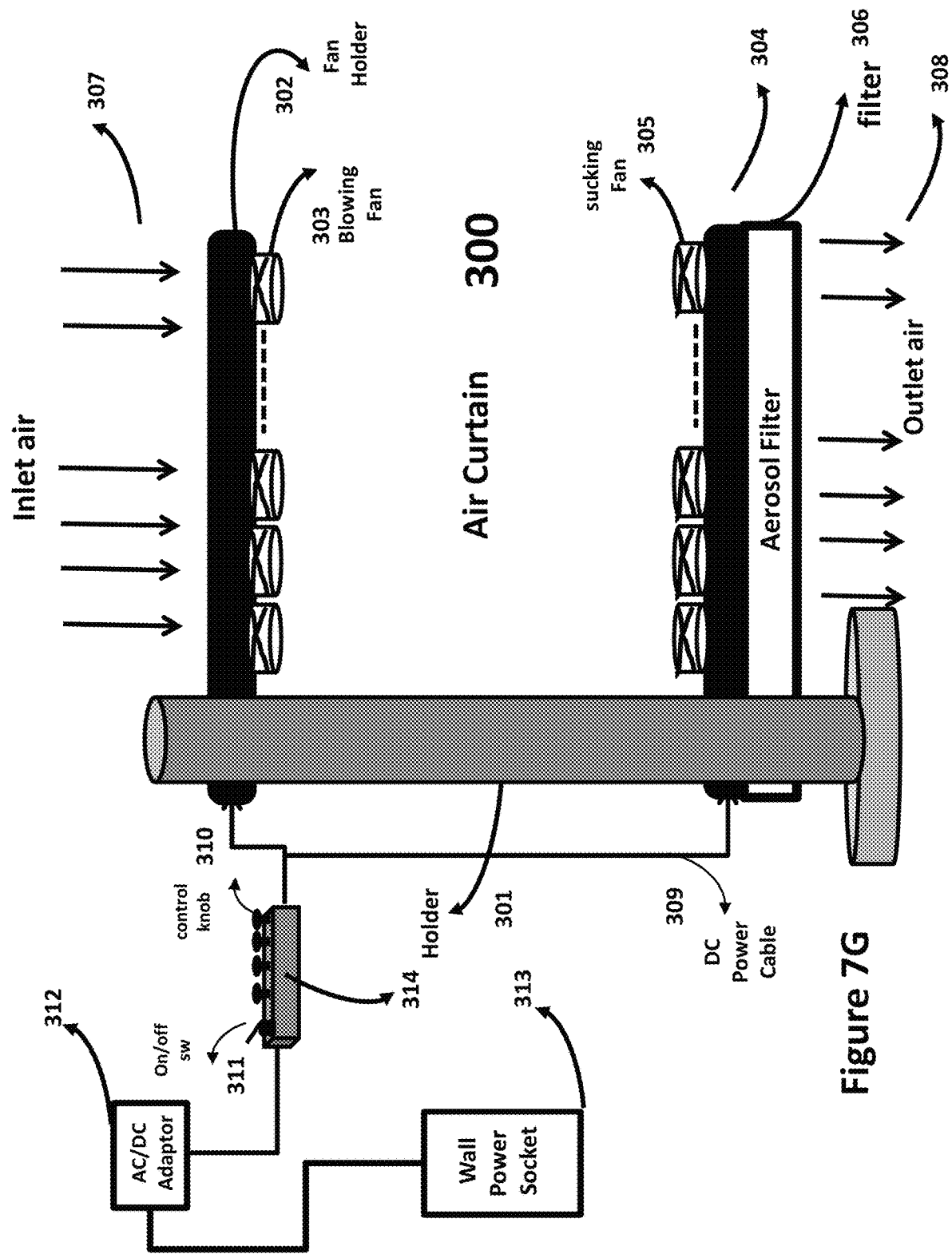

FIG. 7G illustrates an air curtain 300. The air curtain 300 blocks passage of any aerosol from each side of the air curtain to the other side of the air curtain. Air is blown from top of the air curtain 300 by an air blowing fan 303 which is hold by a fan holder 302 and sucked at the bottom of air curtain 300 by an air sucking fan 305. The air blowing fan 303 gets its air 307 from environment and air sucking fan 305 sucks the blown air and through fan holder and aerosol pipe 304 sends it to aerosol filter 306 to be filtered and release clean air 308 to environment.

Air curtain 300 includes, among other things, air curtain holder 301, fan holder 302, air blowing fan 303, air sucking fan 305, fan holder 304, aerosol filter 306, DC power cable 309, controller 314, AC/DC convertor 312, and wall power socket 313.

The fan 303 gets its air 306 directly from environment. The fan 303 and 305 use DC (direct current) voltage supplied from AC (alternate current) voltage from a wall socket 313, AC/DC converter 312 and controller 314. Aerosol filter 306 is used to filter the contaminated air sucked by air sucking fan 305 and release clean air 308 to environment.

In one embodiment, air curtain 300 blocks aerosol from each side of air curtain 300 to penetrate to other side of air curtain 300.

In another embodiment, air curtain 300 uses air fan 303 to blow air, air sucking fan 305 to suck the air which includes any aerosol and aerosol filter 306 to filter contaminated air.

In one embodiment, aerosol filter 306 filters the contaminated air sucked by air sucking fan 305 and releases clean air to environment.

In another embodiment, air curtain 300 is portable and can be moved to different locations.

In one embodiment, controller 314 has on/off switch 311 and control knobs 310 which is used to control the air flow for air blowing fan 303 and sucking power of air sucking fan 305. The control can be applied to individual fans and is done by changing DC voltage used for individual fan. The control can be done manually by knobs 310 or automatically using a processor with a control algorithm.

In another embodiment, the holder 301 is adjustable and the distance between air blowing fan 303 and air sucking fan 305 can be adjusted.

Figure 7H:
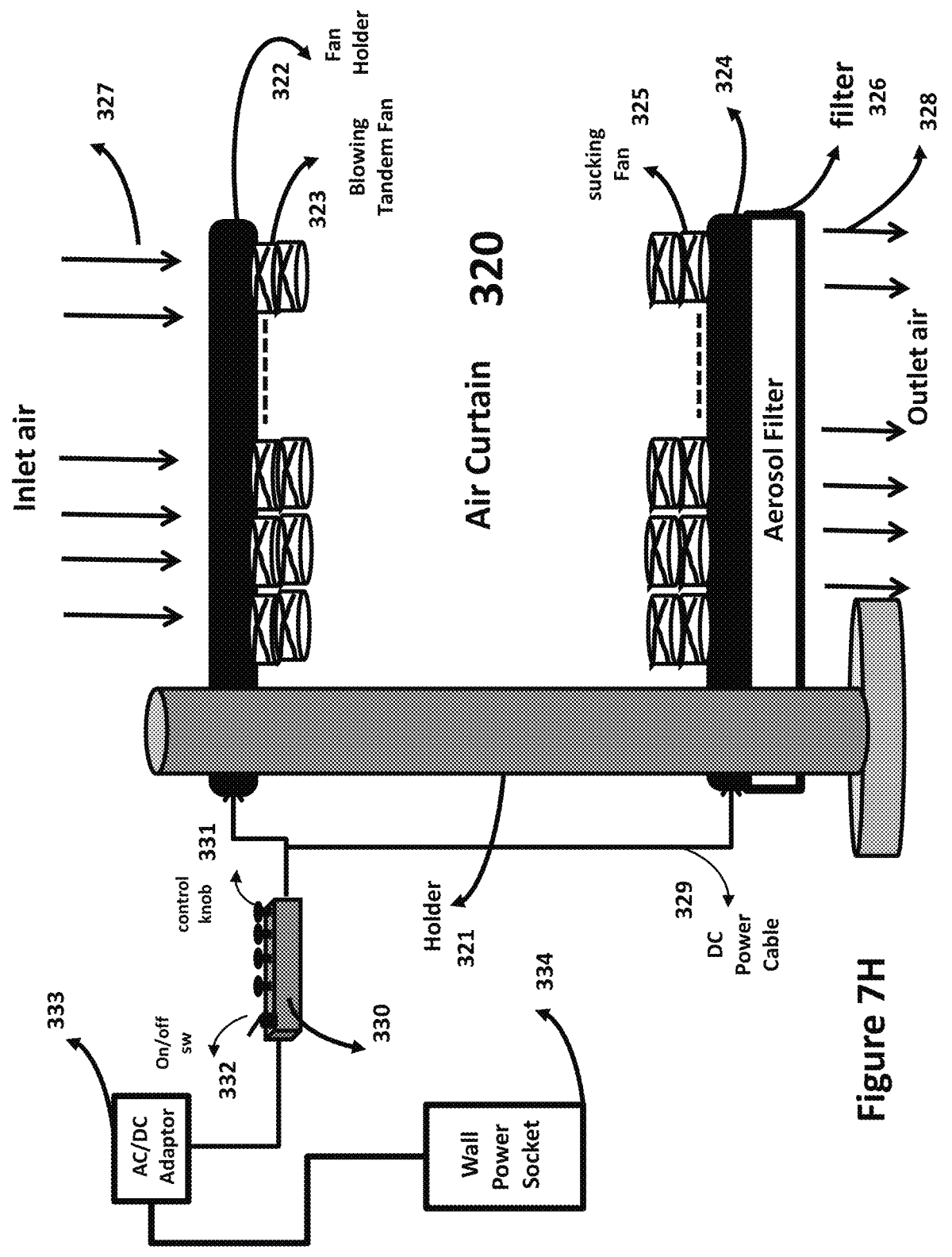

FIG. 7H depicts an air curtain 320. The air curtain 320 blocks passage of any aerosol from each side of the air curtain to the other side of the air curtain. Air is blown from top of the air curtain 320 by an air blowing fan 323 which is hold be a fan holder 322 and sucked at the bottom of air curtain 320 by an air sucking fan 325. The air blowing fan 323 gets its air 327 from environment and air sucking fan 325 sucks the blown air and through fan holder and aerosol pipe 324 sends it to aerosol filter 326 to be filtered and release clean air 328 to environment.

Air curtain 320 includes, among other things, air curtain holder 321, fan holder 322, air blowing fan 323, air sucking fan 325, fan holder 324, aerosol filter 326, DC power cable 329, controller 324, AC/DC convertor 322, and wall power socket 323.

Air curtain 320 functions exactly like air curtain 300 and the only difference is air blowing fan 323 and air sucking fan 325. Air blowing fan 323 uses two fans in tandem in order to increase the air flow. Air sucking fan 325 also uses two fans in tandem in order to increase the air sucking power.

In one embodiment, air curtain uses tandem fans for both air blowing and air sucking.

In another embodiment, the blowing fans and sucking fans are in two different vertical surface or line and operate as two shields or curtains with a specified distance between them where the blowing curtain or shield that uses blowing fan at the top is before or after the sucking curtain or shield that uses sucking fans at the bottom.

Figure 7I:
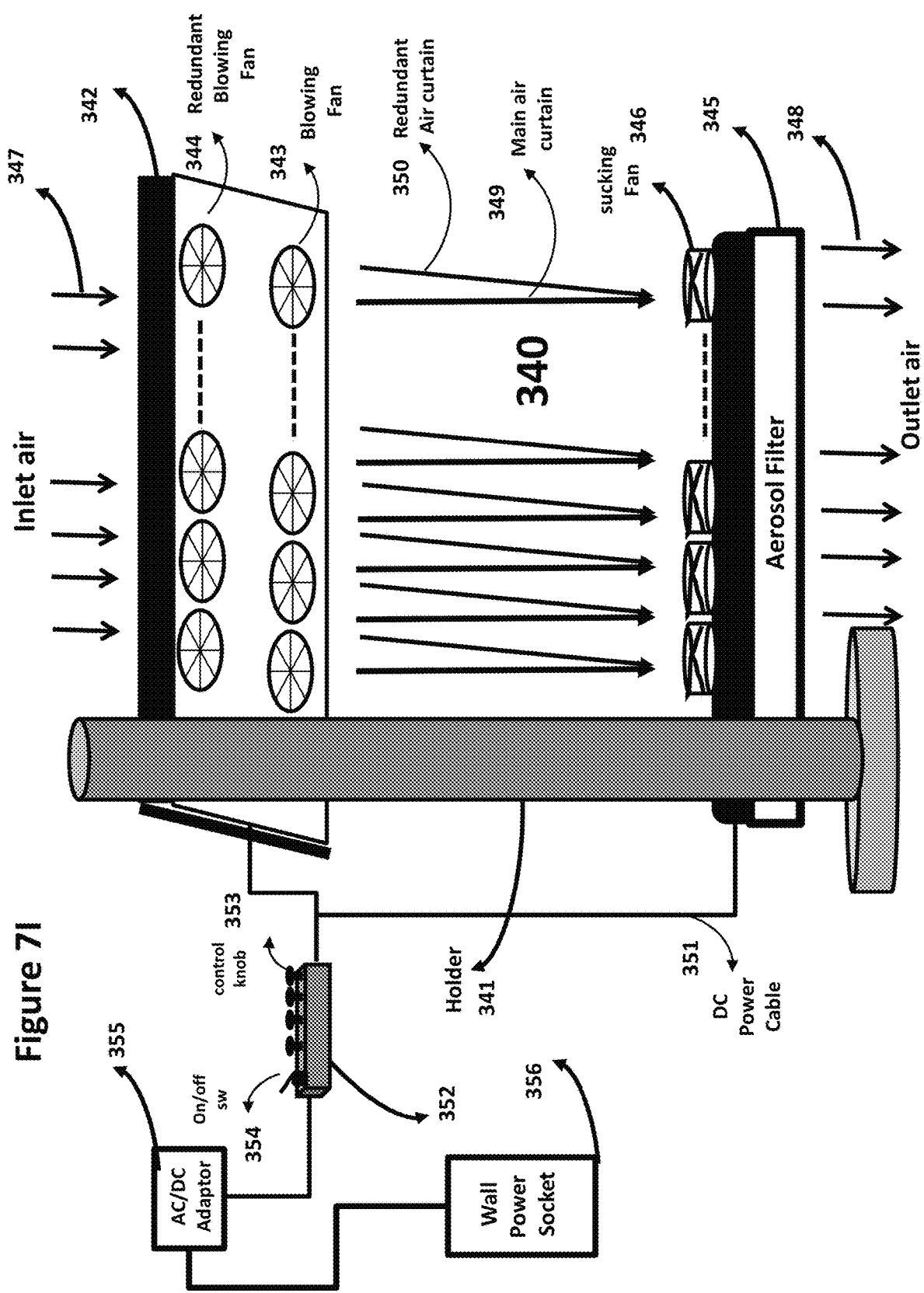

FIG. 7I depicts a protected air curtain 340. The protected air curtain 340 blocks passage of any aerosol from each side of air curtain to the other side of air curtain by main air curtain 349 and redundant air curtain 350. Air is blown from top of the air curtain 340 by an air blowing fan 343 and a redundant air blowing fan 344 which are hold by a fan holder 342 and sucked at the bottom of air curtain 340 by an air sucking fan 346. The air blowing fan 343 and redundant air blowing fan 344 get their air 347 from environment and air sucking fan 346 sucks the blown air and sends the sucked air to an aerosol filter 345 to be filtered and release clean air 348 to environment.

Protected air curtain 340 includes, among other things, air curtain holder 341, fan holder 342, air blowing fan 343, redundant air blowing fan 344, air sucking fan 346, aerosol filter 345, DC power cable 351, controller 352, AC/DC convertor 355, and wall power socket 356.

Redundant air fan 344 is used to provide a redundant air curtain 350 and block any aerosol that penetrates the main air curtain 349.

In one embodiment, the redundant air curtain consists of a main air curtain and a redundant air curtain.

In another embodiment the main and redundant air curtains have air flow at different configurable angles and their orientations are towards the air sucking fan or pipe.

Figure 8A:
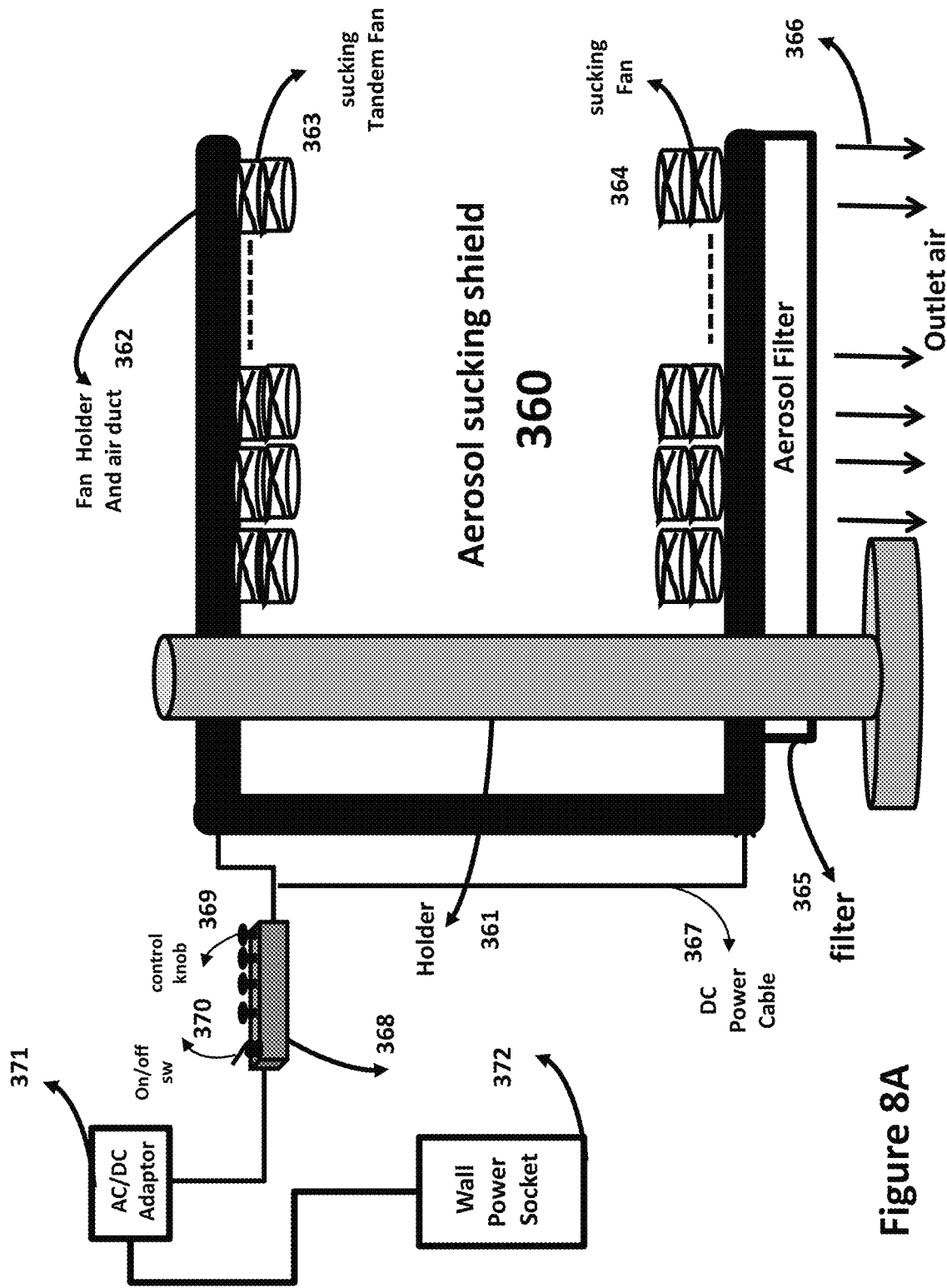
FIGS. 8A through 8D illustrate various aerosol sucking shields.

FIG. 8A depicts an aerosol sucking shield 360. The aerosol sucking shield 360 blocks passage of any aerosol from each side of shield to the other side of shield. Air is sucked from top and bottom of the aerosol sucking shield 360 by air sucking fan 363 at the top of the shield and air sucking fan 364 at the bottom of the shield. Both top air sucking fan 363 and bottom air sucking fan 364 are hold by a fan holder and air pipe 362. The air sucking fan 363, and 364 suck the air between two fans and through fan holder and air pipe 362 sends it to aerosol filter 365 to be filtered and release clean air 366 to the environment.

The aerosol sucking shield 360, among other things, includes aerosol sucking shield holder 361, fan holder and air pipe 362, air sucking fan 363, air sucking fan 364, aerosol filter 365, DC power cable 367, controller 368, AC to DC convertor 371, and wall power socket 372.

Air sucking fan 363 and 364 use two fans in tandem in order to increase the air sucking power.

In one embodiment, aerosol sucking shield uses only air sucking fan.

In another embodiment, aerosol sucking shield uses air sucking fans that have two fans in tandem.

In another embodiment, the sucking fans are adjusted for sucking power, direction and orientation of sucking.

Figure 8B:
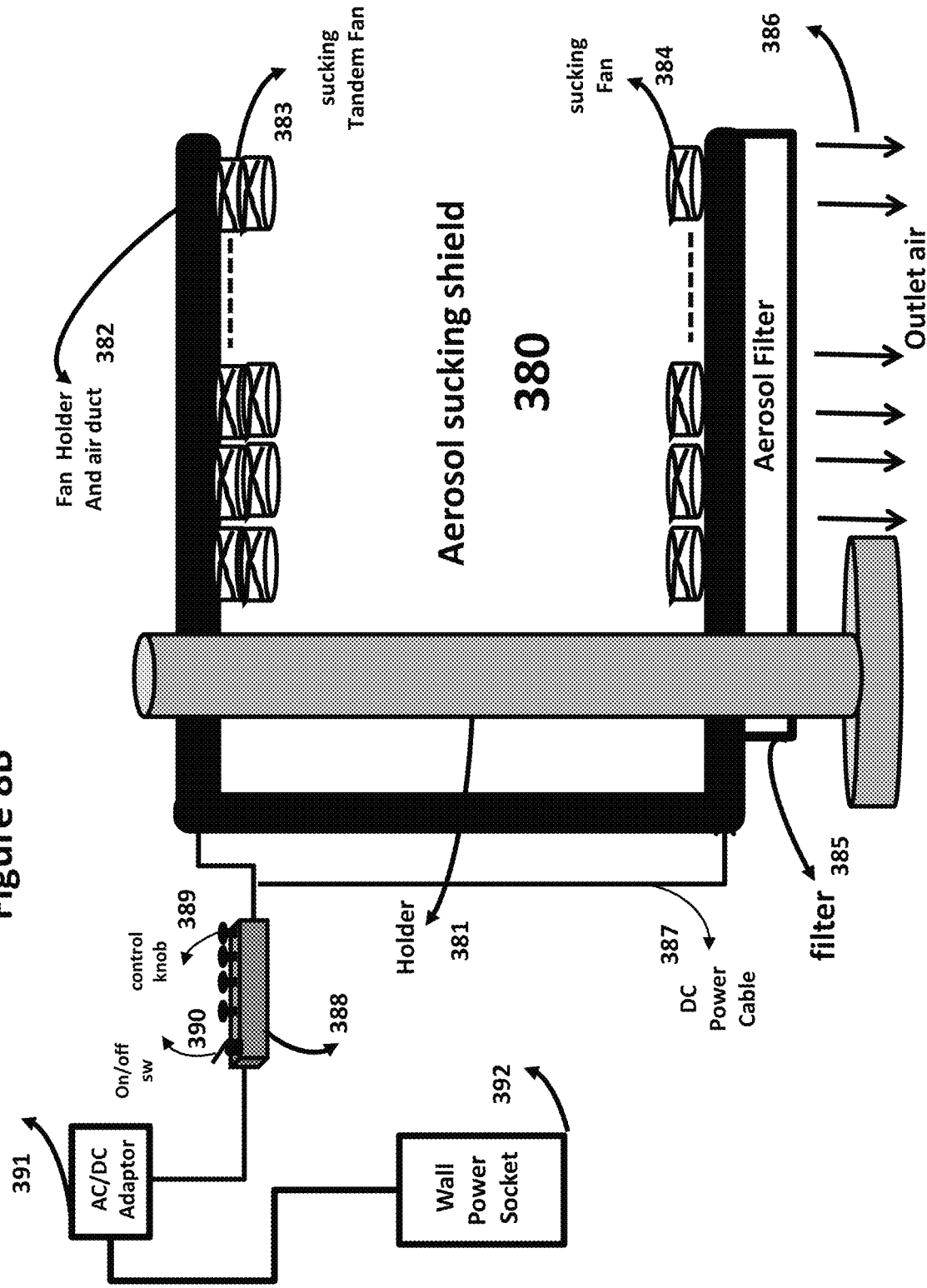

FIG. 8B shows an aerosol sucking shield 380. Aerosol sucking shield 380 functions similar to aerosol sucking shield 360. It also has the same components and architecture as aerosol sucking shield 360. The only difference between aerosol sucking shield 380 and aerosol sucking shield 360 is the bottom sucking fan 384. The bottom sucking fan in aerosol sucking shield 380 does not have tandem fans. It has only single fans.

In one embodiment, aerosol sucking shield uses two tandem sucking fans at the top of the shield and single sucking fan at the bottom of the aerosol sucking shield.

Figure 8C:
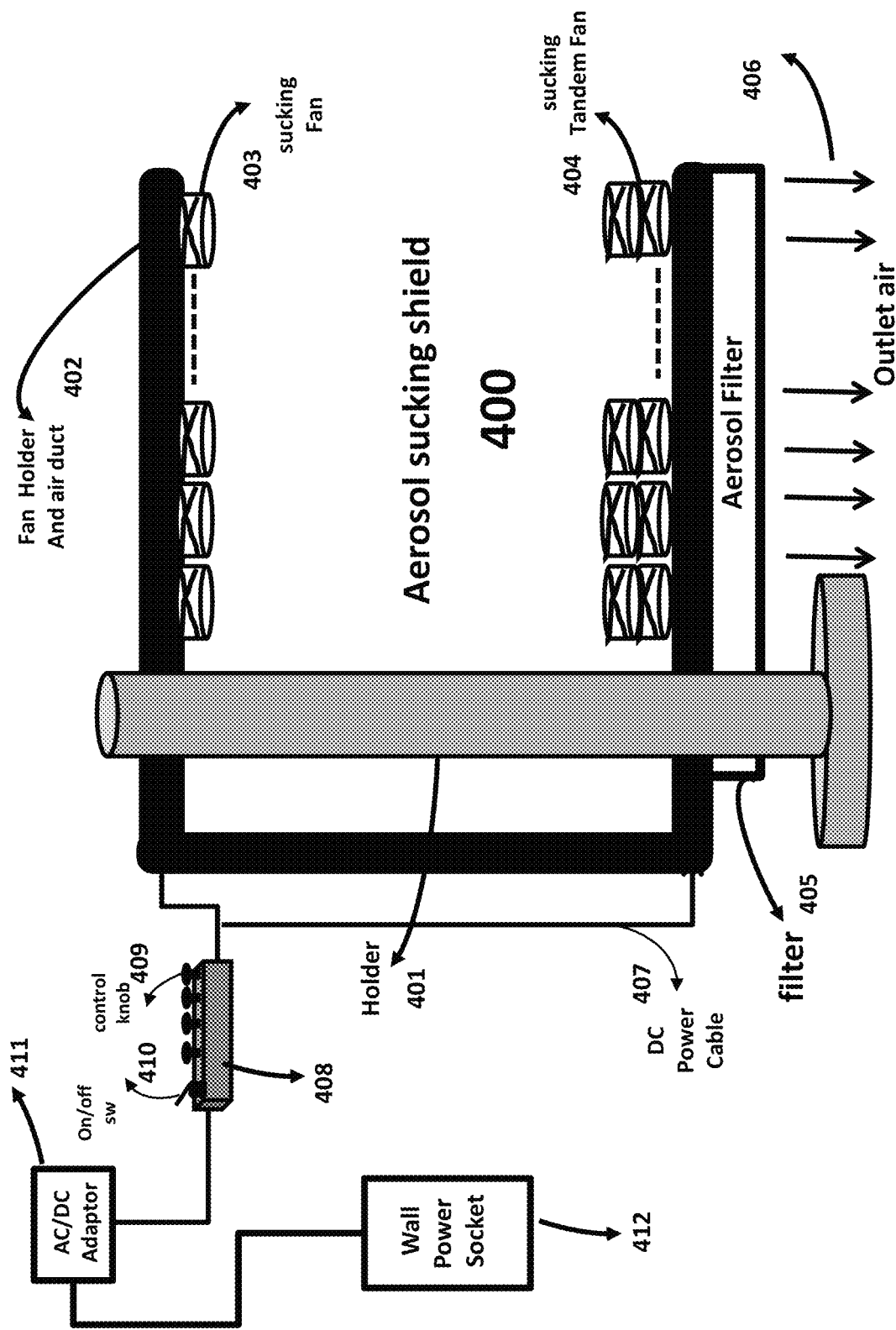

FIG. 8C depicts an aerosol sucking shield 400. Aerosol sucking shield 400 functions similar to aerosol sucking shield 360. It also has the same components and architecture as aerosol sucking shield 360. The only difference between aerosol sucking shield 400 and aerosol sucking shield 360 is the top sucking fan 403. The top sucking fan in aerosol sucking shield 400 does not have two tandem fans. It has only single fan.

In one embodiment, aerosol sucking shield uses single sucking fan at the top of the shield and two tandem sucking fans at the bottom of the aerosol sucking shield.

Figure 8D:
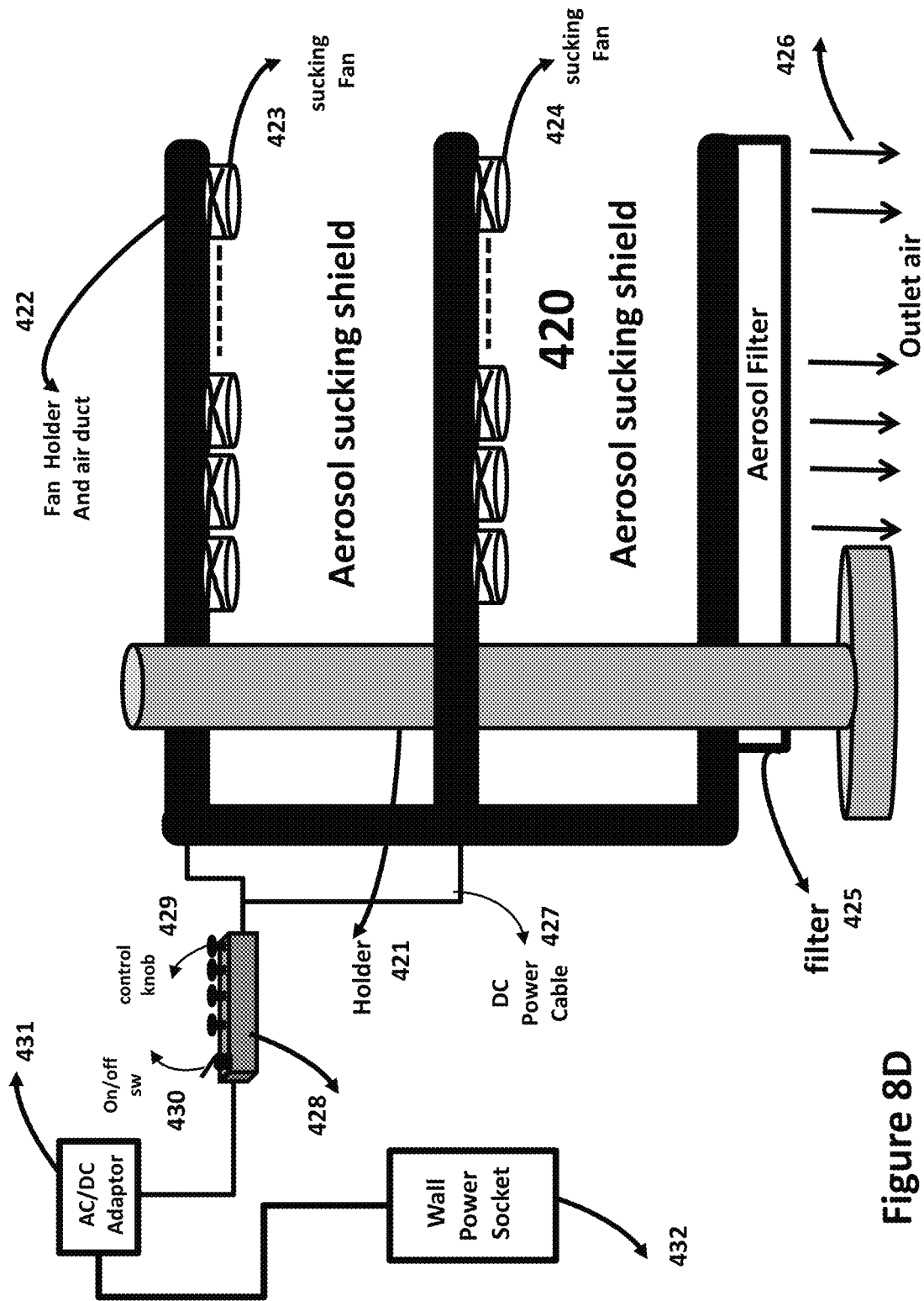

FIG. 8D illustrate a double aerosol sucking shield 420. The double aerosol sucking shield 420 blocks passage of any aerosol from each side of shield to the other side of shield. The double aerosol sucking shield 420 comprises of two independent aerosol sucking shield one on top of the other one. Each independent aerosol sucking shield has only sucking fans at top edge of the independent sucking shield. Air is sucked from top of each independent aerosol sucking shield of double aerosol sucking shield 420 by air sucking fan 423 at the top edge of the top independent aerosol sucking shield and air sucking fan 424 at the top of the bottom independent aerosol sucking shield. Both air sucking fan 423 and air sucking fan 424 are hold by a fan holder and air pipe 422 which is commonly used by both independent aerosol sucking shields. The air sucking fan 423 and 424 sucks the aerosol that is passing through two independent aerosol sucking shields and through common fan holder and air pipe 422 sends it to aerosol filter 425 to be filtered and release clean air 426 to environment.

The double aerosol sucking shield 420, among other things, includes double aerosol sucking shield holder 421, common fan holder and air pipe 422, air sucking fan 423, air sucking fan 424, aerosol filter 425, DC power cable 427, controller 428, AC/DC convertor 431, and wall power socket 432.

Air sucking fan 423 and 424 use two fans in tandem in order to increase the air sucking power.

In one embodiment, double aerosol sucking shield uses two independent aerosol sucking shield one on top of the other one.

In one embodiment, double aerosol sucking shield uses only air sucking fan.

In another embodiment, aerosol sucking shield uses air sucking fan that have a single fan.

FIG. 9A depicts a typical washing sink 440. The washing sink is used in kitchens, bathrooms, dentist operatory room, hospital rooms, prisons and many other places. The sink 440 has a washing component 441, a drainage pipe 442, standing water 443, and a wall outlet 444 where the drainage pipe 442 is connected to sewage system.

The standing water 443 blocks any aerosol or smell from sewage system to go to the sink and contaminate the environment.

Figure 9B:
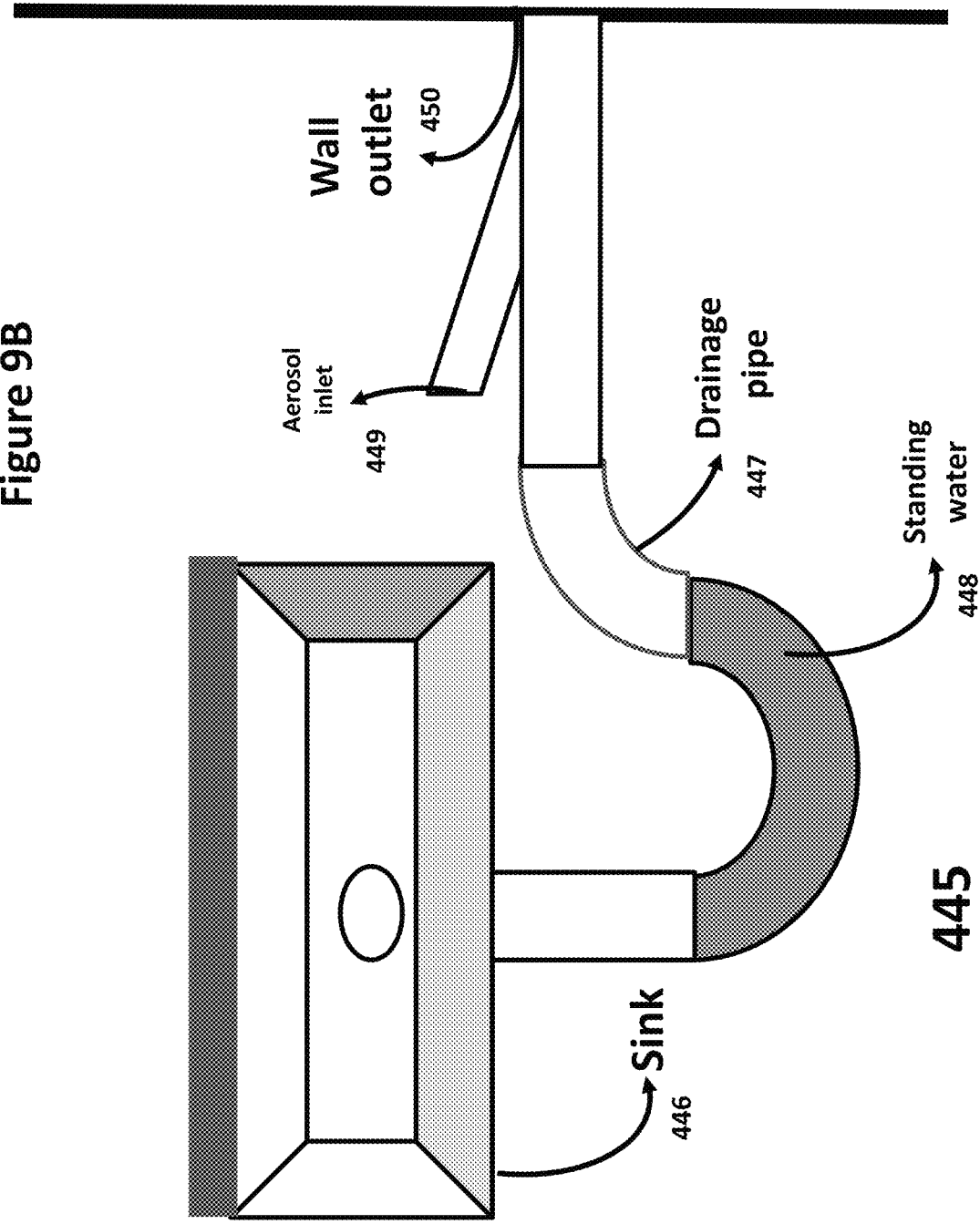

FIG. 9B depicts a typical washing sink 445. The washing sink is used in kitchens, bathrooms, dentist operatory room, hospital rooms, prisons and many other places. The sink 445 has a washing component 446, a drainage pipe 447, standing water 448, an aerosol inlet 449 and wall outlet 450 where the drainage pipe 447 is connected to sewage system.

The standing water 448 blocks any aerosol or smell from swage system or aerosol inlet to go to the sink and contaminate the environment.

In one embodiment, the drainage pipe of a washing sink is used to dispose an aerosol.

In one embodiment, the aerosol inlet is after water standing of drainage pipe in order to block any aerosol to penetrate the environment.

Figure 10A:
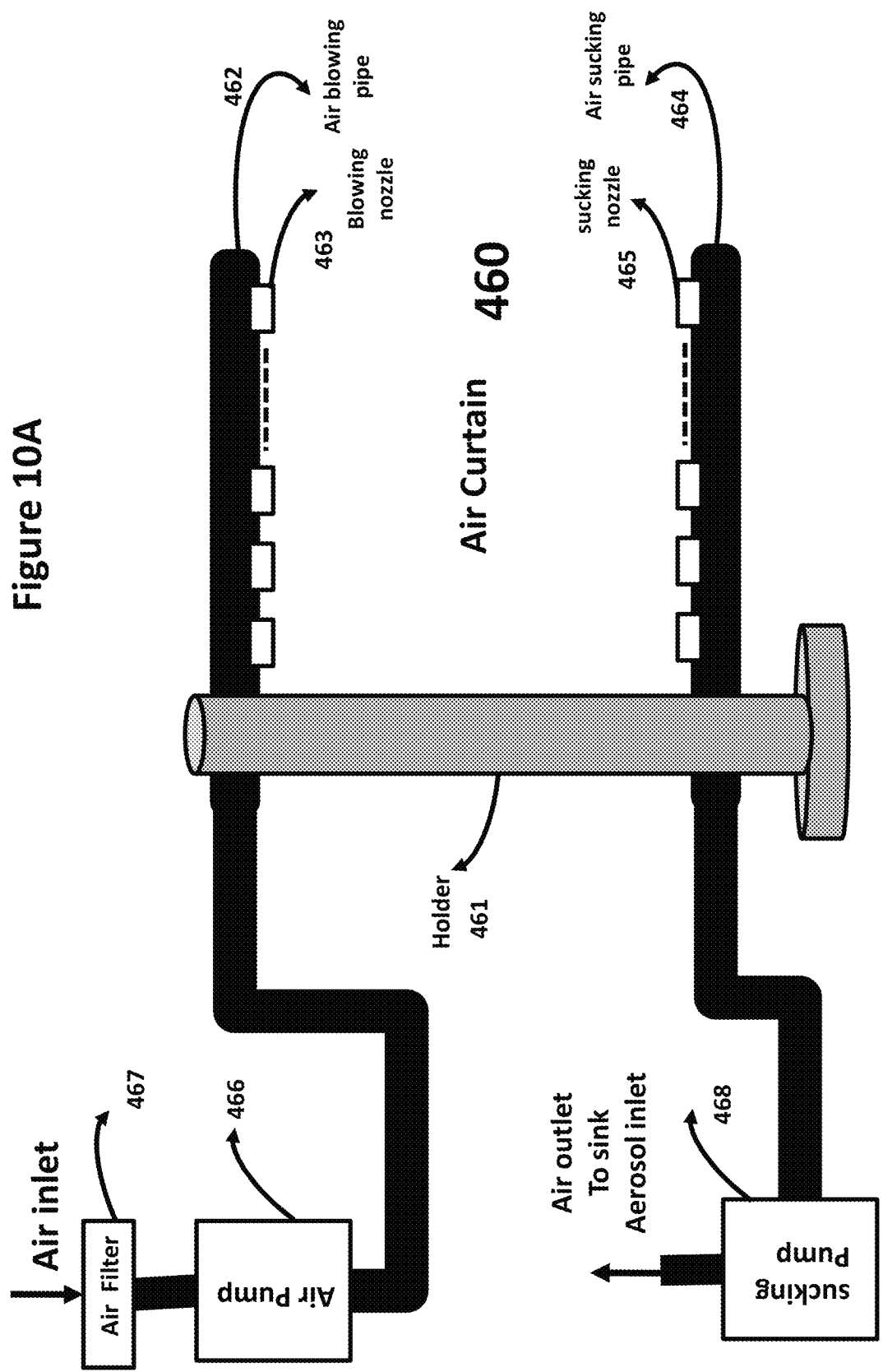
FIGS. 10A and 10B depict air curtain without aerosol filter

FIG. 10A shows an air curtain 460. Air curtain 460 functions similar to air curtain 210 shown in FIG. 7B. It also has the same components and architecture as air curtain 210. The only difference between air curtain 460 and air curtain 210 is the aerosol filter. Air curtain 460 does not use an aerosol filter and sucked aerosols are sent to an external disposal inlet.

In one embodiment, air curtain 460 uses an external aerosol disposal such as sewage inlet or a sink disposal inlet.

Figure 10B:
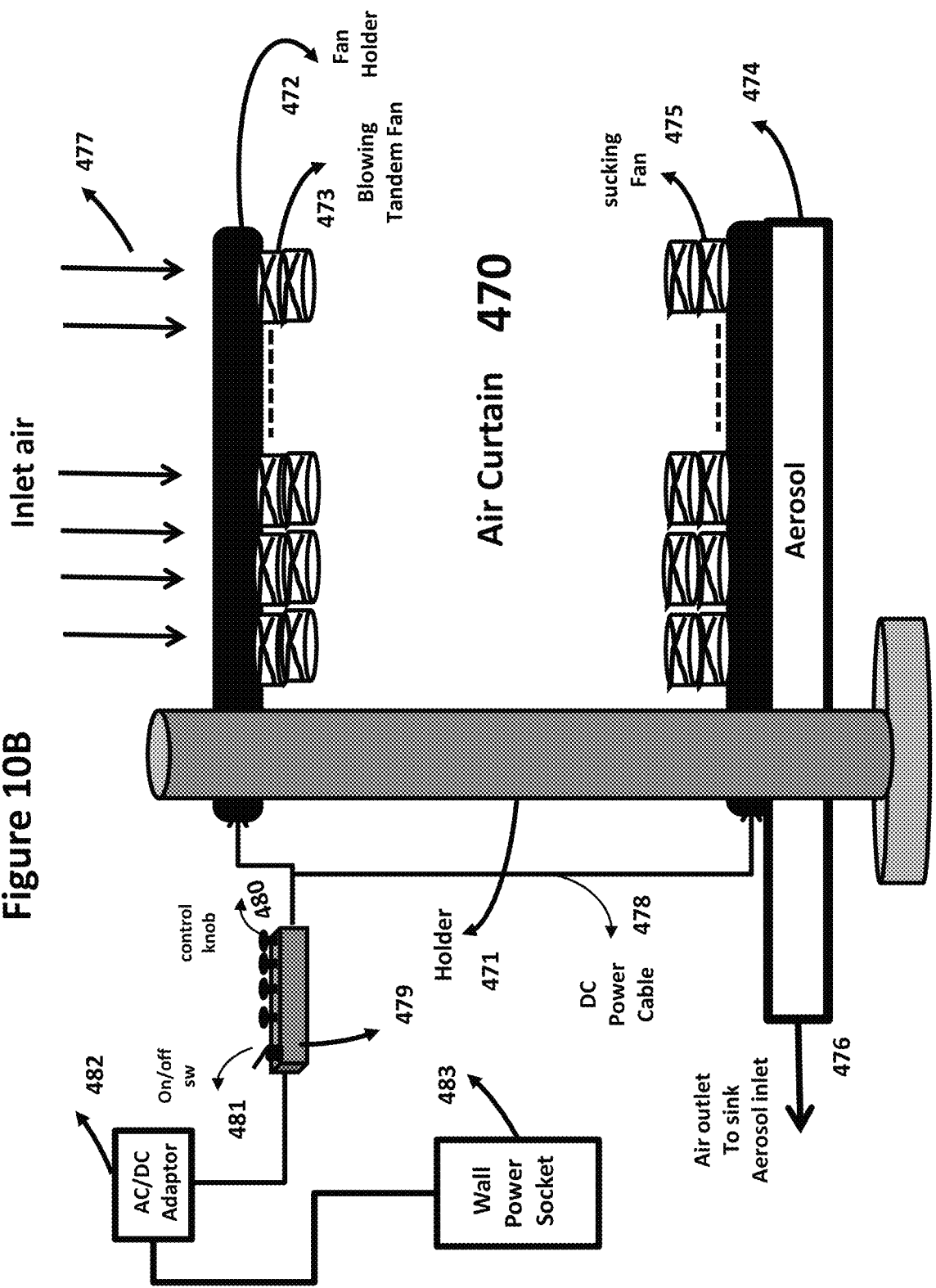

FIG. 10B shows an air curtain 470. Air curtain 470 functions similar to air curtain 320 shown in FIG. 7H. It also has the same components and architecture as air curtain 320. The only difference between air curtain 460 and air curtain 320 is the aerosol filter. Air curtain 470 does not use an aerosol filter and sucked aerosols are sent to an external disposal through outlet 476.

In one embodiment, air curtain 470 uses an external aerosol disposal such as sewage inlet or a sink disposal inlet.

Figure 11:
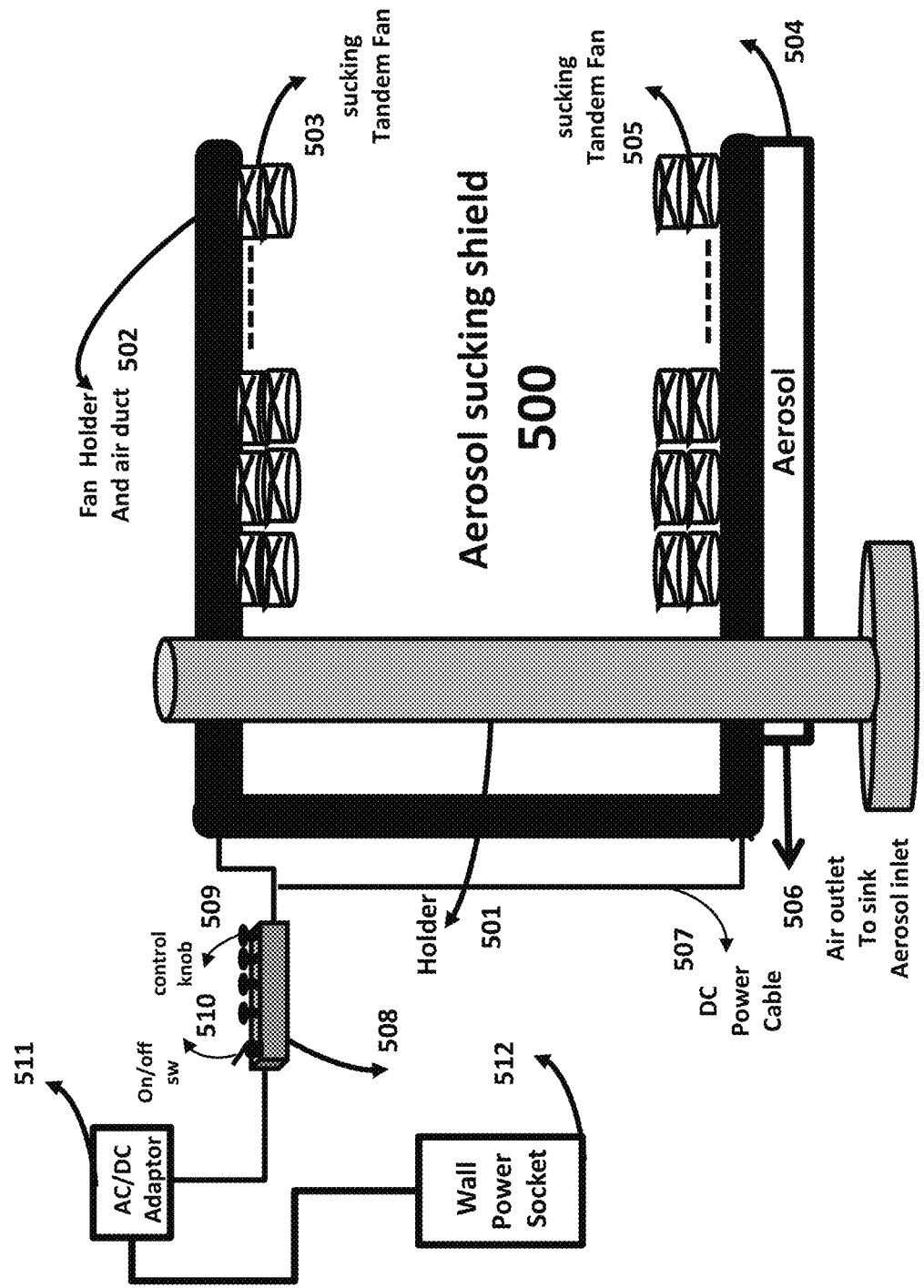
FIG. 11 shows aerosol sucking shield without aerosol filter

FIG. 11 shows an aerosol sucking shield 500. Aerosol sucking shield 500 functions similar to aerosol sucking shield 360 shown in FIG. 8A. It also has the same components and architecture as aerosol sucking shield 360. The only difference between aerosol sucking shield 500 and aerosol sucking shield 360 is the aerosol filter. Aerosol sucking shield 500 does not use an aerosol filter and sucked aerosols are sent to an external disposal through outlet 506.

In one embodiment, aerosol sucking shield 500 uses an external aerosol disposal like sewage inlet or a sink disposal inlet.

Figure 12A:
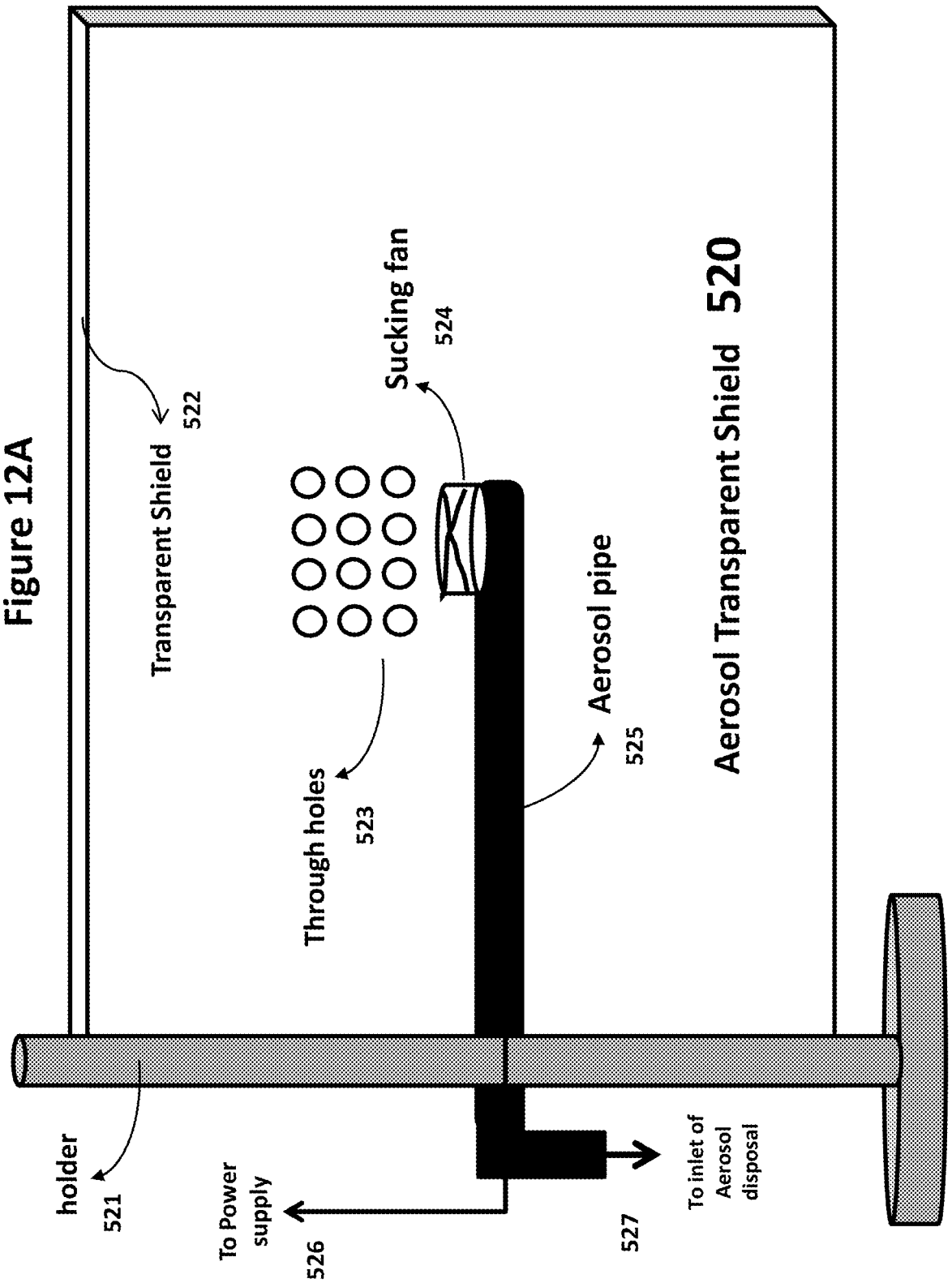

FIG. 12A illustrates an aerosol transparent shield 520. The aerosol transparent shield 520 blocks passage of any aerosol from each side of the transparent shield to the other side of transparent shield 522. The transparent shield which is hold by holder 521 has a cluster of audio through holes 523 to facilitate audio communication from one side of transparent shield 522 to the other side of the transparent shield 522. In order to block any aerosol that penetrates cluster of audio through holes 523 an aerosol sucking fan 524 is used above or below the cluster of audio through holes 523. The aerosol sucking fan 524 can be installed either side of transparent shield 522 and above or below cluster of through holes 523. The aerosol sucking fan 524 is powered by power supply 526. The aerosol sucked by aerosol sucking fan 524 is guided to inlet of aerosol disposal 527 by aerosol pipe 525.

Aerosol transparent shield 520 includes, among other things, shield holder 521, transparent shield 522, cluster of audio through holes 523, aerosol sucking fan 524, aerosol pipe 525, and power supply 526.

In one embodiment, a transparent shield with cluster of audio through holes and aerosol sucking fan above or below the cluster of through holes is used to block aerosol penetrating from one side of transparent shield to the other side of the transparent shield.

FIG. 12B illustrates an aerosol transparent shield 530. The aerosol transparent shield 530 blocks passage of any aerosol from each side of the transparent shield to the other side of transparent shield 532. The transparent shield which is hold by holder 531 has a cluster of audio through holes 533 to facilitate audio communication from one side of transparent shield 532 to the other side of the transparent shield 532. In order to block any aerosol that penetrates cluster of audio through holes 533 an aerosol sucking fan 534 is used above, below, left side or right side of the audio through holes 533. The aerosol sucking fan 534 can be installed either side of transparent shield 532 and above or below cluster of through holes 533. The aerosol sucking fan 534 is powered by power supply 536. The aerosol sucked by aerosol sucking fan 534 is guided to aerosol filter 537 by aerosol pipe 535.

Aerosol transparent shield 530 includes, among other things, shield holder 531, transparent shield 532, cluster of audio through holes 533, aerosol sucking fan 534, aerosol pipe 535, power supply 536, aerosol filter 537, and moving flexible plastic (other materials) 539.

Aerosol transparent shield 530 is portable and mobile and can be used at different locations. The aerosol transparent shield 530 has a gap between the transparent shield 532 and the surface holding the aerosol transparent shield 530. The gap is used for passing materials from one side of the shield to the other side of shield. In order to stop any aerosol penetrating from one side of transparent shield to the other side through the gap between the transparent shield 532 and the surface a plastic (or similar material) tape 539 attached to transparent shield that moves to front and back is used.

The aerosol transparent shield 530 has an aerosol filter 537 that is attached to the holder 531. Aerosol pipe 535 guides the aerosol sucked by sucking fan 534 to aerosol filter 537 and clean air 538 is released.

In one embodiment, a transparent shield with a cluster of audio through holes and aerosol sucking fan above, below, left side, or right side of the cluster of through holes is used to block aerosol penetrating from one side of transparent shield to the other side of the transparent shield.

In another embodiment, an aerosol transparent shield is self contained and has an aerosol filter attached to its holder.

In one embodiment, an aerosol transparent shield is portable and powered by attached batteries.

In another embodiment, an aerosol transparent shield uses a plastic tape that moves front and back at the gap between its transparent shield and surface the aerosol transparent shield sits on.

FIG. 12C illustrates an aerosol transparent shield 540. The aerosol transparent shield 540 blocks passage of any aerosol from each side of the transparent shield to the other side of transparent shield 542. The transparent shield which is hold by holder 541 has "n" cluster of audio through holes 543 to facilitate audio communication from one side of transparent shield 542 to the other side of the transparent shield 542 at multiple locations. The "n" cluster of audio through holes 543 are separated from each other by a fixed or variable distance. The number of cluster of audio through holes 543 "n" depends on the application of transparent shield 542 and "n" is an integer number. In order to block any aerosol that penetrates "n" cluster of audio through holes 523 an aerosol sucking fan 544 is used above, below, right and left hand side of each of "n" cluster of audio through holes 523. The aerosol sucking fan 544 can be installed either side of transparent shield 542. The aerosol sucking fans 544 powered by power supply 546. The aerosol sucked by aerosol sucking fans 544 is guided to inlet of aerosol disposal 547 by aerosol pipe 545. Transparent shield holder 541 allows the transparent shield to be hanged from ceiling or any structure above the transparent shield by hanger 548.

Aerosol transparent shield 540 includes, among other things, shield holder 541, transparent shield 542, "n" audio through holes 543, "n" aerosol sucking fans 544, aerosol pipe 545, and power supply 546.

In one embodiment, a transparent shield with multiple cluster of audio through holes spaced with equal distance or random distance, having an aerosol sucking fan above, below, right or left side of the cluster of through holes is used to block aerosol penetrating from one side of transparent shield to the other side of the transparent shield.

FIG. 12D illustrates an aerosol transparent shield 550. The aerosol transparent shield 550 functions similar to aerosol transparent shield 540 in FIG. 12C. The only difference is position of the "n" aerosol sucking fans that are below "n" cluster of audio through holes.

FIG. 13 depicts a door aerosol sucking shield 560. Door aerosol sucking shield 560 blocks any aerosol from entering or exiting a door. Sucking fan 562 on the left and sucking fan 563 on the right of door frame 561 suck any aerosol that tries to penetrate the door aerosol sucking shield 560 from either side of the door aerosol sucking shield 560. The sucked aerosol by sucking fans 562 and 563 are guided to an aerosol disposal inlet 565 by aerosol pipe 564. The sucked aerosol by sucking fans 562 and 563 can also be guided to an aerosol filter which attached to the door frame 561 by aerosol pipe 564.

Door aerosol sucking shield 560 includes, among other things, left side sucking fan 562, right side sucking fan 563, aerosol pipe 564, and an attached aerosol filter.

In one embodiment, a door aerosol sucking shield uses sucking fans attached to the frame of the door to block any aerosol passing through the door.

FIG. 14A shows air blowing fan assembly 580. Air blowing fan assembly 580 can also be used for an air sucking fan. Air blowing fan 581 takes the air from environment and blow it to guidance horn 583 that release the air to environment with higher CFM and narrower width. The air blowing fan 581 is hold with a holder 582 that is attached to guidance horn 583. When this assembly is used for sucking fan, air is sucked from end opening of guidance horn 583 and releases to environment by the sucking fan.

In one embodiment, a horn is used to make the air blown by an air blowing fan focused, with higher CFM and narrower width.

Figure 14B:
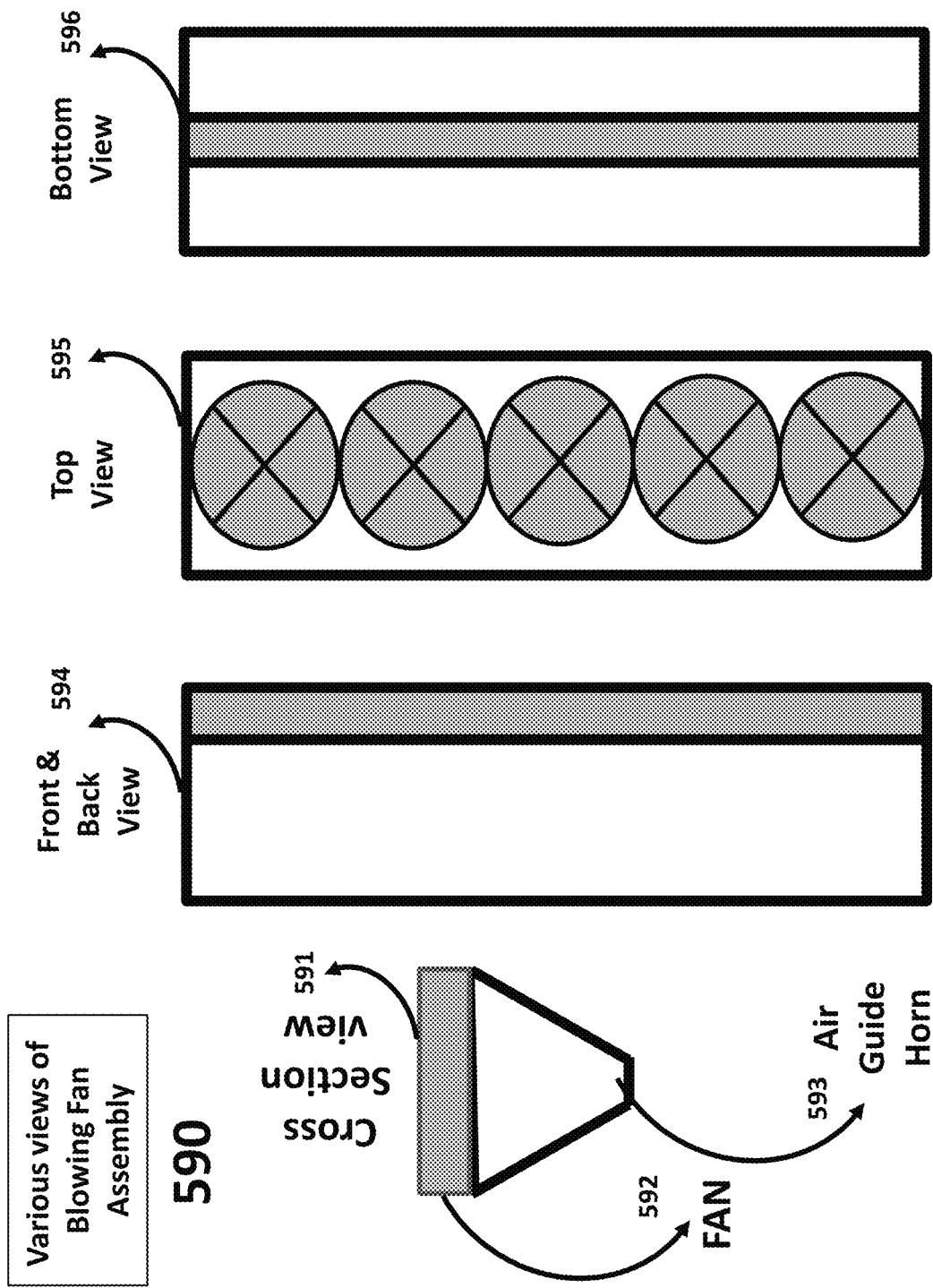

FIG. 14B illustrate various views of air blowing assembly 590. Air blowing assembly 590 can also be used by an air sucking fan. Air blowing assembly 590 has cross section 591 that shows fan 592 in gray color and guidance horn 593. The front and back view 594 of the air blowing fan assembly 590 shows air blowing fan and air guidance horn. The top view 595 of the air blowing fan assembly 590 shows air blowing fan only. The bottom view 596 of the air blowing fan assembly 590 shows air guidance horn and where the air exits in case of air blowing fan and where air enters in case of air sucking fan.

Figure 14C:
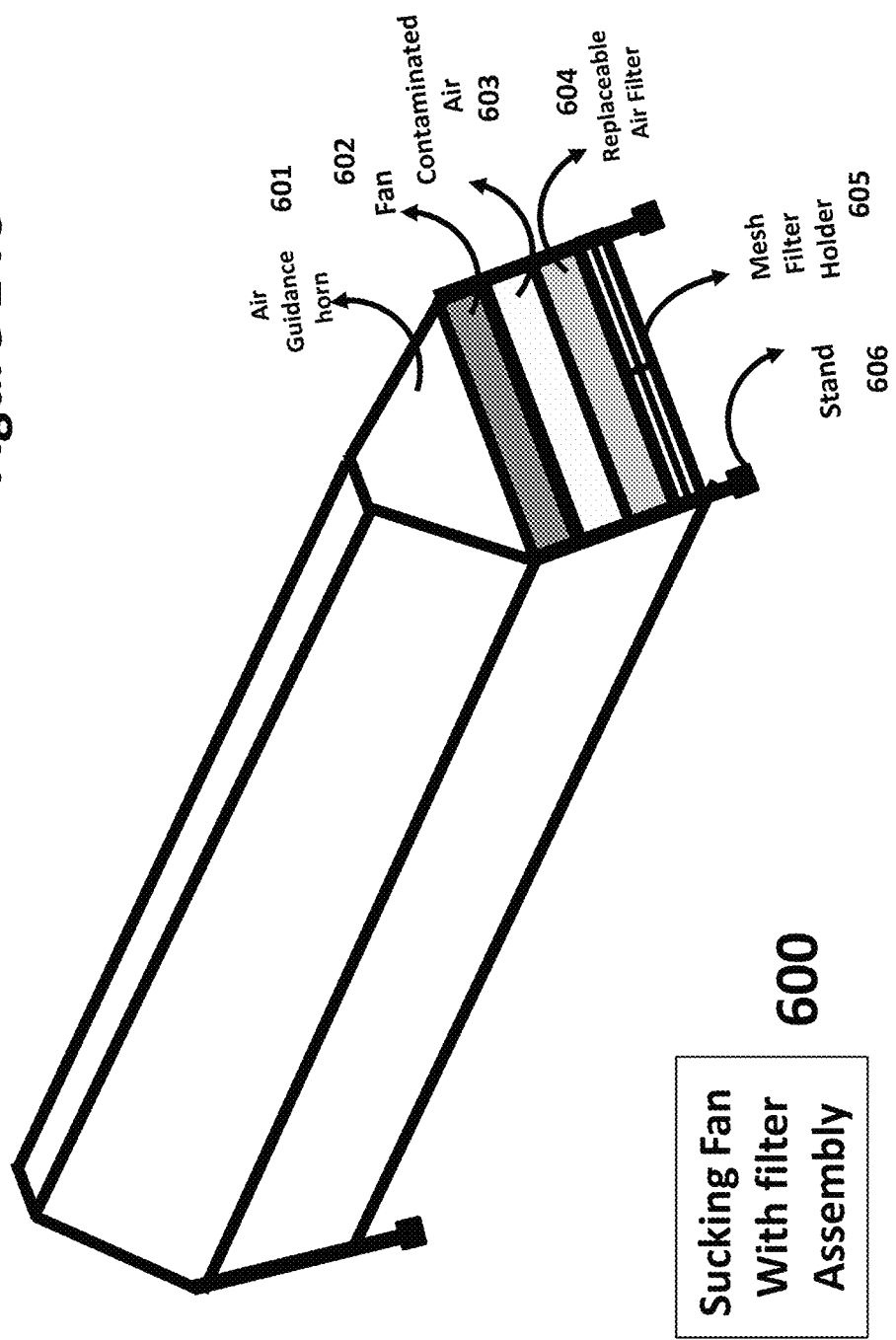

FIG. 14C depicts a sucking fan with filter assembly 600. Air enters the air sucking assembly 600 from opening of a guidance horn 601 and sucked by fan 602, send to contaminated air gap 603 before being filtered by aerosol filter 604 and released to environment through aerosol mesh filter holder 605. Sucking fan assembly 600 sits on a surface by stand 606. The aerosol filter is replaceable by removing the aerosol filter holder.

In one embodiment, an aerosol sucking fan assembly uses an attached aerosol filter that can be replaced when needed.

In another embodiment, an aerosol sucking fan assembly with attached aerosol filter is portable and sits on any flat surface.

FIG. 14D illustrates various views of a air sucking fan assembly 610. Air blowing assembly 590 can also be used by and air sucking fan. Air sucking fan assembly 610 has cross section 611 that shows air guidance horn 612, fan 613 in gray color, contaminated air 614, aerosol filter 615, mesh filter holder 616, and stand 617. The front and back view 618 of the air sucking fan assembly 618 shows air guidance horn, fan, and filter. The top view 620 of the air sucking fan assembly 610 shows air guidance horn and where air enters the air sucking fan. The bottom view 619 of the air sucking fan assembly 610 shows the mesh filter holder 616.

Figure 15:
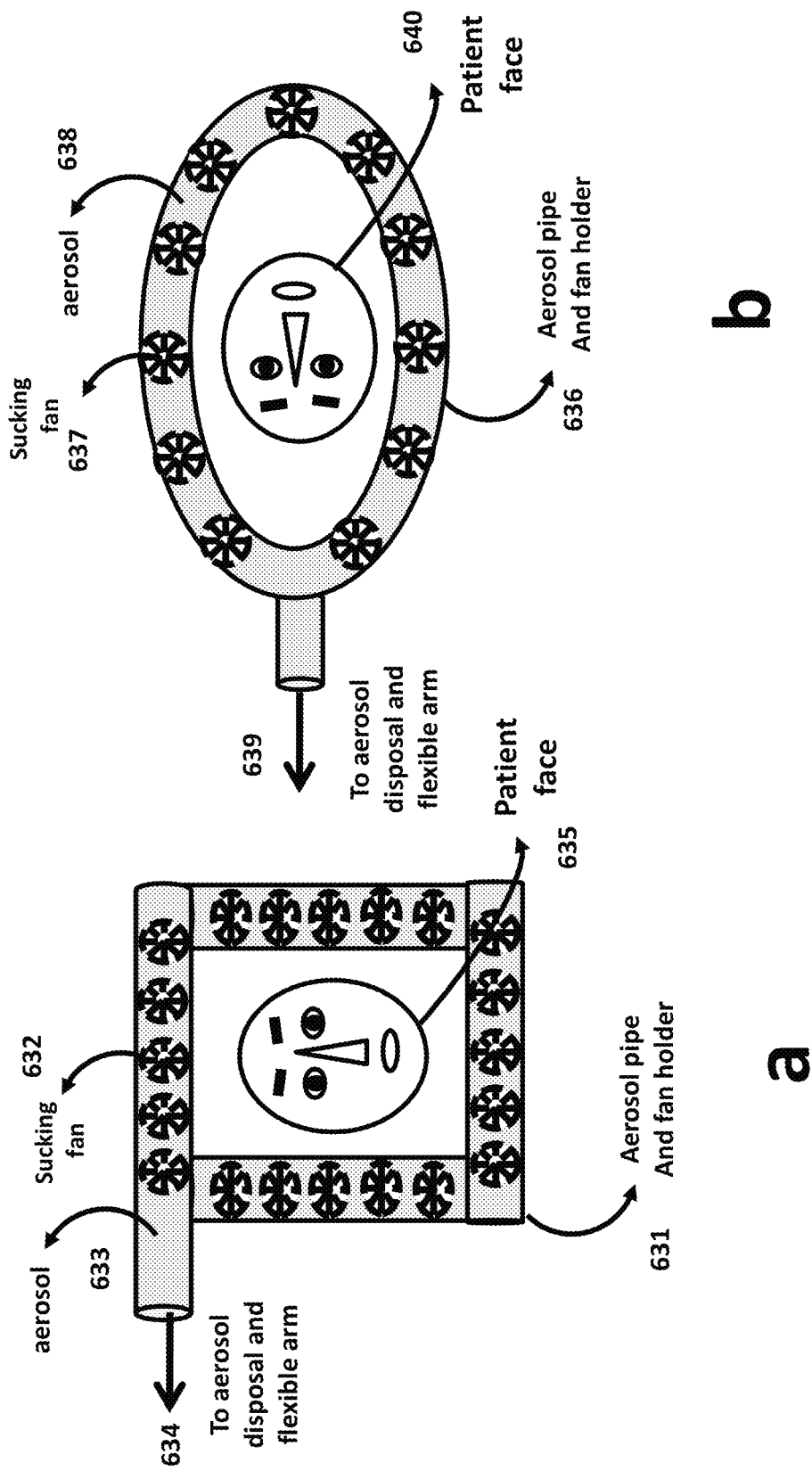
FIG. 15 shows two structures of patient aerosol sucking devices using sucking fans.

FIG. 15 shows a patient aerosol protection 630. Patient aerosol protection 630 sucks aerosol that exits a patient mouth and blocks the aerosol reaching anybody on the other side of patient aerosol protection 630. Patient aerosol protection 630 can have a circular, rectangular, elliptic or any arbitrary shape. Patient aerosol protection "a" has a rectangular aerosol pipe and fan holder 631, and sucking fan 632 along peripheral of the rectangle are used to suck the aerosol 633 and block them from going to the other side of patient aerosol protection 630. Patient aerosol protection "b" has an elliptical aerosol pipe and fan holder 636, and sucking fan 637 along peripheral of the elliptical pipe are used to suck the aerosol 638 and block it from going to the other side of patient aerosol protection 630. In both configurations "a" and "b" sucking fans 632, and 637 are hold by aerosol guiding pipes 631 and 636 that guide the aerosols 633 and 638 to an aerosol filter, or to an aerosol disposal. Aerosol guiding pipes 631 and 636 are similar to a ring with free space, transparent glass or other material in their middle.

Patient aerosol protection 630 includes, among other things, an aerosol pip fan holder 631 or 636, and sucking fan 632 or 637.

In one embodiment, a rectangular or elliptical aerosol pipe and fan holder uses sucking fan to block a patient's aerosol.

In another embodiment, aerosol guiding pipe is similar to a ring with free space, transparent glass or other material in its middle FIG. 16A depicts a portable aerosol shield 650. The portable aerosol shield 650 is self contained and has adjustable components to block aerosols from an aerosol source. The portable aerosol shield's blocking component 652 can have various shapes such as circle, rectangle, elliptic or arbitrary. The portable aerosol shield 650 uses sucking fan 654 to suck the aerosol comes toward it from one side of portable aerosol shield 650. The arm 653 that holds aerosol pipe and fan holder 652 is adjustable and flexible in order for portable aerosol shield to provide maximum protection. The height of the holder 651 of aerosol arm 653 and fan holder 652 is also adjustable for maximum blocking of aerosol. The aerosol pipe and fan holder 652 rotates 360 degree for maximum aerosol blockage. The aerosol pipe 652 guides the aerosol 655 to an aerosol filter 656 which is attached to the adjustable holder 651 and the output of the aerosol filter 656 which is clean air 658 is released to the environment. The sucking fan 654 is powered thought power line 657 from a power supply. The aerosol pipe and fan holder 652 is similar to a circular, rectangular or elliptical ring with nothing in the middle. The middle of aerosol pipe and fan holder can be transparent glass or plastic.

The portable aerosol shield 650 includes, among other things, adjustable holder 651, adjustable flexible arm and aerosol pipe 653, aerosol pipe and fan holder 652, sucking fan 654, and aerosol filter 656.

In one embodiment, fan holder that sucking fans are attached to it has various shapes, is rotatable, and its location is adjustable by a flexible arm holding it and a height adjustable holder of the flexible arm.

In another embodiment, aerosol pipe and fan holder that sucking fans are attached to is similar to a circular, elliptical, or rectangular ring that its middle is free space, transparent glass or transparent plastic.

In another embodiment, the aerosol protection shield is portable and self contained and has an attached aerosol filter to its adjustable holder.

In one embodiment, aerosol protection shield uses battery to power the sucking fans and the battery is attached to the adjustable holder of the aerosol protection shield.

Figure 16B:
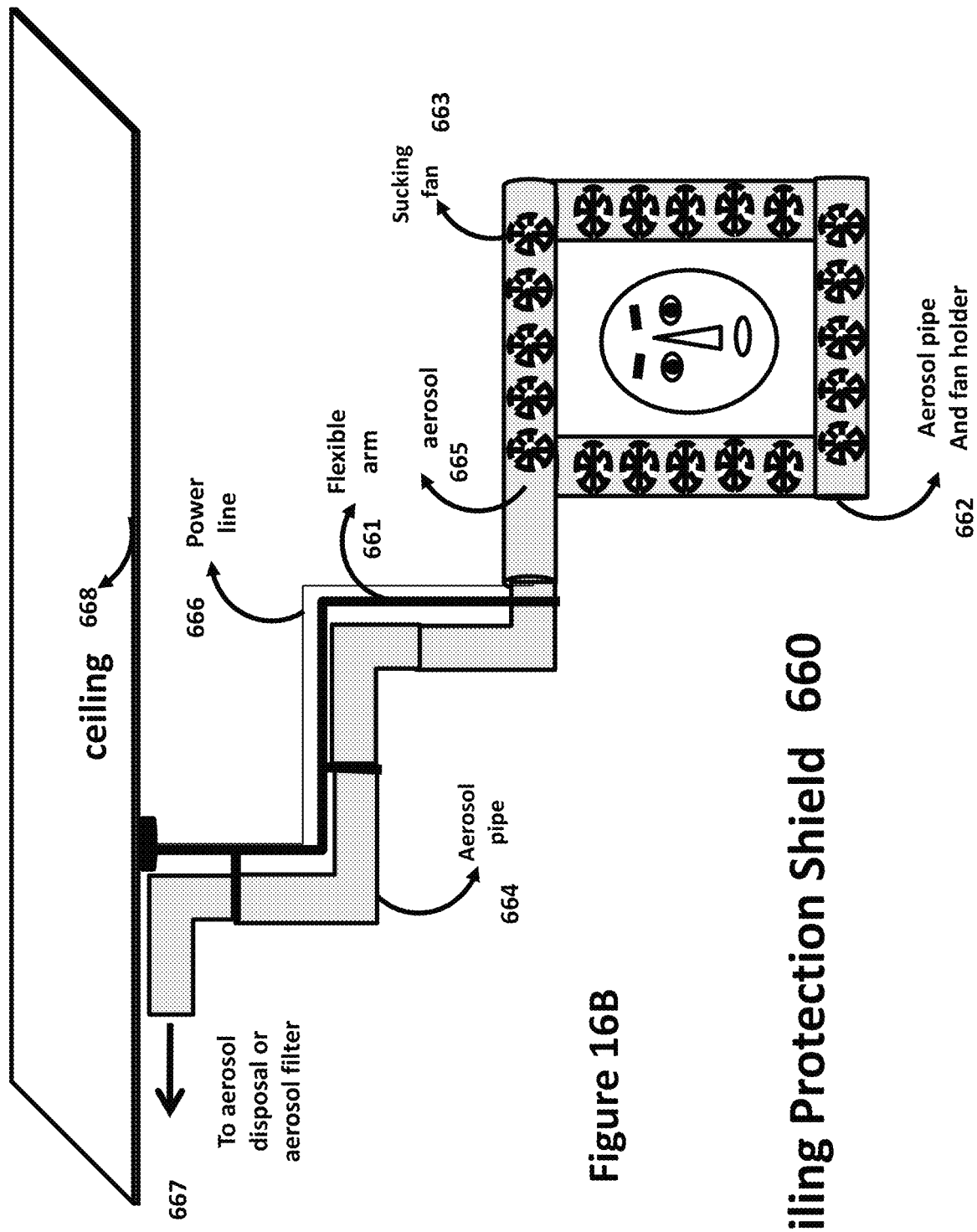

FIG. 16B shows a ceiling protection shield 660. The ceiling protection shield 660 has adjustable components to block aerosols from an aerosol source. The aerosol blocking component 662 (fan holder) has various shapes such as circle, rectangle, elliptic or arbitrary. The ceiling protection shield 660 uses sucking fan 663 to suck the aerosol comes toward it from one side of ceiling protection shield 660. The arm 661 that holds aerosol pipe 664 and fan holder 662 is connected to ceiling 668 and is adjustable and flexible in order for ceiling protection shield 660 to provide maximum protection. The flexible arm 661 is connected to the ceiling 668 of a room. The aerosol pipe and fan holder 662 can be rotated 360 degree for maximum aerosol blockage. The aerosol pipe 664 guides the aerosol 665 to an aerosol filter or aerosol disposal 667. The sucking fan 663 is powered through power line 666 from a power supply.

The ceiling protection shield 660 includes, among other things, flexible arm 661, aerosol pipe 664, aerosol pipe and fan holder 662, and sucking fan 663.

In one embodiment, an aerosol protection shield uses a flexible arm that is attached to a ceiling.

Figure 16C:
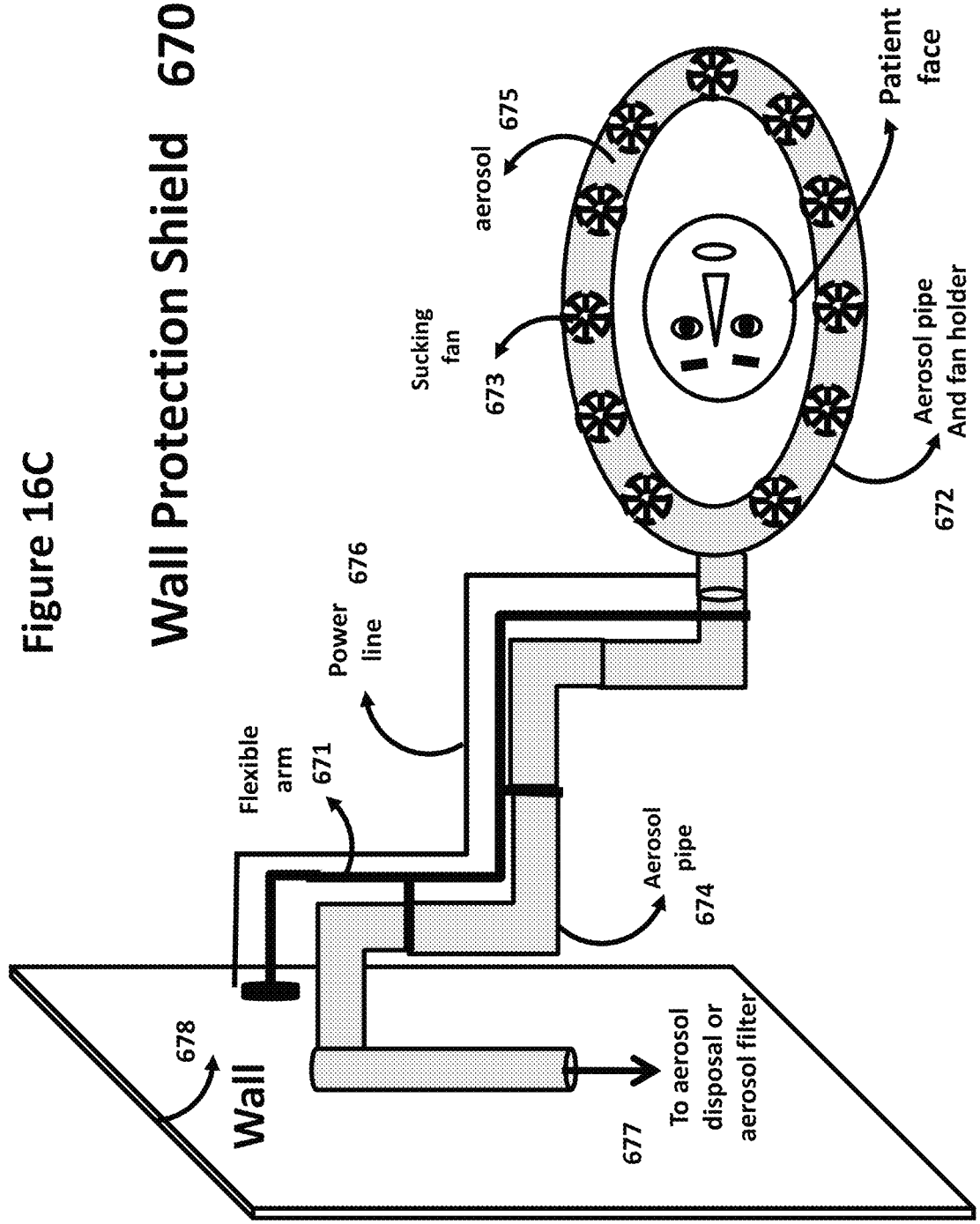

FIG. 16C shows a wall protection shield 670. The wall protection shield 670 has adjustable components to block aerosols from an aerosol source. The aerosol blocking component 672 have various shapes such as circle, rectangle, elliptic or arbitrary. The wall protection shield 670 uses sucking fan 673 to suck the aerosol comes toward it from one side of wall protection shield 670. The arm 671 that holds aerosol pipe 674 and fan holder 672 is adjustable and flexible in order for wall protection shield 670 to provide maximum protection. The flexible arm 671 is connected to a wall 678. The aerosol pipe and fan holder 672 rotates 360 degree for maximum aerosol blockage. The aerosol pipe 674 guides the aerosol 675 to an aerosol filter or aerosol disposal 677. The sucking fan 673 is powered through power line 676 from a power supply. The wall protection shield 670 can be covered by a transparent plastic or other material and become like a tent that has sucking fan at its ceiling. The transparent cover can have provision for a hand entering the tent through a hole or a sleeve.

The wall protection shield 670 includes, among other things, flexible arm 671, aerosol pipe 674, aerosol pipe and fan holder 672, and sucking fan 673.

In one embodiment, an aerosol protection shield uses a flexible arm that is attached to a wall.

Figure 17A:
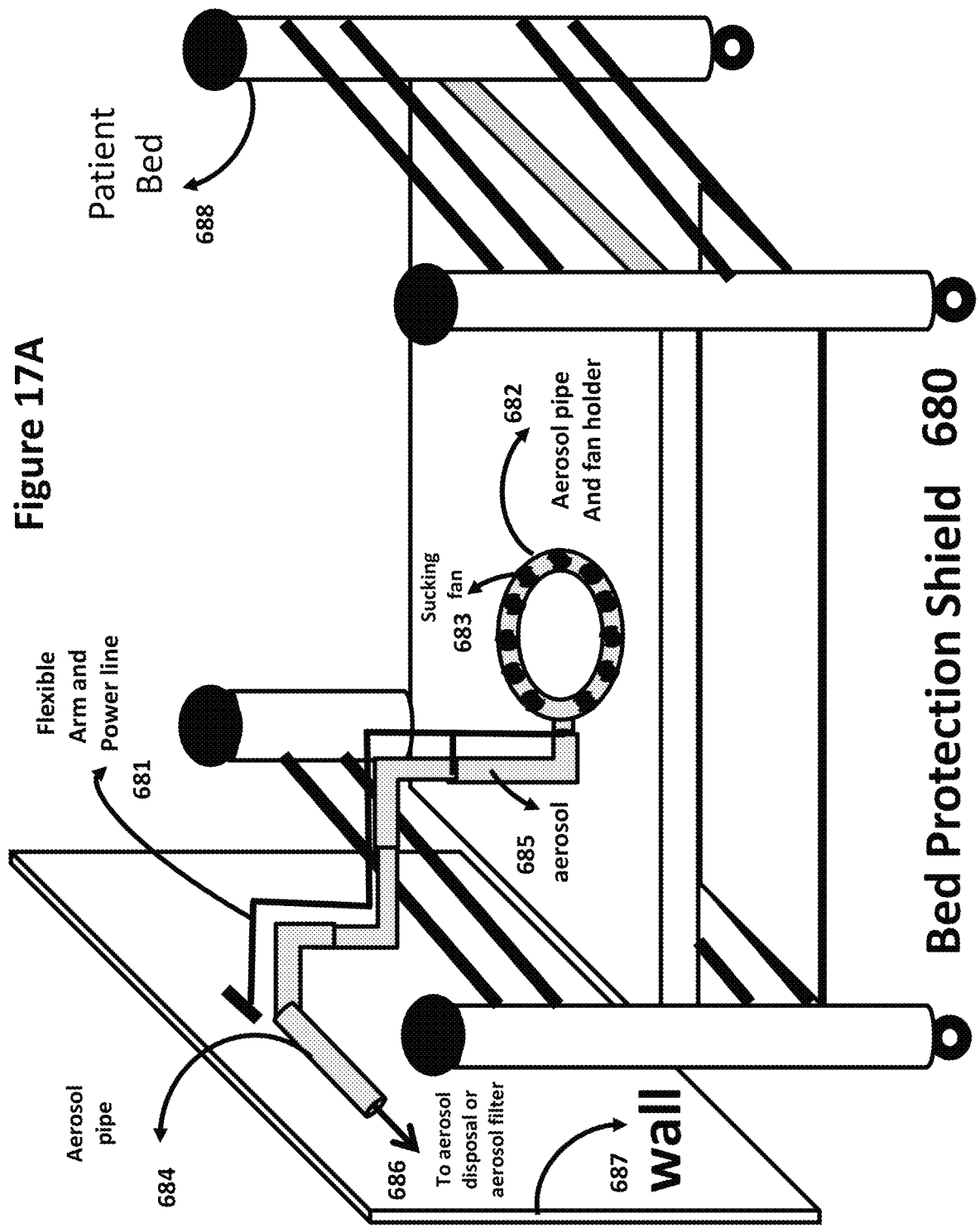
FIGS. 17A and 17B show how an aerosol sucking device supported with a flexible arm used for a bed.

FIG. 17A illustrate a bed protection shield 680. The bed protection shield 680 has adjustable components to block aerosols released by a patient lying in a hospital bed or sitting on a dentist seat. The aerosol blocking component 682 has various shapes like circle, rectangle, elliptic or arbitrary. The bed protection shield 680 uses air sucking fan 683 to suck the aerosol comes toward it from a patient lying in the bed 688. The arm 681 that holds aerosol pipe 684 and fan holder 682 is adjustable and flexible in order for bed protection shield 680 to provide maximum protection. The flexible arm 681 is connected to a wall 687 behind the patient bed. The aerosol pipe and fan holder 682 rotates 360 degree for maximum aerosol blockage. The aerosol pipe 684 guides the aerosol 685 to an aerosol filter or aerosol disposal 686. The sucking fan 683 is powered by battery or a power supply. The aerosol pipe and fan holder 682 with rectangular or elliptical architecture is covered by a flexible transparent material that resembles a tent with a ceiling that has sucking fans. The flexible transparent cover over the rectangular, circular or elliptical aerosol pipe and fan holder 682 has provision for a medical personal's hand in form of access holes or access sleeves.

The bed protection shield 680 includes, among other things, flexible arm 681, aerosol pipe 684, aerosol pipe and fan holder 682, and sucking fan 683.

In one embodiment, a bed protection shield uses a flexible arm that is attached to a wall to block aerosol released from a patient lying in a hospital bed.

In another embodiment, the aerosol pipe and fan holder 682 with rectangular or elliptical architecture is covered by a flexible transparent material that resembles a tent with a ceiling that has sucking fans.

In one embodiment, the flexible transparent cover over the rectangular, circular or elliptical aerosol pipe and fan holder 682 has provision for a person's hand in form of access holes or access sleeves.

Figure 17B:
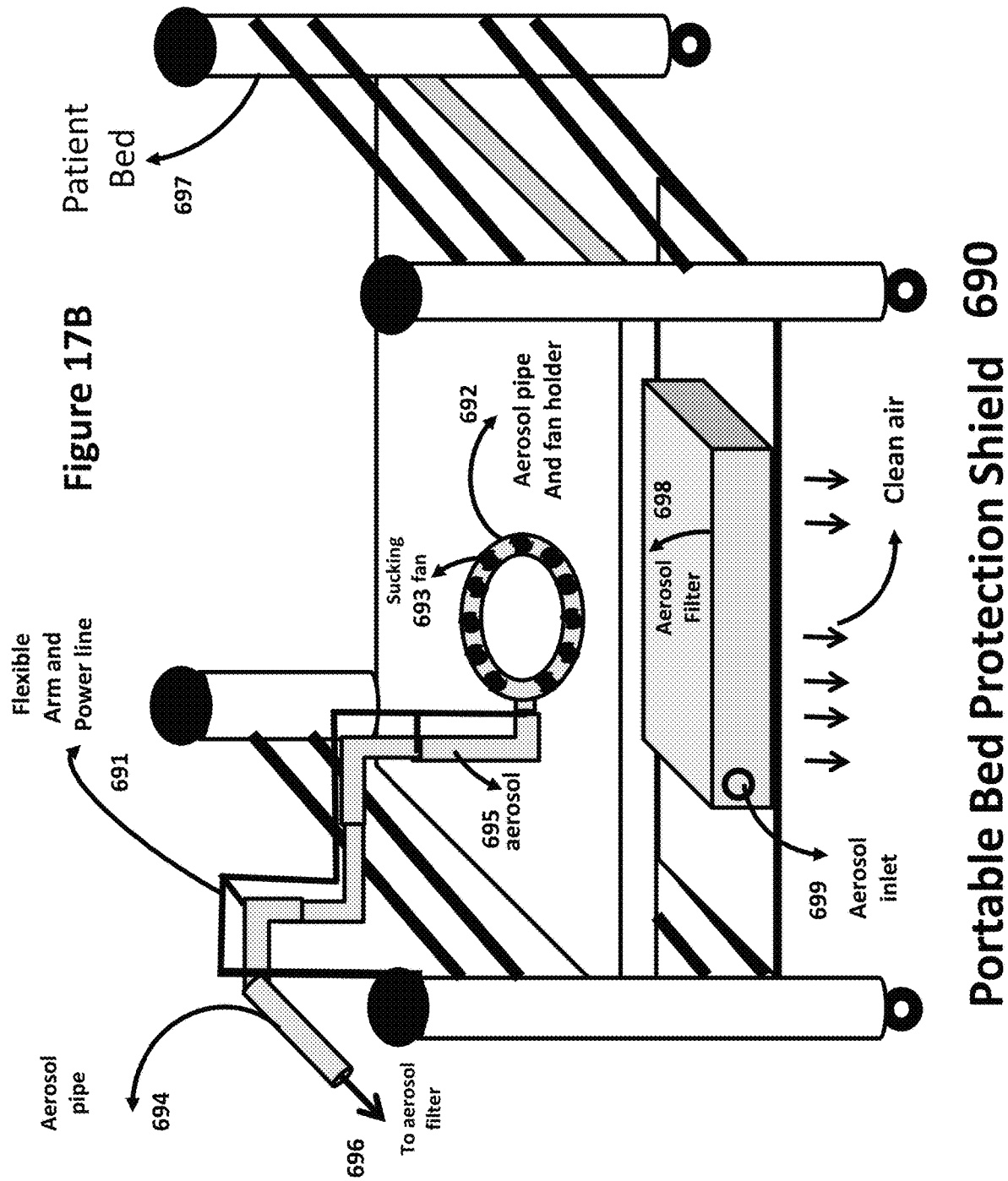

FIG. 17B illustrate a portable bed protection shield 690. The portable bed protection shield 690 has adjustable components to block aerosols released by a patient lying in a moving hospital bed. The aerosol blocking component 692 have various shapes such as a circle, a rectangle, an elliptic or an arbitrary. The portable bed protection shield 690 uses sucking fan 693 to suck the aerosol comes toward it from a patient lying in the bed 697. The arm 691 that holds aerosol pipe 694 and fan holder 692 is adjustable and flexible in order for portable bed protection shield 690 to provide maximum protection. The flexible arm 691 is connected to the bed stand behind the patient head. The aerosol pipe and fan holder 692 rotates 360 degree for maximum aerosol blockage. The aerosol pipe 694 guides the aerosol 695 to an aerosol filter 998 which is installed underneath the bed 697. The sucking fan 693 is powered by battery.

The portable bed protection shield 690 includes, among other things, flexible arm 691, aerosol pipe 694, aerosol pipe and fan holder 692, sucking fan 693, and aerosol filter 698.

In one embodiment, a bed protection shield uses a flexible arm that is attached to a patient bed to block aerosol released from a patient lying in a hospital bed that is moving.

In another embodiment, a bed protection shield has a flexible arm that is connected to the bed stand of a moving bed.

In one embodiment, a bed protection shield has aerosol filter that is installed underneath the moving bed.

FIG. 18A depicts a personal protection helmet 700. The personal protection helmet 700 is used by medical personal in hospitals, clinics, laboratories, as well as other people. The personal protection helmet 700 protects the person wearing it from any aerosol in the environment and blocks any aerosol from the person wearing it to penetrate to the environment. The personal protection helmet 700 uses sucking fans 701 to suck the air from environment then filter it from any potential aerosol in the environment by aerosol filter 702 and release clean air 703 to interior of the helmet 700 to be breathed by the person wearing the personal protection helmet 700. Personal protection helmet uses a transparent shield 707 connected to the fan and filter assembly and a plastic cover with a neck lock 708 that is attached to the transparent shield 707 and fan and filter assembly and through neck lock 709 totally isolate the air inside of personal protection helmet 700 from air in the environment. The air that is released 704 by the person who wears the personal protection helmet 700 is filtered from any aerosol by filter 705 and clean filtered air is sucked out of filter by sucking fan 706 and released to the environment. Personal protection helmet is controlled and powered by controller/battery 710 which is connected to the body of the person who wears the personal protection helmet 700.

Personal protection helmet 700 includes, among other things, sucking fan 701, aerosol filter 702, aerosol filter 705, sucking fan 706, transparent shield 707, plastic cover with locking knot 708, locking knot or fastening tape 709 and controller and battery 710.

In one embodiment, a battery operated helmet uses sucking fans, aerosol filters, transparent shield, and a plastic cover with a knot to totally isolate face of a person who wears the helmet from air in the environment.

In one embodiment, a battery operated helmet uses sucking fans, aerosol filters, transparent shield, and a plastic cover with a knot to totally isolate mouth, ear, nose, and eyes of the person who wears the helmet from air in the environment.

In another embodiment, the plastic cover with a knot used to block air from environment penetrating the inside air of the personal protection helmet is transparent.

In one embodiment, personal protection helmet 700 uses a plastic cover that is fastened to the neck by a fastening strap or tape.

In another embodiment, the plastic cover can use cloth or other flexible materials.

In one embodiment, a controller is used to adjust sucking power of sucking fans used in the personal protection helmet.

In another embodiment, a controller is used to collect data from various sensors installed in various location of personal protection helmet and uses the data to monitor certain safety parameters and compares them with certain pre-configured thresholds and make action if the thresholds are exceeded.

In one embodiment, the controller through information data receives from various sensors and devices used in the personal protection helmet controls the operation of the helmet.

In one embodiment, the fan and filter assembly has an "L" shape and vertical side of the "L" shape is used for sucking fans and horizontal side of "L" shape is used for aerosol filters.

In another embodiment, the transparent shield has a vertical straight or a vertical arc shape.

In one embodiment, the aerosol filters are replaceable.

In another embodiment, the battery which provides the power for the personal protection helmet is replaceable or rechargeable.

Figure 18B:
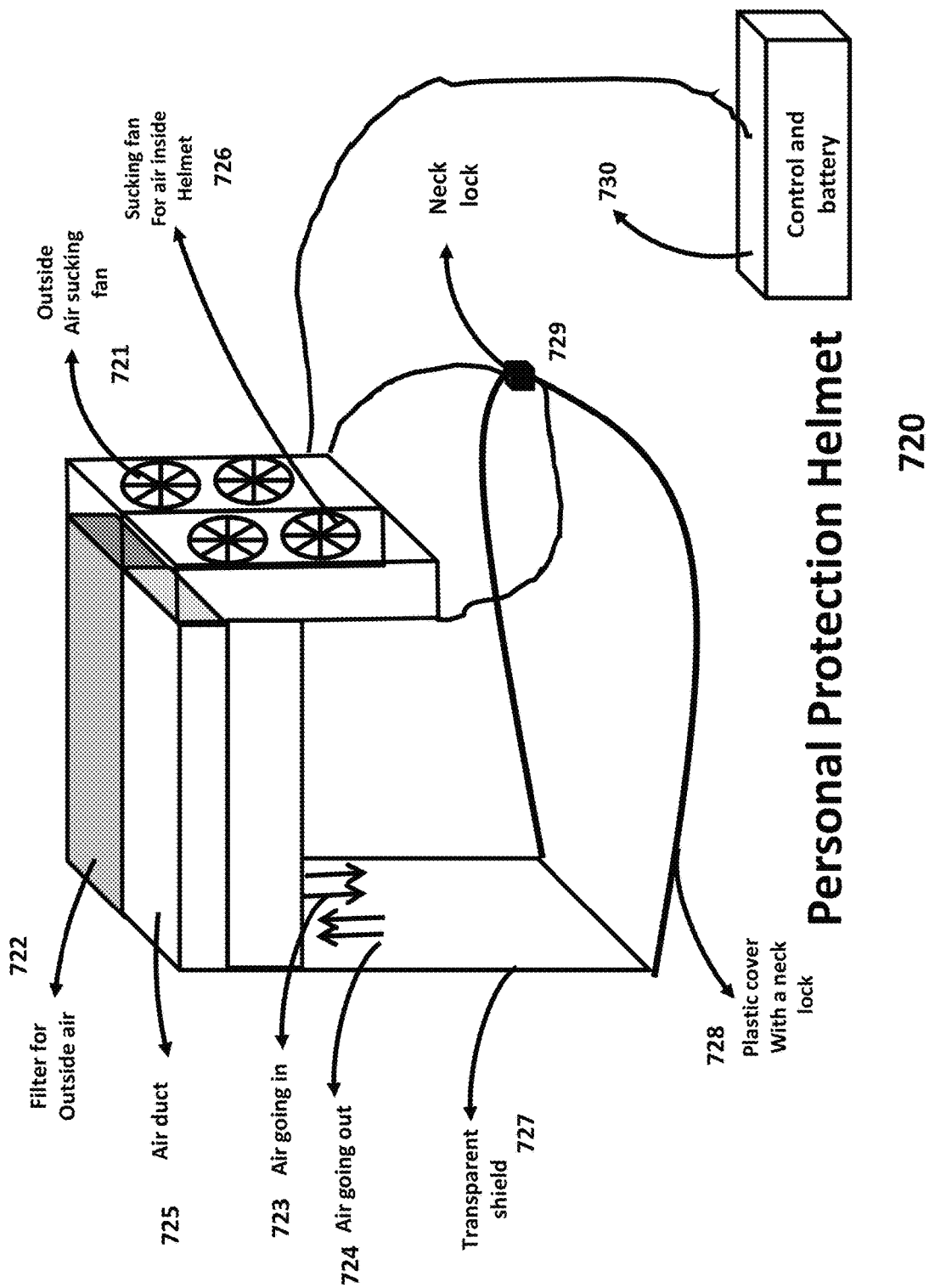

FIG. 18B illustrates a personal protection helmet 720. Personal protection helmet 720 is identical to personal protection helmet 700 and the only difference is that personal protection helmet 720 does not use an aerosol filter for the air that is sucked out of the interior of the helmet and released to the environment. Instead of aerosol filter an air duct is used.

FIG. 18C shows a personal protection helmet 740. Personal protection helmet 740 is identical to personal protection helmet 700. Personal protection helmet 740 shows how plastic cover 748 and transparent shield 747 cover the head of the person who wears the personal protection helmet 740. FIG. 18C shows how the plastic cover 748 isolates the head of the person from air in the environment by knotting the lock behind the neck of the person using neck knot 749. The plastic cover can also be a cloth cover and circle the neck of the person wearing the helmet and tightly knot at the back or front of the neck of the person similar to a Papillion. The cover also can be connected to the neck of a person wearing personal protection helmet 740 by a tape that stops any of the air in the environment penetrate interior of personal protection helmet 740. This objective can be achieved by a number of means and methods that is obvious to any person with skill.

FIG. 18D depicts a personal protection helmet 760. The personal protection helmet 760 is used by medical personal in hospitals, clinics, laboratories, and for other applications. The personal protection helmet 760 is also used by people who spray certain materials that could be toxic for a human being. The personal protection helmet 760 protects the person wearing it from any aerosol in the environment and blocks any aerosol from the person wearing it to penetrate to the environment. The personal protection helmet 760 uses sucking fans 761 to suck the air from environment then filter it from any potential aerosol in the environment by aerosol filter 762 and release clean air 763 to interior of the helmet 760 to be breathed by the person wearing the personal protection helmet 760. Personal protection helmet 760 uses a transparent shield 767 connected to the fan and filter assembly and a plastic cover with a neck lock 768 that is attached to the transparent shield 767 and fan and filter assembly and through neck lock 769 totally isolate the air inside of personal protection helmet 760 from air in the environment. The air that is released 764 by the person who wears the personal protection helmet 760 is filtered from any aerosol by filter 765 and clean air is sucked out of the filter 765 by sucking fan 766 and released to the environment. Personal protection helmet is controlled and powered by controller/battery 770 which is connected to the body of the person who wears the personal protection helmet 760.

Personal protection helmet 760 includes, among other things, sucking fan 761, filter 762, filter 765, sucking fan 766, transparent shield 767, plastic cover with locking knot 768, locking knot 769 and controller and battery 770.

In one embodiment, the fan and filter assembly has an "L" shape and vertical side of the "L" shape is used for aerosol filters and horizontal side of "L" shape is used for sucking fans.

In another embodiment, the vertical side of "L" shape is arced to fit the back of the head of the person wearing the personal protection helmet.

In another embodiment, the horizontal side of "L" shape is arced to fit the top of the head of the person wearing the personal protection helmet.

In one embodiment, personal protection helmet uses any arbitrary mechanical shape with all the components of the personal protection helmet that fits head of a person wearing it, and is light and highly durable and reliable.

In one embodiment, the aerosol filters are replaceable.

In another embodiment, the battery which provides the power for the personal protection helmet is replaceable or rechargeable.

In one embodiment, sensors are used to collect data related to the condition of the aerosol filter and sent the data to control to decide when the aerosol filter needs to be replaced and notify the person uses the personal protection helmet.

In one embodiment, noise cancellation for a personal protection helmet uses a microphone and speaker to reduce noise of the sucking fans.

In another embodiment, sample of ambient noise close to sucking fan is taken using a microphone attached to the helmet close to sucking fans and sent to controller to process.

In one embodiment, the controller collects the noise samples from the microphone, applies them to an algorithm that produces noise with opposite angle and sends it to a speaker which is closed to the sucking fans in order to dampen the noise from sucking fans.

Figure 18E:
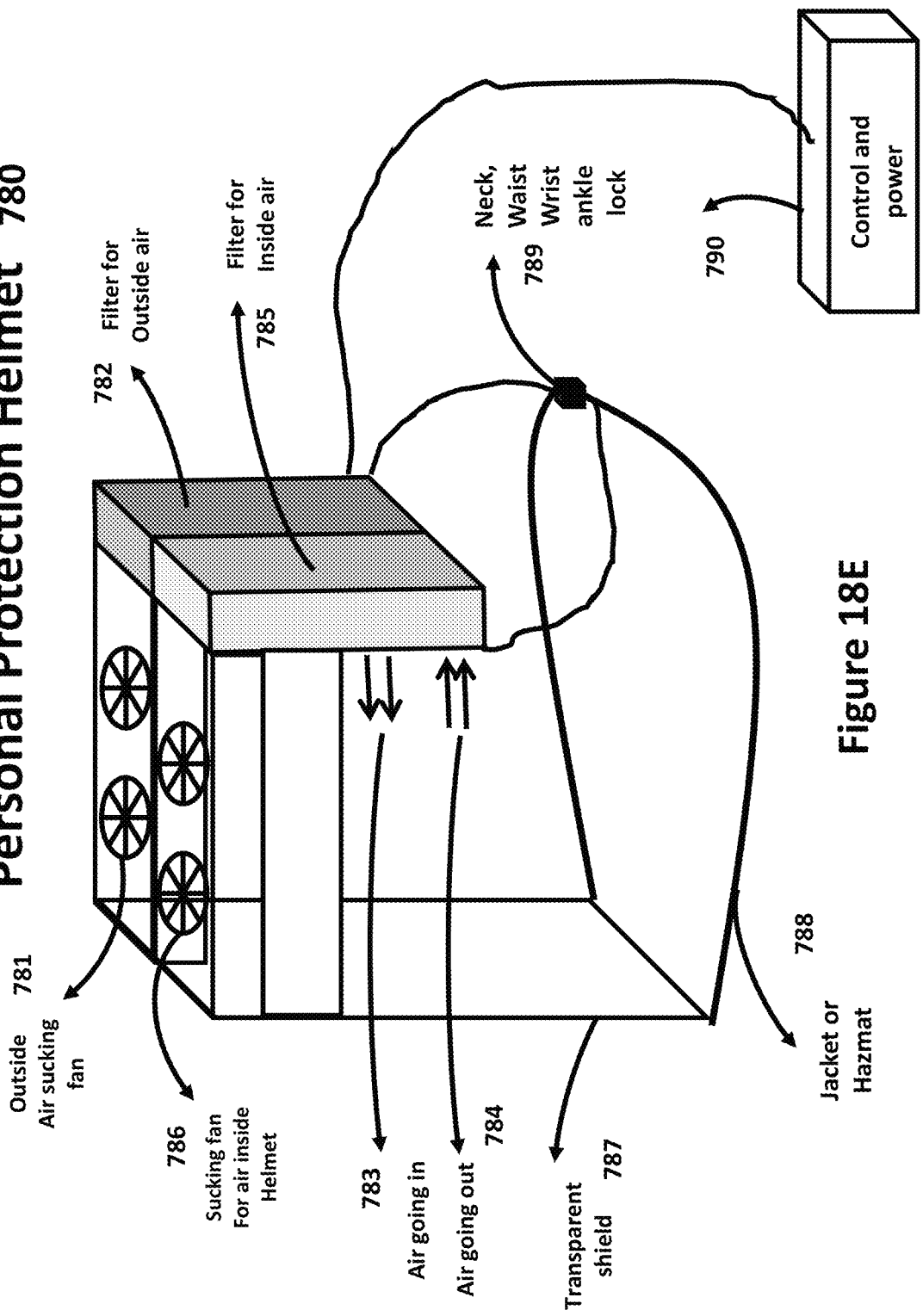

FIG. 18E depicts a personal protection helmet 780. The personal protection helmet 780 is used by medical personal in hospitals, clinics, and laboratories. The personal protection helmet 780 is also used by people who spray certain materials that could be toxic for a human being. The personal protection helmet 780 protects the person wearing it from any aerosol in the environment and blocks any aerosol from the person wearing it to penetrate to the environment. The personal protection helmet 780 uses sucking fans 781 to suck the air from environment then filter it from any potential aerosol in the environment by aerosol filter 782 and release clean air 783 to interior of the helmet 780 to be breathed by the person wearing the personal protection helmet 780. Personal protection helmet uses a transparent shield 787 connected to the fan and filter assembly and a plastic jacket cover with a neck lock 788, wrist and waist strap that is attached to the transparent shield 787 and fan and filter assembly and through neck lock 789 totally isolate the air inside of personal protection helmet 780 from air in the environment. The air that is released 784 by the person who wears the personal protection helmet 780 is filtered from any aerosol by filter 785 and clean air is sucked out of filter 785 by sucking fan 786 and released to the environment. Personal protection helmet is controlled and powered by controller/battery 790 which is connected to the body of the person who wears the personal protection helmet 780.

Personal protection helmet 780 includes, among other things, sucking fan 781, filter 782, filter 785, sucking fan 786, transparent shield 787, plastic jacket cover with locking knot 788, locking knot 789 and controller and battery 790.

In one embodiment, the plastic jacket cover 788 totally isolates the air inside the personal protection helmet from the air in environment.

In one embodiment, plastic jacket cover 788 instead of plastic uses cloth or other flexible materials.

In another embodiment, the plastic jacket cover uses waist fastening strap, a front zipper to the front shield, and a wrist fastening strap.

In another embodiment, the plastic jacket cover and pants are one piece and uses ankle fastening strap, wrist lock or fastening strap, and front zipper.

In one embodiment, the personal protection helmet is one piece and covers from ankle to wrist and uses front zipper up to transparent shield and fastening strap for the ankle and wrist.

Figure 18F:
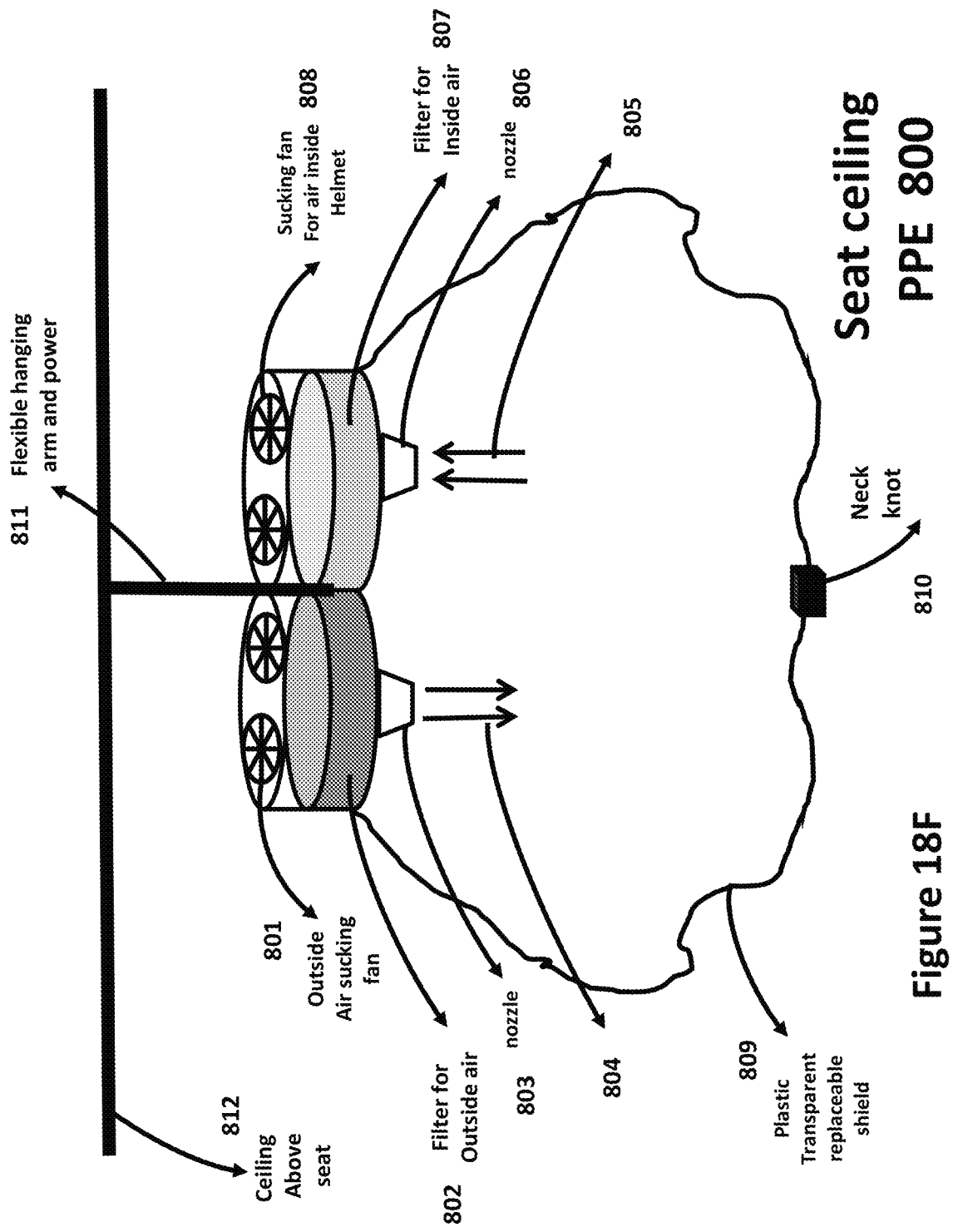

FIG. 18F depicts a seat ceiling personal protection equipment (PPE) 800. The PPE 800 is hanged from ceiling above a seat by a flexible and extendable arm 811 which is attached to ceiling 812. PPE 800 uses a sucking fan 801 to suck the air from environment, an aerosol filter 802 to filter the sucked air and releases clean air 804 to the interior of PPE 800 by nozzle 803. Contaminated air 805 from inside the PPE 800 through nozzle 806 and aerosol filter 807 is sucked by sucking fan 808 and clean air is released to the environment. A transparent face and head cover 809 is attached to the sucking fan and aerosol filter assembly and tightly attached to the person using PPE 800. The face and head cover 809 does not block mouth and nose of the person using PPE 800. The transparent face and head cover 809 covers a person's head down to the neck and uses a lock knot to tightly attach the cover to the neck without any environment air penetrating the interior of PPE 800 and any interior air being released to the environment. The transparent face and head cover 809 covers a person's head down to the neck and can also use a fastening strap to tightly attach the cover to the neck. The transparent face and head cover 809 also provides enough room for extensive movement of a person head without blocking mouth and nose of the person.

The PPE 800 includes, among other things, an extendable and flexible arm 811, sucking fan 801, aerosol filter 802, nozzle 803, nozzle 806, aerosol filter 807, sucking fan 808, transparent cover 809 and locking knot or fastening strap 810.

In one embodiment, a ceiling hanged PPE 800 is installed above seats of transportation vehicles such as airplane, train, taxi, trucks, and any personal vehicle.

In another embodiment, PPE 800 totally isolates head and face of a passenger from the air in the environment.

In one embodiment, PPE 800 through a pair of sucking fan and aerosol filter provides cleaned environment air to person wearing it and through another pair of aerosol filter and sucking fan sucks the interior contaminated air of PPE 800 and release clean air to the environment.

In another embodiment, PPE 500 uses a transparent cover which is tightly fastened, taped or glued to the aerosol filter and sucking fan assembly to create an interior environment that covers head and face of a person wearing it and is tightly fastened across the neck of the person without any air exiting or penetrating the PPE 800.

In one embodiment, the transparent cover used for PPE 800 in no circumstances blocks mouth or nose of the person wearing the PPE 800.

In another embodiment, the transparent cover used for PPE 800 follows all movements of the head of the person wearing the PPE 800.

In one embodiment, a PPE 800 is attached to a ceiling above a seat used by a passenger of a transportation vehicle with a flexible arm.

In another embodiment, the flexible arm used by PPE 800 is easily expandable in length and allows PPE 800 readily moves around.

In another embodiment, the flexible arm does not allow the PPE 800 to collapse and firmly bears the weight of the aerosol filters and sucking fans assembly.

In one embodiment, the aerosol filter and sucking fan assembly used for PPE 800 is very low weight.

In another embodiment, flexible arm provides power for the sucking fans.

In one embodiment, the aerosol filter has a sensor which through an LED light indicates when the filter needs to be replaced.

In another embodiment, the aerosol filter is readily replaceable.

In another embodiment, PPE 800 has sensors that monitor circulation of air and alarms if the circulation stopped, reduced from adjusted amount or a threshold.

In one embodiment, PPE 800 uses nozzles to adjust the amount of air enter and exit the head and face cover.

In another embodiment, PPE 800 uses nozzles to adjust the orientation of the air entering and exiting.

In one embodiment, when PPE 800 is not used it is collapsed and pushed up to attached to the ceiling.

Figure 18G:
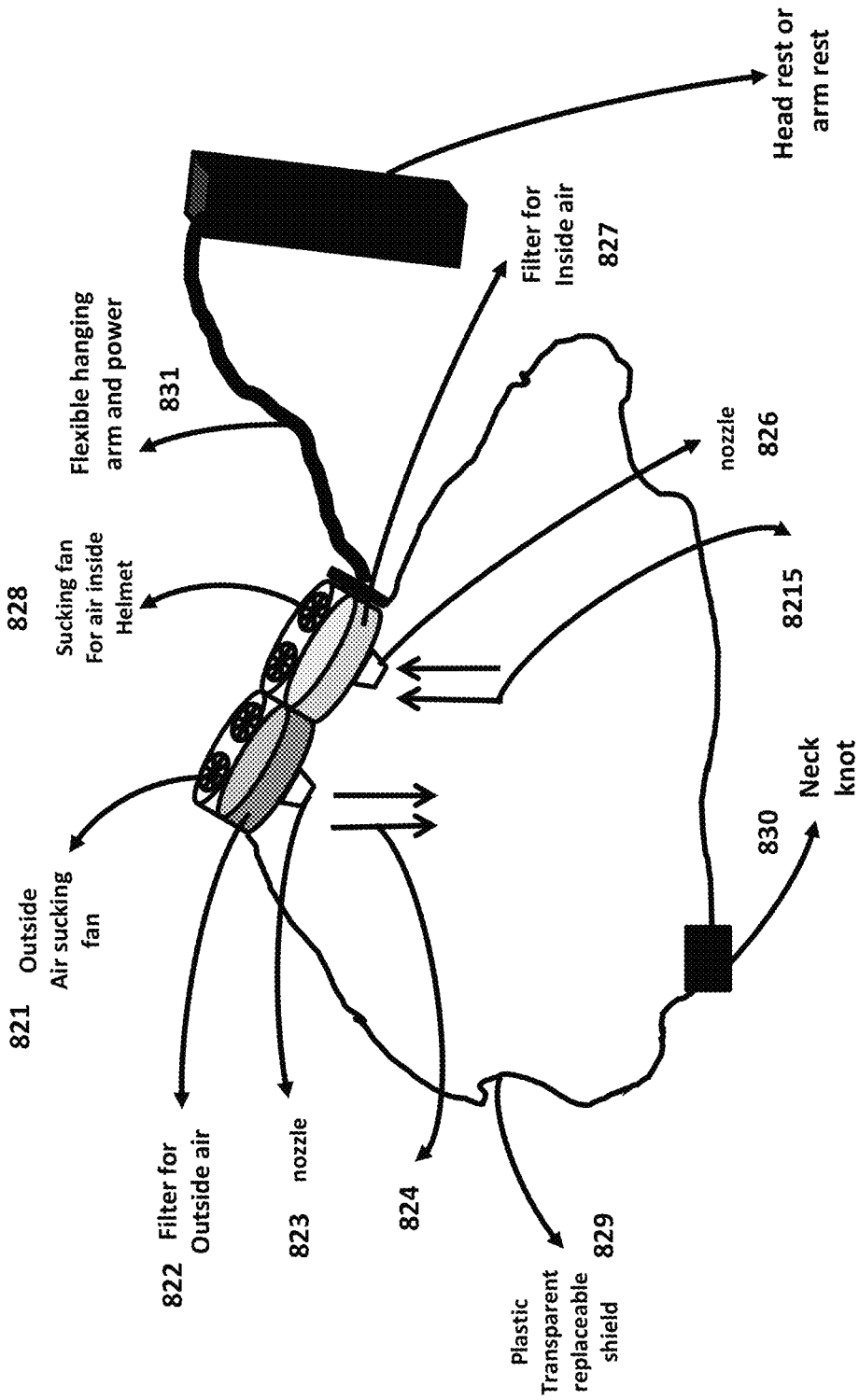

FIG. 18G shows a head rest PPE 820. Head rest PPE 820 is similar and identical to PPE 800. The only difference is that PPE 820 is attached to the top of the seat or head rest. The PPE 820 is attachable to various part of the seat. Possible places that PPE 820 can be installed are, top of the seat, head rest, arm rest, underneath of the seat, and if appropriate back of front seat.

In one embodiment, a flexible arm of PPE 820 is attached to head rest.

In another embodiment, the entire PPE 820 is placed inside the arm rest of a seat and when needed is pulled out.

In one embodiment, PPE 820 is installed underneath of a seat and pulled out and extended to the head through its flexible arm.

In another embodiment, when appropriate, PPE 820 is installed to the back of front seat and pulled out and extended to head through its flexible arm.

In one embodiment, PPE 820 rests in the magazine pocket of front seat and pulled out when needed.

In another embodiment, power to sucking fans and sensors used by PPE 820 are supplied by flexible arm that is attached to aerosol filter and sucking fan assembly.

Figure 18H:
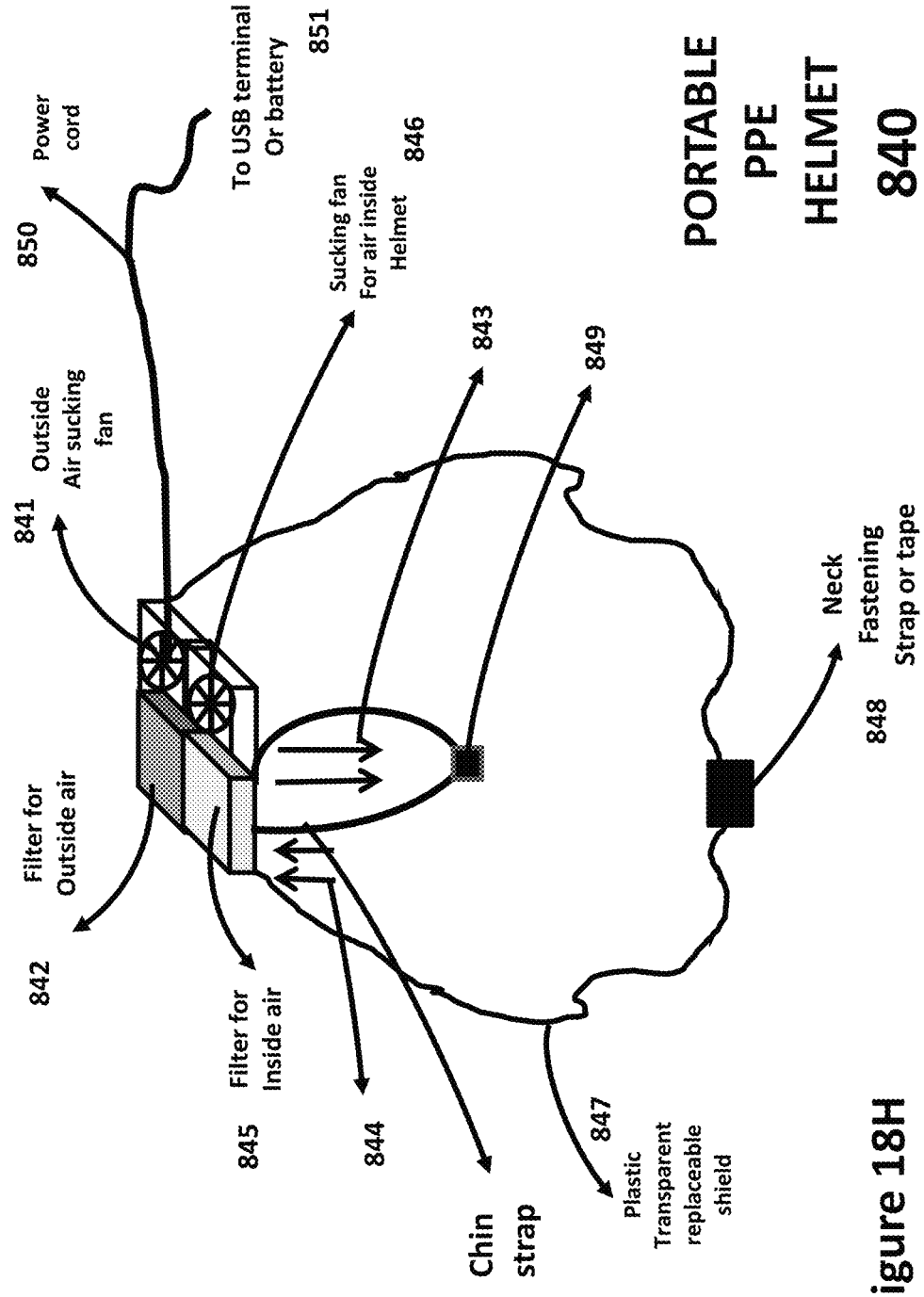

FIG. 18H illustrates a portable PPE helmet 840. PPE helmet 840 is a helmet that a passenger of a vehicle can wear. PPE helmet 840 is a personal item and owned by a passenger, rented to a passenger, or given to a passenger during travel by airplane, train, a taxi, or a personal vehicle. PPE helmet 840 has moving and active electronic components. PPE helmet 840 is portable and is carried by a traveler and used when needed in a vehicle. PPE helmet 840 is powered by a USB cable 850 that carries power and information data. Information data is exchanged between PPE helmet 840 and an external controller. PPE helmet 840 does not have a holding arm and needs to have a shape that fits head of a person.

PPE helmet 840 uses a sucking fan 841 to suck air from environment, an aerosol filter 842 to filter the sucked air from environment and releases clean air 843 to the interior of PPE helmet 840. Contaminated air 844 through aerosol filter 845 is sucked by sucking fan 846 and clean air is released to environment. A transparent face cover 847 is attached to the sucking fan and aerosol filter assembly and tightly attached to the person using PPE helmet 840. The face and head cover 847 does not block mouth and nose of the person using PPE helmet 840. The transparent face and head cover 847 covers a person's face down to the neck and uses a fastening strap 849 to knot under the chin and a neck lock knot 848 which is a fastening strap or tape to tightly attach the cover to the back of the neck without any environment air penetrating the interior of PPE helmet 840 and any interior air of PPE helmet 840 being released to environment. The transparent face and head cover 847 also provides enough room for extensive and freely movement of a person's head without blocking mouth and nose of the person.

The portable PPE helmet 840 includes, among other things, a sucking fan 841, aerosol filter 842, aerosol filter 845, sucking fan 846, transparent cover 847, chin strap 849, neck fastening strap or tape 848, and data and power USB cable 850.

In one embodiment, PPE helmet 840 is portable and is used to protect the person wearing it from any unwanted aerosol in the environment.

In another embodiment, PPE helmet 840 is powered by battery.

In one embodiment, PPE helmet 840 uses a USB cable to obtain power.

In another embodiment, PPE helmet 840 uses the USB cable to exchange information data with an external controller.

In one embodiment, PPE helmet 840 uses an attached or local controller to monitor the function of PPE helmet 840 and produce an alarm in case of malfunction or need for replacement of a component.

In another embodiment, PPE helmet 840 uses an external controller that is attached to the body of the Person who wears the PPE helmet 840 to monitor operation and produce an alarm in case of malfunction or need for replacement of a component.

In one embodiment, PPE helmet 840 uses a strap which fastened under the chin to hold the PPE helmet 840 steady when it is worn by a person.

In another embodiment, the controller used by PPE helmet 840 uses Bluetooth to communicate with an application of a smart phone.

In one embodiment, an application in a smart phone is used to communicate with controller attached to PPE helmet 840 or an external controller attached to the body of a person wearing PPE helmet 840 to configure the parameters for sucking fans and monitoring sensors used by PPE helmet 840.

In one embodiment, the transparent cover is a hazmat suit with no head cap connected to sucking fans, and aerosol filter assembly.

In another embodiment, the hazmat suit uses a front zipper, and wrist straps to totally isolate the interior of the helmet from environment and prevent any air leaks out to the environment and any air from environment leaks inside the helmet interior.

Figure 19A:
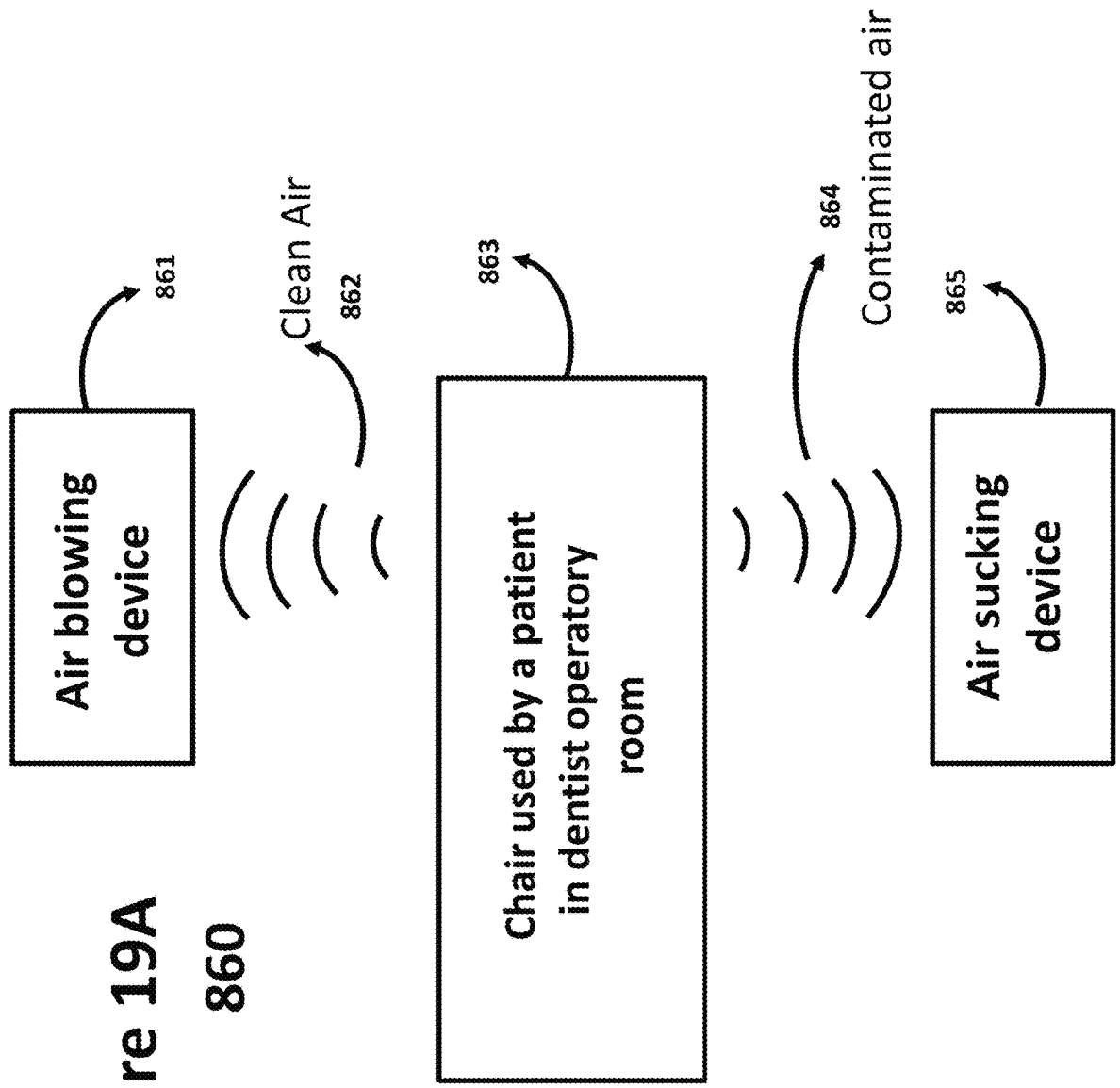
FIGS. 19A and 19B show use of aerosol protection system in a dentist operatory room.

FIG. 19A illustrates an aerosol protection system 860 used in a dentist operatory room. The operatory room is where a dentist and assistant dentist work on teeth of a patient. The operatory room contains various equipments that are used for treatment of the patient. The room is air conditioned to provide a comfortable temperature for patient, dentist and assistant while working on patient's teeth. The main equipment that is used by the patient is an adjustable chair. This chair can be adjusted to rotate, go up and down, move patient legs up and down to a comfortable position, and move patient head to a position that is comfortable and relaxing for the patient and allows the dentist and assistant(s) to work on patient's teeth easily without causing any discomfort to patient.

Aerosol protection system 860 uses an air blowing device 861 that blows clean air 862 towards the seat 863 used by a patient and focused towards the patient's mouth. Air blowing device 861 by blowing clean air at the aerosol coming out of the patient's mouth pushes the contaminated air 864 towards air sucking device 865 that sucks the contaminated air 864 and sends it to an aerosol filter or an aerosol disposal inlet.

Aerosol protection system 860 includes, among other things, an air blowing device 861, patient seat 863 and an air sucking device 865.

In one embodiment, an aerosol protection system for a dentist operatory room uses an air blowing device to blow at the aerosol released from mouth of a patient towards an air sucking device to be sucked and sent to an aerosol filter or an aerosol disposal inlet.

Figure 19B:
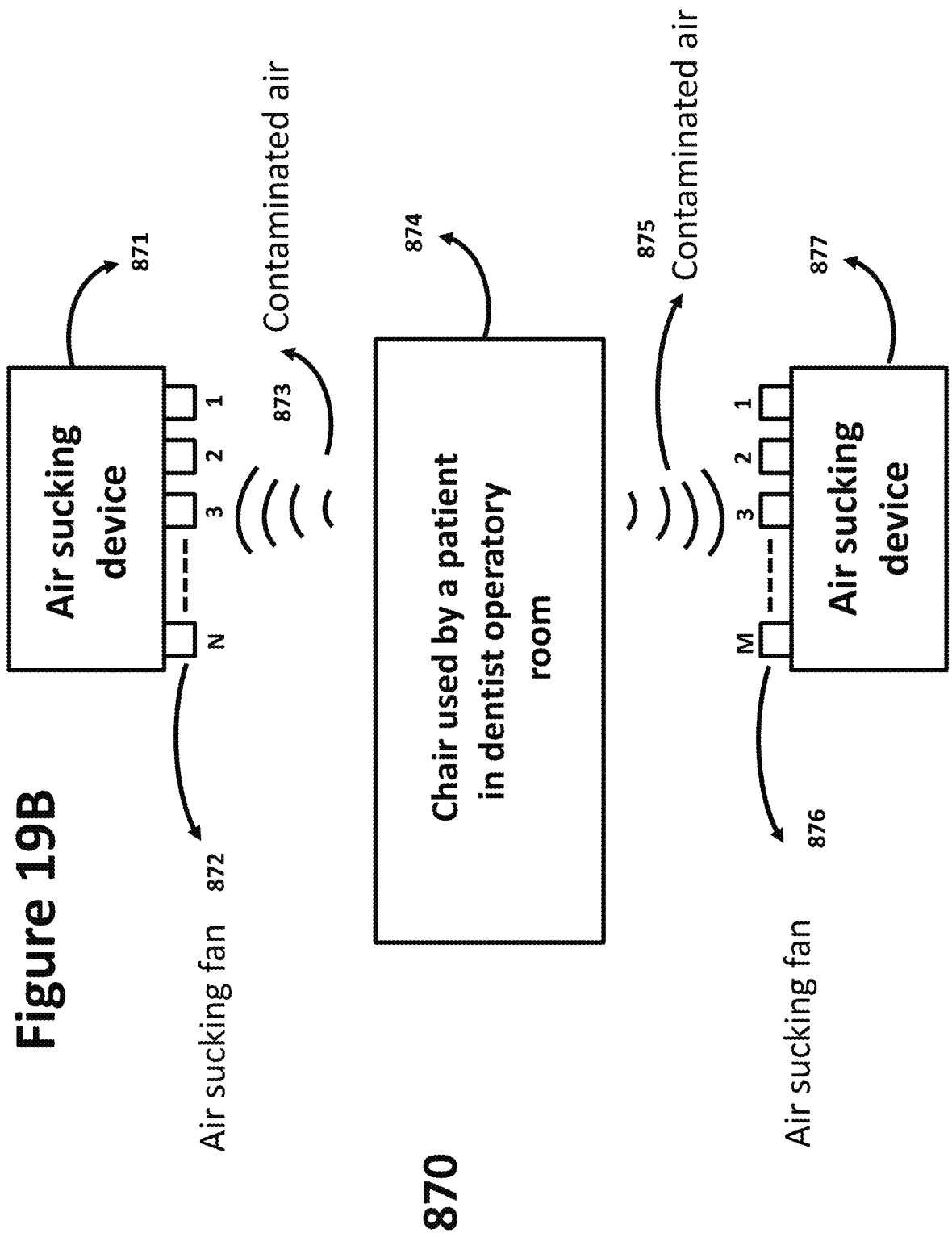

FIG. 19B illustrates an aerosol protection system 870 used in a dentist operatory room. Aerosol protection system 870 uses an air blowing device 861 that blows clean air 873 at the seat 874 used by a patient and focused towards the patient's mouth using air nozzle 872. Air blowing device 861 by blowing at aerosol coming out of the patient's mouth pushes the contaminated air 875 towards air sucking device 877 that sucks the contaminated air 875 through nozzle 876 and sends it to an aerosol filter or an aerosol disposal inlet.

Aerosol protection system 870 includes, among other things, an air blowing device 871, nozzles 872, patient seat 874, nozzles 876 and an air sucking device 877.

In one embodiment, an aerosol protection system for a dentist operatory room uses an air blowing device with adjustable nozzles to push the aerosol released from mouth of a patient towards an air sucking device with adjustable nozzles to be sucked and sent to an aerosol filter or an aerosol disposal inlet.

Figure 20:
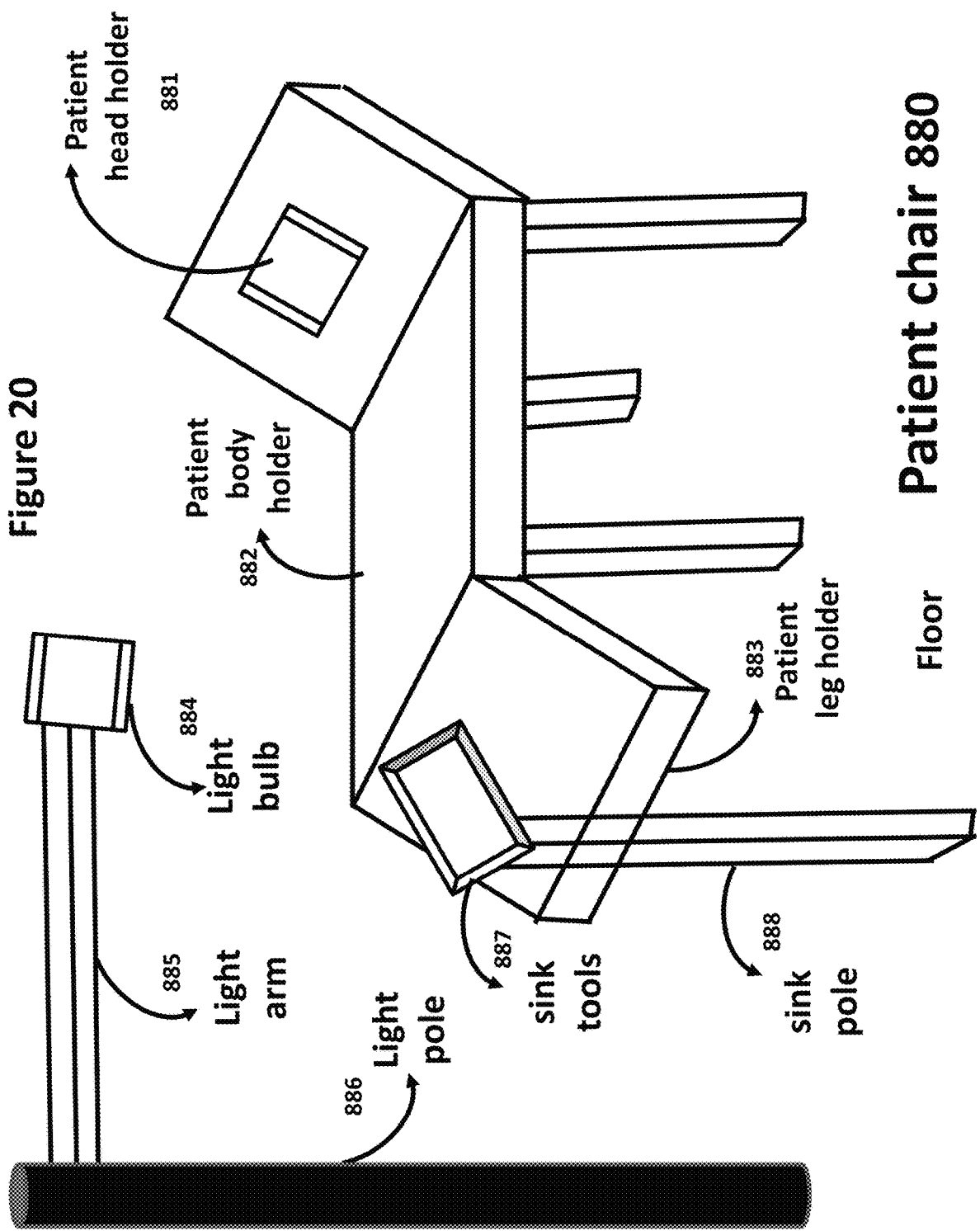
FIG. 20 illustrates the main equipments in a dentist operatory room.

FIG. 20 illustrates the patient chair 880 with its accessories in a dentist operatory room. The chair comprises of a patient leg holder 883, a body holder 882 and a head holder 881. The body holder 882 can be adjusted by the dentist or assistant to move up and down. The head holder 881 can be moved up or down for a position that dentist or assistant can operate or work on patient's teeth easily and with comfort. The foot holder 883 can also be rotated up and down to make the patient comfortable.

One of the accessories of patient chair 880 is a light arm that is flexible. The flexible arm 885 is attached to a pole 886 which stands on the floor and holds the power leads that feed electricity to the light bulb. The dentist or assistant adjust the flexible arm 885 for better vision of patient's mouth. The pole 886 can also hold a tool tray and electronic drills as well as supplying power to the drills. Another accessory is a pole 888 which holds a sink 887 and water tap. This is used when the patient needs to rinse mouth. The dentist and assistant chairs are at either side of the patient chair 880 which is stationary. Both dentist and assistant chairs have wheels and can be moved around for better access to the patient's mouth.

Figure 21:
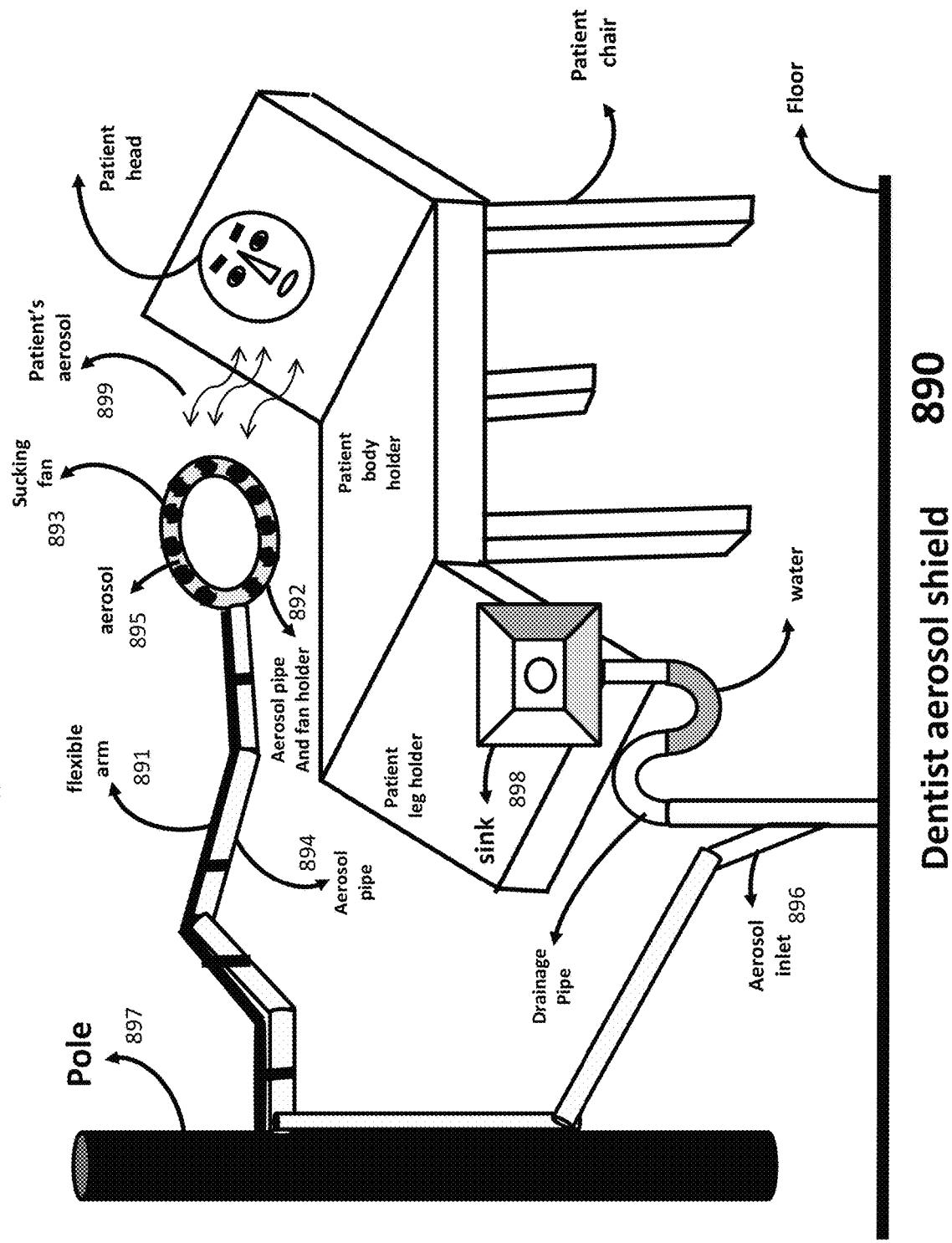
FIG. 21 shows use of an aerosol sucking device in a dentist operatory room.

FIG. 21 shows a dentist aerosol shield 890. The dentist aerosol shield 890 has adjustable components to block aerosols from a patient's mouth. The aerosol shield's blocking component 892 (fan holder) has various shapes like circle, rectangle, elliptic or arbitrary. The dentist aerosol shield 890 uses sucking fan 893 to suck the aerosol 899 that comes toward it from mouth of a patient. A flexible arm 891 that holds aerosol pipe 894 and fan holder 892 is connected to a pole 897 and is adjustable and flexible in order for dentist aerosol shield 890 to provide maximum protection. The flexible arm 891 is connected to pole 897 that holds other accessories and provides power to the fans and dentist light in the operatory room. The aerosol pipe and fan holder 892 can rotate 360 degree for maximum aerosol blockage. The aerosol pipe 894 guides the aerosol 895 to aerosol inlet 896 of sink 898.

The dentist aerosol shield 890 includes, among other things, flexible arm 891, aerosol pipe 894, aerosol pipe and fan holder 892, and sucking fan 893.

In one embodiment, a dentist aerosol shield uses air sucking fans to suck the aerosol that comes out of a patient's mouth.

In another embodiment, a dentist aerosol shield uses an aerosol pipe and fan holder with a rectangular, a circular or an elliptical structure.

In one embodiment, a dentist aerosol shield uses an aerosol pipe and fan holder that is covered by a flexible transparent material that resembles a tent with a ceiling that has sucking fans.

In one embodiment, the flexible transparent cover over the rectangular, circular or elliptical aerosol pipe and fan holder has provision for a person's hand in form of access openings or access sleeves.

In another embodiment, the aerosol disposal inlet of drainage pipe of a sink in dentist operatory room is used to dispose the aerosol sucked from mouth of a patient and the inlet to the drainage pipe is after the standing water.

Figure 22:
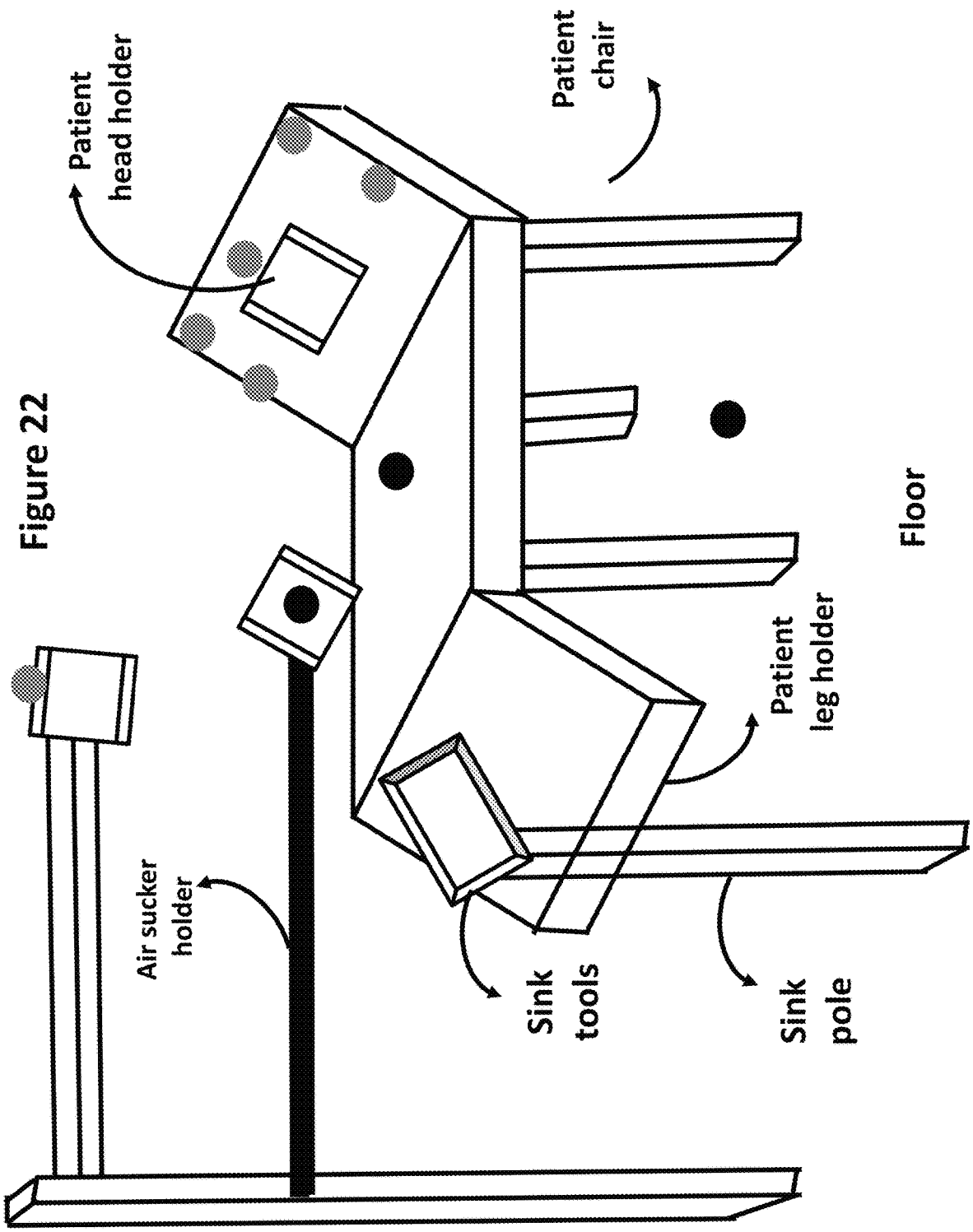
FIG. 22 depicts possible locations of air blowing and air sucking devices.

FIG. 22 shows the locations that air blowing device and air sucking device can be installed in a dentist operatory room when aerosol protection system shown in FIG. 19B is used. The gray circles show where the air blowing devices can be installed. At all these location air blowing device blow the air with the focal point being patient's mouth. The air blowing device can be installed at peripheral of light fixture, worn as a hat by patient, and above or on either side of patient's head holder or head rest.

The black circles illustrate the location of air sucking devices. Air sucking devices need to have a lower elevation compared to air blowing devices when air is blown from above patient's mouth. The black circle locations also need to have their focal point at patient's mouth. When air is blown at a location above the patient's mouth the air sucking device can be hold on body of the patient, on arm rest of the patient chair, or on a flexible arm that is connected to the power pole. When a flexible arm is used it is easy to adjust the air sucking device for maximum suction.

Figure 23:
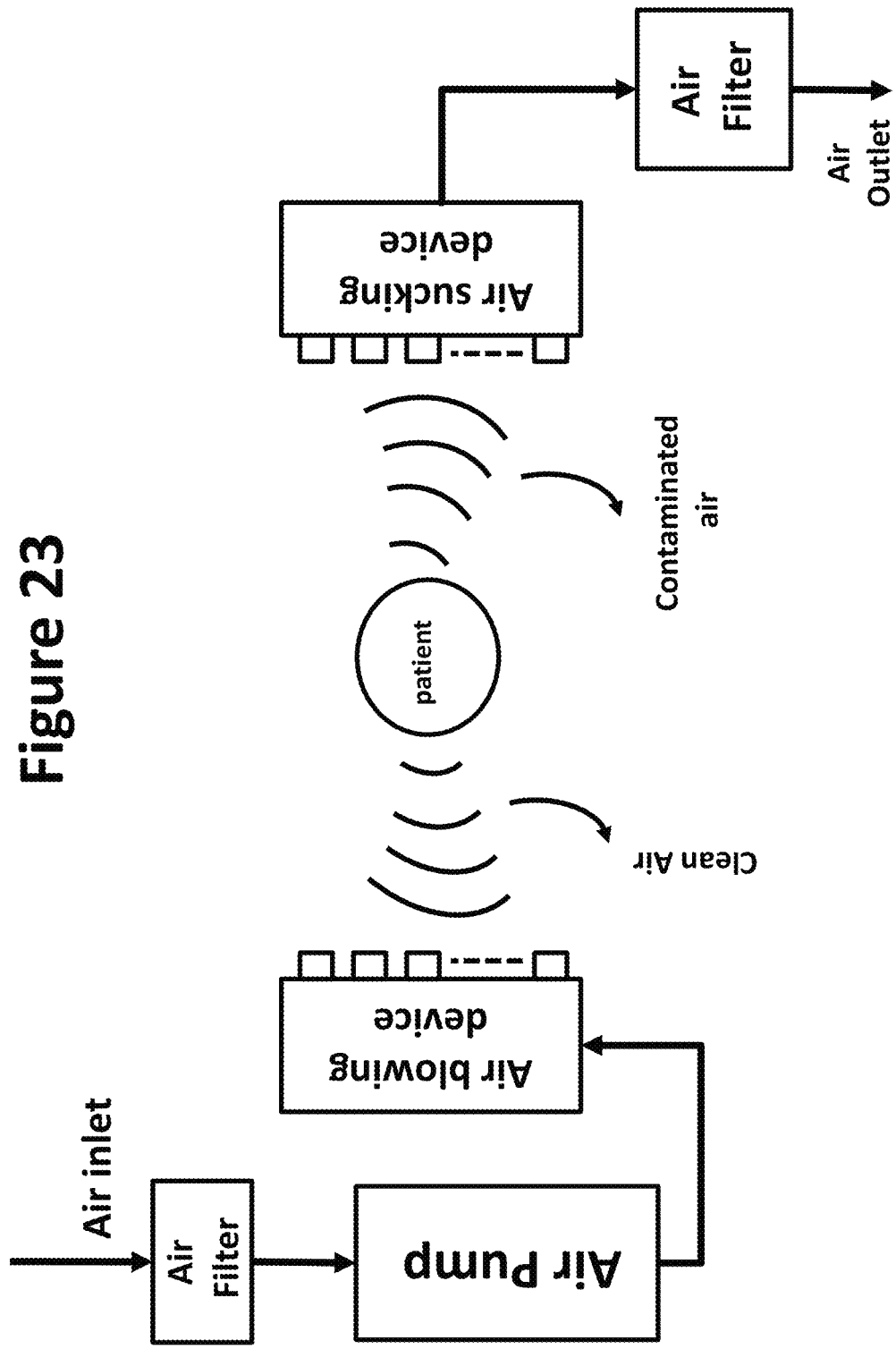
FIG. 23 depicts air blowing device and air sucking device possible accessories.

FIG. 23 shows the accessory components for air blowing device and air sucking device. The air inlet for air blower can be fresh air from outside or air from inside of dentist operatory room. In both cases there is a need to filter dust and any other particles that have contaminated the air. The filtered air is then pumped to air blowing device. To reduce any uncomfortable noise generated by the pumps, both air filter and the pump can be installed outside the operatory room or an efficient noise cancellation technique employed.

The contaminated air sucked by air sucking device is filtered and then released inside or outside the operatory room.

The filters used before air blowing device and after air sucking device are at least one of a HEPA (High Efficiency Particulate Air), a UV-C (high energy ultraviolet), and an electrostatic filter.

The inlet air also needs to be temperature controlled whether before being filtered or after filtering for a temperature that is comfortable for patient, dentist, and assistant.

FIG. 24 illustrates an aerosol transparent shield 900. The aerosol transparent shield 900 blocks passage of any aerosol from each side of the transparent shield to the other side of aerosol transparent shield 900. The transparent shield which is hold by holder 901 has a cluster of audio through holes 903 to facilitate audio communication from one side of transparent shield 900 to the other side of the transparent shield 900. The holder 901 is one piece and holds the transparent shield 902 from left, top and right edges. The holder can also have two pieces, one holding the left edge of transparent shield 902 and an aerosol filter 907 and a second one that hold right edge of the transparent shield 902. In order to block any aerosol that penetrates cluster of audio through holes 903 an aerosol sucking fan 904 is used above, below, left side or right side of the cluster of audio through holes 903. The aerosol sucking fan 904 can be installed either side of transparent shield 902. The aerosol sucking fan 904 is powered by power supply 906. The sucked aerosol by aerosol sucking fan 904 is guided to aerosol filter 907 by aerosol pipe 905.

Aerosol transparent shield 900 includes, among other things, shield holder 901, transparent shield 902, cluster of audio through holes 903, aerosol sucking fan 904, aerosol pipe 905, power supply 906, aerosol filter 907, and moving flexible plastic (other materials) 909.

Aerosol transparent shield 900 is portable and mobile and can be used at different locations. The aerosol transparent shield 900 has a gap between the transparent shield 902 and the surface holding the aerosol transparent shield 900. The gap is used for passing materials from one side of the transparent shield 902 to the other side of transparent shield. In order to stop any aerosol penetrating from one side of transparent shield to the other side through the gap between the transparent shield 902 and the surface a plastic (or similar material) tape 909 attached to transparent shield 902 that moves to front and back is used.

The aerosol transparent shield 900 has an aerosol filter 907 that is attached to the holder 901. Aerosol pipe 905 guides the aerosol sucked by sucking fan 904 to aerosol filter 907 and clean air 908 is released.

In one embodiment, a portable aerosol transparent shield with a cluster of audio through holes and aerosol sucking fan above, below, left side, or right side of the cluster of through holes is used to block aerosol from penetrating from one side of transparent shield to the other side of the transparent shield.

In another embodiment, a portable transparent shield is hold by a holder from left, top, and right edge of the transparent shield.

In one embodiment, a portable aerosol transparent shield is hold by two holders, one holds the left edge of transparent shield and an aerosol filter and a second one that holds right edge of the transparent.

In another embodiment, portable aerosol transparent shield has different size transparent shield by a holder that has adjustable height and width.

FIG. 25 depicts an air curtain 910. The air curtain 910 blocks passage of any aerosol from each side of the air curtain to the other side of the air curtain. Air is blown from top of the air curtain 910 by an air blowing fan 913 which is hold be a fan holder 912 and sucked at the bottom of air curtain 910 by an air sucking fan 915. The air blowing fan 913 gets its air 917 from environment and air sucking fan 915 sucks the blown air and through fan holder and aerosol pipe 914 sends it to aerosol filter 916 to be filtered and release clean air 918 to environment.

Air blowing fan 913 blows air from the top of air curtain 910 in a vertical surface that is a distance "d" spaced before the vertical surface that sucking fan 915 sucks air from. The distance "d" is adjustable for best performance of the air curtain 910. By adjusting CFM and orientations of the air blown by air blowing fan 913, distance "d" between the vertical surface that air is blown, sucking power and sucking orientation or direction of sucking fan 915 the performance of the air curtain 910 is adjusted for best performance.

In one embodiment, air curtain uses tandem fans for both air blowing and air sucking.

In another embodiment, the blowing fans and sucking fans are in two different vertical surface or line and operate as two curtains with a specified distance between them where the blowing air curtain that uses blowing fan at the top is before the sucking curtain that uses sucking fans at the bottom.

FIG. 26 depicts an aerosol sucking shield 920. The aerosol sucking shield 920 that is hold by holder 921 blocks passage of any aerosol from each side of shield to the other side of shield. Air is sucked from top and bottom of the aerosol sucking shield 920 by air sucking fan 923 at the top of the shield and air sucking fan 924 at the bottom of the shield. Both top air sucking fan 923 and bottom air sucking fan 924 are hold by a fan holder and air pipe 922. The air sucking fan 923, and 924 suck the air between two fans and through fan holder and air pipe 922 sends it to aerosol filter 925 to be filtered and release clean air 926 to the environment.

Aerosol sucking fan 913 sucks air from the top of shield 920 in a vertical surface that is a distance "d" spaced from the vertical surface that sucking fan 924 sucks from. The distance "d" is adjustable for best performance of the aerosol shield 920. By adjusting sucking power and orientations of the air sucked by air sucking fan 924, distance "d" between the vertical surfaces that air is sucked, sucking power and sucking orientation or direction of sucking fan 923 the performance of the aerosol shield 920 is adjusted for best performance.

In one embodiment, aerosol shield uses tandem fans for both top and bottom air sucking.

In another embodiment, the sucking fans are in two different vertical surface or line and operate as two shields with a specified distance between them where the sucking surface that uses sucking fan at the bottom is before the sucking surface that uses sucking fans at the top.

Various embodiments are thus described. While particular embodiments have been described, it should be appreciated that the embodiments should not be construed as limited by such description, but rather construed according to the following claims.

The invention claimed is:

1. An aerosol protection system to block passage of an aerosol from each side of the aerosol protection system to the other side comprising:
   A plurality of guiding horns having a trapezoidal shape with a narrow end comprising an opening and a wide end comprising a second opening;
   an air blowing device located at the top of the aerosol protection system comprising a first guiding horn, of the plurality of guiding horns, having an air outlet at the narrow end and an air inlet and a plurality of adjacent blowing fans on the wide end of the trapezoid;
   an air sucking device located at the bottom of the aerosol protection system comprising a second guiding horn, of the plurality of guiding horns, adjacent to a square prism, the second guiding horn comprising an air inlet at the narrow end and an air outlet at the wide end adjacent to the square prism and the square prism comprises a plurality of adjacent sucking fans adjacent to the wide end of the guiding horn, a replaceable air filter adjacent to the fans, and a removable mesh filter holder configured to hold the air filter inside the air sucking device;
   a holder to hold said air blowing device and said air sucking device;
   the air blowing device operates at a first vertical surface or plane and said air sucking device operates at a second vertical surface or plane with a distance between them to provide an air blowing curtain and an air sucking curtain; the air blowing device and the air sucking device comprises a means to adjust an orientation and a direction of the air blowing curtain or the air sucking curtain by configuring an air flow angle;
   the performance of said aerosol protection system is adjusted by bending or rotating inward or outward of said air blowing device or said air sucking device and changing the distance between the first vertical surface or plane and said second vertical surface or plane.

2. The aerosol protection system of claim 1, wherein said air blowing device uses said first guiding horn to control a speed, a cubic feet per minute (UM), and said orientation or said direction of a blown air.

3. The aerosol protection system of claim 2, wherein said air sucking device uses said second guiding horn to control an air sucking power and said orientation or said direction of a sucked air.

4. The aerosol protection system of claim 3, wherein said contaminated air sucked by said air sucking device is filtered before being released to the environment and said replaceable filter is a HEPA (high efficiency particulate air) filter or a ULPA (ultra-low particulate air) filter that is replaceable after a period of use.

5. The aerosol protection system of claim 3, wherein said CFM and said air sucking power are adjusted by changing a DC (direct current) or an AC (alternating current) operating voltage used by said plurality of adjacent blowing fans and said plurality of adjacent sucking fans.

6. The aerosol protection system of claim 5, wherein said blowing assembly and said sucking assembly use three or more adjacent fans.

7. A method for providing aerosol protection, the method comprising:
   A plurality of guiding horns having a trapezoidal shape with a narrow end comprising an opening and a wide end comprising a second opening;
   an air blowing device located at the top of the aerosol protection system corn rising a first guiding horn, of the plurality of guiding horns, having an air outlet at the narrow end and an air inlet and a plurality of adjacent blowing fans on the wide end of the trapezoid;
   an air sucking device located at the bottom of the aerosol protection system comprising a second guiding horn, of the plurality of guiding horns, adjacent to a square prism, the second guiding horn comprising an air inlet at the narrow end and an air outlet at the wide end adjacent to the square prism and the square prism comprises a plurality of adjacent sucking fans adjacent to the wide end of the guiding horn, a replaceable air filter adjacent to the fans, and a removable mesh filter holder configured to hold the air filter inside the air sucking device;
   an aerosol protection system that uses a holder to: hold the air blowing device connected at the top of said holder; and hold the air sucking device connected at the bottom of said holder; to blow air from top of said holder in a first vertical surface or plane by the air blowing device to create a first air curtain to block passage of an aerosol from one side to the other side of said first air curtain; and
   suck said aerosol by said air sucking device at the bottom of said holder in a second vertical surface or plane to create an air sucking curtain that has an adjustable distance from said first vertical surface or plane.

8. The method of claim 7, wherein a speed, an orientation and a direction of the air flow is achieved by the first or second guiding horn.

9. The method of claim 7, further the speed of the air blowing device, and an air sucking power of the air sucking device are controlled by changing a DC (direct current) operating voltage or an AC (alternating current) operating voltage of the plurality of adjacent blowing fans and the plurality of adjacent sucking fans.

\* \* \* \* \*